(12) United States Patent
Thurston et al.

(10) Patent No.: US 6,562,806 B1
(45) Date of Patent: May 13, 2003

(54) PYRROLOBENZODIAZEPINES

(75) Inventors: David Edwin Thurston, Nottingham (GB); Philip Wilson Howard, Nottingham (GB)

(73) Assignee: Spirogen Limited (GB)

( * ) Notice: Subject to any disclaimer, the term of this patent is extended or adjusted under 35 U.S.C. 154(b) by 0 days.

(21) Appl. No.: 09/763,814

(22) PCT Filed: Aug. 27, 1999

(86) PCT No.: PCT/GB99/02837

§ 371 (c)(1),
(2), (4) Date: Feb. 26, 2001

(87) PCT Pub. No.: WO00/12507

PCT Pub. Date: Mar. 9, 2000

(30) Foreign Application Priority Data

Aug. 27, 1998 (GB) .............................................. 9818731

(51) Int. Cl.⁷ ...................... A61K 31/555; A61K 31/55; C07D 223/10; C07D 487/00
(52) U.S. Cl. ...................... 514/185; 514/219; 514/220; 540/486; 540/494; 540/496
(58) Field of Search ................................ 540/486, 494, 540/496; 514/185, 219, 220

(56) References Cited

U.S. PATENT DOCUMENTS

| | | | |
|---|---|---|---|
| 3,523,941 A | 8/1970 | Leimbgruber et al. | ... 260/239.3 |
| 3,524,849 A | 8/1970 | Batcho et al. | ........... 260/239.3 |
| 4,185,016 A | 1/1980 | Takanabe et al. | ..... 260/239.3 T |
| 5,545,568 A | 8/1996 | Ellman et al. | ............... 436/518 |

FOREIGN PATENT DOCUMENTS

| | | |
|---|---|---|
| EP | 0 239 400 A2 | 9/1987 |
| FR | 2.027.356 | 12/1969 |
| FR | 2 586 683 | 3/1987 |
| JP | 58 180 487 | 10/1983 |
| WO | WO 88/07378 | 10/1988 |
| WO | WO 89/10140 | 11/1989 |
| WO | WO 92/19620 | 11/1992 |
| WO | WO 93/08288 | 4/1993 |
| WO | WO 93/18045 | 9/1993 |

OTHER PUBLICATIONS

Nagasaka et al., Stereoselective Synthesis of Tilivalline, Tetrahedron Letters, vol. 30, No. 14, pp. 1871–1872, 1989.*
Fukuyama et al., Total Synthesis of (+)–Porothramycin B, Tetrahedron Letters, vol. 34, No. 16, pp. 2577–2580, 1993.*
Wilson et al., Design and Synthesis of a Novel Epoxide–Containing Pyrrolo[2,1–c][1,4]benzodiazepine (PBD) via a New Cyclization Procedure, Tetrahedron Letters, vol. 36, No. 35, pp. 6333–6336, 1995.*
Katritzky et al., Heterocyclic Chemistry, John Wiley & Sons, Inc., 1960, pp. 247–253.*
Grant et al., Grant and Hackh's Chemical Dictionary, McGraw–Hill Book Company, 1987, p. 282.*

Bundgaard, H., "Design and Application of Prodrugs", 113–135, *A Textbook of Drug Design and Development*, eds Krogsgaard–Lassen, P., and Bundgaard, H., Harwood Academic Press (1991).
Foloppe, M.P., et al., "DNA–binding properties of pyrrolo [2,1–c][1,4]benzodiazepine N10–C11 amidines" *Eur. J. Med. Chem.,* 31, 407–410 (1996).
Kamal, A., et al., "An Efficient Synthesis of Pyrrolo[2,1–c] [1,4] Benzodiazepine Antibiotics via Reductive Cyclization," *Bioorg.Med.Chem.Ltrs,* v.7, No. 14, 1825–1828 (1997).
Kamal, A., et al. Synthesis of Pyrrolo [2,1–c][1,4]–Benzodiazepene Antibiotics: Oxidation of Cyclic Secondary Amine with TPAP, *Tetrahedron,* v. 53, No. 9. 3223–3230 (1997).
Thurston, D.E., "Synthesis of Sequence–selective C8–linked Pyrrolo [2,1–c][1,4] Benzodiazepine DNA Interstrand Cross–linking Agent," *J. Org. Chem.,* 61, 8141–9147 (1996).
Gregson, S. J. et al., "Synthesis of a novel C2/C2'–exo unsaturated pyrrolobenzodiazepine cross–linking agent with remarkable DNA binding affinity and cytotoxicity", *Chemical Communications,* 797–798 (1999).
Guiotto A. et al., "Synthesis of novel C7–aryl substituted pyrrolo[2,1–c][1,4]benzodiazepines (PBDs) via Pro–N10–troc protection and suzuki coupling", *Bioorganinc & Medicinal Chemistry Letters,* vol. 8, No. 21, 3017–3018 (1998).

(List continued on next page.)

Primary Examiner—Brenda Coleman
(74) Attorney, Agent, or Firm—Michael Best & Friedrich, LLP; Grady J. Frenchick, Esq.; Charlene L. Yager, Esq.

(57) ABSTRACT

A compound with formula (I)

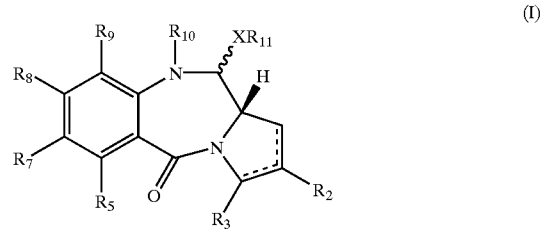

where $R_{10}$ is a therapeutically removable nitrogen protecting group; $R_2$ and $R_3$ are independently selected from: H, R, OH, OR, =O, =CH—R, =CH$_2$, CH$_2$—CO$_2$R, CH$_2$—CO$_2$H, CH$_2$—SO$_2$R, O—SO$_2$—R, CO$_2$R, COR and CN; $R_6$, $R_7$ and $R_9$ are independently selected from H, R, OH, OR, halo, amino, nitro, Me$_3$Sn; X is S, O or NH; $R_{11}$ is either H or R; and where there is optionally a double bond between C1 and C2 or C2 and C3; and $R_8$ is selected from H, R, OH, OR, halo, amino, nitro, Me$_3$Sn, or $R_7$ and $R_8$ together form a group —O—(CH$_2$)$_p$—O—, where p is 1 or 2. Such compounds may be used in methods of ADEPT, GDEPT, NPEPT or PDT.

25 Claims, 10 Drawing Sheets

OTHER PUBLICATIONS

Leimgruber et al., *Am. Chem. Soc.,* 87, 5793–5795 (1965).
Leimgruber et al., *J. Am. Chem. Soc.,* 87, 5791–5793 (1965).
Thurston et al., *Chem. Rev.,* 1994, 433–465 (1994).
Hochlowski et al., *J. Antibiotics,* 40, 145–148 (1987).
Konishi et al., *J. Antibiotics,* 37, 200–206 (1984).
Thurston et al., *Chem. Brit.,* 26, 767–772 (1990).
Bose et al., *Tetrahedron,* 48, 751–758 (1992).
Kunimoto et al., *J. Antibiotics,* 33, 665–667 (1980).
Takeuchi et al., *J. Antibiotics,* 29, 93–96 (1976).
Tsunakawa, et al., *J. Antibiotics,* 41, 1366–1373 (1988).
Shimizu et al., *J. Antiobiotics,* 35, 972–978 (1982).
Langley and Thurston, , *J. Org. Chem.,* 52, 91–97 (1987).
Hara et al., *J. Antibiotics,* 41, 702,704 (1988).
Itoh et al., *J. Antibiotics,* 41, 1281–1284 (1988).
Leber et al., *J. Am. Chem. Soc.,* 110, 2992–2993 (1988).
Arima et al., *J. Antibiotics,* 25, 437–444 (1972).
Kohn, *Antibiotics III,* Springer–Verlag, NY, 3–11 (1975).
Hurley and Needham–VanDevanter, *Acc. Chem. Res.,* 19, 230–237 (1986).
Althuis, T. H. and Hess, H. J "Synthesis and Identification of the Major Metabolites of Prazosin Formed in Dog and Rat", *J. Medicinal Chem.,* 20(1), 146–266 (1977).
Nagasaka, T. et al.,. "Stereoselective synthesis of tilivalline", *Journal of Organic Chemistry,* vol. 36, No. 20, 6797–6801 (1998).
Baraldi, P. G. et al., "Design, synthesis and biological activity of a pyrrolo[2,1–c][1,4]benzodiazepine (PBD)–distamycin hybrid", *Bioorganic & Medicinal Chemistry Letters,* vol. 8, No. 21, 3019–3024 (1998).
Huber et al., *Proc. Natl. Acad. Sci. USA,* 88, 8039 (1991).
Morgan & French, *Annu. Rev. Biochem.,* 62, 191 (1993).
Lewis et al., *Carcinogenesis,* 9, 1283–1287 (1988).
Kuzmich et al., *Journal of Biochemistry,* 281, 219–244 (1992).
Culver et al., *Science,* 256, 1550–1552 (1992).
Englehardt et al., *Nature Genetics,* 4, 27–34 (1993).
Ram, Z. et al., *Cancer Research,* 53, 83–88 (1993).
Dalton & Treisman, *Cell,* 68, 597–612 (1992).
Mizushima and Nagata, *Nucl. Acids Res.,* 18, 5322 (1990).
Tew et al., Glutathione–S–tranferase and anti–cancer drug resistance in Mechanism of Drug Resistance in Neoplastic Cells, Wooley, P.V., Tew K. D., Eds, Academic Press: Oralndo, FL 141–159 (1987).
Satyam et al.,*Med. Chem.,* 39, 1736–1747 (1996).
Nicolaou et al. *Science,* 256, 1172–1178 (1992).
Jungheim, L. N. and Shepherd, T. A., "Design of Antitumor Prodrugs: Substrates for Antibody Targeted Enzymes", *Am. Chem. Soc. Chem. Rev.,* 96: 6, 1553–1566 (1994).
Pillai, R. V. N., "Photoremovable protecting groups in organic chemistry", *Synthesis,* 1–26 (1980).
Bayley, H., Gasparro, F., and Edelson, R., "Photoreactivatible drugs", *TIPS,* 8, 138–143 (1987).
Star, W. M., "Light delivery and light dosimetry for photodynamic therapy", *Laser in Medical Science,* 5m 107–113 (1990).
Carruth, J. A. S.,"Clinical applications for photodynamic therapy", *J. Photochem Photobiol.,* 9, 396–397 (1991).
Kennedy, J. C. and Pottier, R. H., "Endogenous protoporphyrin IX, a clinical useful photosensitiser for photodynamic therapy", *J. Photochem Photobiol,* 14, 275–292 (1992).
Regula, J., Mac Roberts, A. J., Gorchein, A., Buonaccorsi, Thorpe, S. M., Spencer, G. M., Hartfield, A. R. W. and Brown, S. G. "Photosensitisation and photodynamic therapy of oesophageal, duodenal and colorectal tumours using 5–aminoleavulic acid induced protoporphyrin IX–a pilot study", *Gut,* 36, 67–75 (1995).
Bagshawe et al., *Antibody, Immunoconjugates, and Radiopharmaceuticals,* 4, 915–922 (1991).
Monks, A. et al., *Journal of National Cancer Institute,* 83, 757 (1991).
Thurston, D.E., "Advances in the study of Pyrrolo[2,1–c][4,1] benzodiazepine (PBD) Antitumour Antibiotics", *Molecular Aspects of Anticancer Drug–DNA interactions,* Neidle, S., Waring, M.J. eds., Macmillan Press Ltd., 1: 54–88 (1993).
Sagnou, M.J. et al., *Bioorganic & Medicinal Chemistry Letters,* 10, 2083–2086 (2000).
Baraldi, P.G., et al., "Synthesis, in Vitro Antiproliferative Activity, and DNA–Binding Properties of Hybrid Molecules Containing Pyrrolo[2,1–c][1,4]benzodiazepine and Minor–Groove–Binding Oligopyrrole Carriers", *J. Med. Chem.,* 42: 5131–5141 (1999).

\* cited by examiner

PYRROLOBENZODIAZEPINES

CROSS-REFERENCE TO RELATED APPLICATIONS

This application is a national stage entry under 35 U.S.C. §371 of PCT/GB99/02837, filed Aug. 27, 1994.

The present invention relates to pyrrolobenzodiazepines (PBDs), and is particularly concerned with the use of these compounds as prodrugs for antibody-directed enzyme-prodrug therapy (ADEPT), gene-directed enzyme-prodrug therapy (GDEPT), photodynamic therapy (PDT) and naturally present enzyme-prodrug therapy (NPEPT).

BACKGROUND TO THE INVENTION

Pyrrolobenzodiazepines (PBDs) have the ability to recognise and bond to specific sequences of DNA; the most preferred sequence is PuGPu (Purine-Guanine-Purine). The first PBD antitumour antibiotic, anthramycin, was discovered in 1965 (Leimgruber et al., 1965 *J. Am. Chem. Soc.,* 87, 5793–5795; Leimgruber et al., 1965 *J. Am. Chem. Soc.,* 87, 5791–5793). Since then, a number of naturally occurring PBDs have been reported, and over 10 synthetic routes have been developed to a variety of analogues (Thurston et al., 1994 *Chem. Rev.* 1994, 433–465). Family members include abbeymycin (Hochlowski et al., 1987 *J. Antibiotics,* 40, 145–148), chicamycin (Konishi et al., 1984 *J. Antibiotics,* 37, 200–206), DC-81 (Japanese Patent 58-180 487; Thurston et al., 1990, *Chem. Brit.,* 26, 767–772; Bose et al., 1992 *Tetrahedron,* 48, 751–758), mazethramycin (Kuminoto et al., 1980 *J. Antibiotics,* 33, 665–667), neothramycins A and B (Takeuchi et al., 1976 *J. Antibiotics,* 29, 93–96), porothramycin (Tsunakawa et al., 1988 *J. Antibiotics,* 41, 1366–1373), prothracarcin (Shimizu et al, 1982 *J. Antibiotics,* 29, 2492–2503; Langley and Thurston, 1987 *J. Org. Chem.,* 52, 91–97), sibanomicin (DC-102)(Hara et al., 1988 *J. Antibiotics,* 41, 702–704; Itoh et al., 1988 *J. Antibiotics,* 41, 1281–1284), sibiromycin (Leber et al., 1988 *J. Am. Chem. Soc.,* 110, 2992–2993) and tomamycin (Arima et al., 1972 *J. Antibiotics,* 25, 437–444). PBDs are of the general structure:

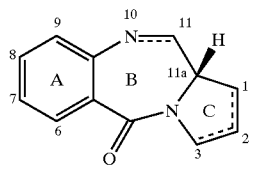

They differ in the number, type and position of substituents, in both their aromatic A rings and pyrrolo C rings, and in the degree of saturation of the C ring. In the B-ring there is either an imine (N═C), a carbinolamine (NH—CH(OH)) or a carbinolamine methyl ether (NH—CH (OMe))at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In *Antibiotics III.* Springer-Verlag, New York, pp. 3–11; Hurley and Needham-VanDevanter, 1986 *Acc. Chem. Res.,* 19, 230–237). Their ability to form an adduct in the minor groove enables them to interfere with DNA processing, hence their use as antitumour agents.

The use of prodrugs represents a very valuable clinical concept in cancer therapy. For example, a prodrug may be converted into an antitumour agent under the influence of an enzyme that is linked to a monoclonal antibody so that it can bind to a tumour associated antigen. The combination of such a prodrug with such an enzyme monoclonal antibody conjugate represents a very powerful therapeutic strategy. This approach to cancer therapy, often referred to as "antibody directed enzyme/prodrug therapy" (ADEPT) is disclosed in WO88/07378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, thereby converting the prodrug into the active drug within the tumour cells (Huber et al., *Proc. Natl. Acad. Sci. USA* (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, Annu. Rev. Biochem., 1993, 62;191. The term "GDEPT" (gene-directed enzyme prodrug therapy) is used to include both viral and non-viral delivery systems.

Photodynamic therapy (PDT) provides another method which uses prodrugs to deliver desired drugs to specific sites in the human body. Advances in the field of light delivery to internal areas of the body allow delivery to organs and other areas without the need for any extensive surgical procedures. The activation process can be extremely site specific, as the direction of a laser beam can be controlled with great precision, and the beam diameter can be reduced far below that of a single cell, minimising any possible damage to other neighbouring tissue from unwanted activation of the drug. The high energy of ultra-violet light (e.g. 350 nm equivalent to 340 kJ/mol) is sufficient to break a range of chemical bonds, since the bond energy spectrum of the majority of organic molecules lies between 250 and 420 kJ/mol. For example, there has been wide application of the photochemical deprotection of amino acids, peptides and polysaccharides from their o-nitrobenzyl carbamate, CBZ, and 4,5-dimethoxy-2-nitrobenzyl carbamate forms at wavelengths longer than 350 nm.

A further class of prodrugs is those where the protecting group is removed by an enzyme naturally present at the desired site of action. These enzymes include dopa-decarboxylase, L-γ-glutamyl transpeptidase, and mixed function oxidases and reductase (e.g. DT-diaphrase). This is method termed "naturally present enzyme-prodrug therapy (NPEPT) in this application. One enzyme of particular interest is glutathione transferase (GST), which forms part of a major cellular defence mechanism based on the use of the tripeptide, glutathione, as a scavenger of toxic electrophiles. GST acts as a catalyst in the reaction between glutathione and its target electrophiles. A consequence of this defence mechanism is the inactivation of electrophilic therapeutic agents. Many human tumour cells exhibit elevated GST levels compared to normal cells and the association of GST with resistance to DNA alkylating agents has been demonstrated by Lewis et al. (Carcinogenesis 1988, 9, 1283–1287), Kuzmich et al. (Journal of Biochemistry 1992, 281, 219–224), and Tew et al. (Glutathione-S-transferase and anti-cancer drug resistance, in Mechanism of Drug Resistance in Neoplastic Cells; Wooley, P. V., Tew, Kr. D., Eds.; Academic Press: Orlando, Fla., 1987; pp141–159). Chemotherapeutic agents that take advantage of this intrinsic property of cancer cells may prove highly useful in treating refractory cancers.

Prodrugs which make use of this elevated GST level have been made (Satyam et al., Med. Chem. 1996, 39, 1736–1747). They have a glutathione molecule linked via a 2-sulphonylethyloxycarbonyl linker to a phosphorodiamidate mustard. An alternative type of prodrug has made use of the closely related 2-phenylsulphonylethyloxycarbonyl (Psec) group (Nicolaou et al., Science, 1992, 256, 1172–1178). Such prodrugs showed selectivity between healthy human bone marrow cells and promeocytic and T cell leukemia tumour lines.

BRIEF SUMMARY OF THE INVENTION

A first aspect of the present invention provides a compound with the formula I:

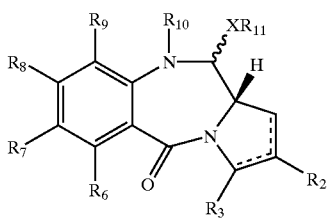

(I)

wherein:

$R_{10}$ is a therapeutically removable nitrogen protecting group;

$R_2$ and $R_3$ are independently selected from: H, R, OH, OR, =O, =CH—R, =CH$_2$, CH$_2$—CO$_2$R, CH$_2$—CO$_2$H, CH$_2$—SO$_2$R, O—SO$_2$—R, CO$_2$R, COR and CN;

$R_6$, $R_7$ and $R_9$ are independently selected from H, R, OH, OR, halo, amino, nitro, Me$_3$Sn; or R, and R, together form a group —O—(CH$_2$)$_p$—O—, where p is 1 or 2;

X is S, O or NH;

$R_{11}$ is either H or R;

where R is a lower alkyl group having 1 to 10 carbon atoms, or an aralkyl group (i.e. an alkyl group with one or more aryl substituents), preferably of up to 12 carbon atoms, whereof the alkyl group optionally contains one or more carbon-carbon double or triple bonds, which may form part of a conjugated system, or an aryl group, preferably of up to 12 carbon atoms; and is optionally substituted by one or more halo, hydroxy, amino, or nitro groups, and optionally contains one or more hetero atoms, which may form part of, or be, a functional group;

and where there is optionally a double bond between C1 and C2 or C2 and C3;

and $R_8$ is selected from H, R, OH, OR, halo, amino, nitro, Me$_3$Sn, where R is as defined above, or the compound is a dimer with each monomer being the same or different and being of formula I, where the $R_8$ groups of the monomers form together a bridge having the formula —T—R'—T— linking the monomers, where R' is an alkylene chain containing from 3 to 12 carbon atoms, which chain may be interrupted by one or more hetero atoms and/or aromatic rings, e.g. benzene or pyridine, and may contain one or more carbon-carbon double or triple bonds, and each T is independently selected from O, S or N.

If R is an aryl group, and contains a hetero atom, then R is a heterocyclic group. If R is an alkyl chain, and contains a hetero atom, the hetero atom may be located anywhere in the alkyl chain, e.g. —O—C$_2$H$_5$, —CH$_2$—S—CH$_3$, or may form part of, or be, a functional group, e.g. carbonyl, hydroxy.

R is preferably independently selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R groups are independently selected from a lower alkyl group having 1 to 10 carbon atoms optionally substituted by one or more halo, hydroxy, amino, or nitro groups. It is particularly preferred that R groups are unsubstituted straight or branched chain alkyl groups, having 1 to 10, preferably 1 to 6, and more preferably 1 to 4, carbon atoms, e.g. methyl, ethyl, propyl, butyl.

Alternatively, $R_6$, $R_7$, $R_8$, and $R_9$ may preferably be independently selected from R groups with the following structural characteristics:

(i) an optionally substituted phenyl group;

(ii) an optionally substituted ethenyl group;

(iii) an ethenyl group conjugated to an electron sink.

The term 'electron sink' means a moiety covalently attached to a compound which is capable of reducing electron density in other parts of the compound. Examples of electron sinks include cyano, carbonyl and ester groups.

The term 'therapeutically removable nitrogen protecting group' means any group which can protect the 10-nitrogen, but which is removable under therapeutic conditions in vivo, that is, removable under conditions which occur or can be caused to occur in vivo and are medically acceptable generally by elimination to produce a N10–C11 imine group or an equivalent, capable of interacting with DNA. The removal of the protecting group should leave the rest of the structure of the PBD unaffected.

Suitable removal techniques include applying light, e.g. with a wavelength of 250 to 400, or 550 nm, changing the ambient pH, or cleavage by the action of an enzyme. One particularly suitable enzyme is nitroreductase, although other suitable enzymes include penicillin V/G amidase, P-lactamase, phosphatase, L-γ-glutamyl transpeptidase, and α-galactosidase. The action of some of these enzymes is described in Jungheim, L. N. and Shepherd, T. A., Design of Antitumour Prodrugs: Substrates for Antibody Targeted Enzymes, Am. Chem. Soc. Chem. Rev., 1994, 94: 6, 1553–1566. Another particularly suitable enzyme is glutathionare transferase, as discussed above.

One possible group is $R_{10}$ of the formula II:

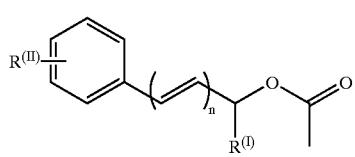

(II)

wherein n is 0 to 3, $R^{(I)}$ is H or R, and $R^{(II)}$ is one or more optional substituents independently selected from NO$_2$, OR, or R, where R is as defined in any of the definitions above; and if two substituents $R^{(II)}$ are on adjacent atoms, they may together be of the formula —O—(CH$_2$)$_m$—O—, where m is 1 or 2. $R^{(II)}$ is preferably NO$_2$.

If the therapeutically removable group $R_{10}$ is one which is susceptible to nitroreductase, it may be of the formula III:

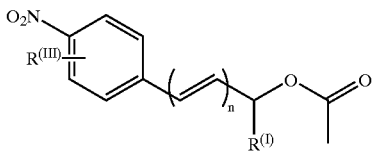

wherein n is 0 to 3, $R^{(I)}$ is H or R, and $R^{(III)}$ is one or more optional substituents independently selected from $NO_2$, OR or R, where R is as defined in any of the definitions above, and if two substituents $R^{(III)}$ are on adjacent atoms, they may together be of the formula $—O—(CH_2)_m—O—$, where m is 1 or 2.

Another possible therapeutically removable nitrogen protecting group, $R_{10}$, is of the formula XI:

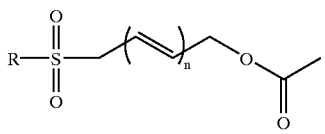

where R is as defined in any of the definitions above and n is 0 to 3, preferably 0. For this formula, R is most preferably a phenyl group, substituted or unsubstituted. This protecting group may be removable by the action of glutathione transferase (GST), which is present at high levels in many human tumour cells (see above).

It is preferred in compounds of formula I that X is O and, independently, that $R_{11}$ is H.

If there is a double bond in the C ring, it is preferably between C2 and C3.

Additionally, it is preferred that $R_6$ and $R_9$ are H, and further preferred that $R_7$ and $R_8$ are independently selected from H, OH, and OR. It is further preferred that $R_2$ and $R_3$ are H.

If the compound of formula I is a dimer, the dimer bridge may be of the formula $—O—(CH_2)_{p'}—O—$, where p' is from 1 to 12, preferably 3 to 9. Further, $R_6$ and $R_9$ are preferably H, and $R_7$ is preferably independently selected from H, OH, and OR.

A second aspect of the present invention provides a method of preparing a compound of formula I as described in the first aspect of the invention wherein $XR_{11} \neq OH$, from a corresponding compound Ia which is a compound of formula I in which $XR_{11}=OH$. A product in which $XR_{11}$ is OR may be prepared by direct etherification of compound Ia. A product in which X is S may be prepared by treatment of compound Ia with $R_{11}SH$ and a catalyst (generally a Lewis acid such as $Al_2O_3$). A product in which X is NH may be prepared by treatment of compound Ia with an amine $R_{11}NH$ and a catalyst (generally a Lewis acid such as $Al_2O_3$).

A third aspect of the present invention provides a method of preparing a compound of formula Ia as described in the second aspect of the invention, by the oxidation of a compound of formula IVa:

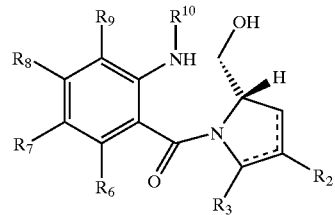

wherein the substituents of the compound of formula IVa are the same as for the compound of formula Ia to be prepared. (For preparation of dimeric compounds, the monomers linked through C8 by —T—R'—T— are both of formula IVa. Similar comments apply to other intermediates in dimer synthesis.) The preferred oxidation method is Swern oxidation.

A fourth aspect of the present invention provides a method of preparing a compound of formula IVa as described in the third aspect of the invention, by reacting a compound of formula Va:

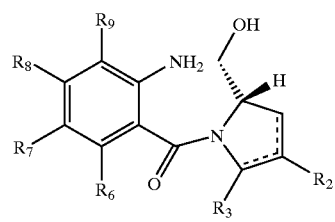

with a compound of formula VI:

$$Y—R_{10} \quad (VI)$$

wherein the substituents of the compounds of formulae Va and VI are the same as for the compound of formula IVa to be prepared, and Y is a halogen atom.

If the therapeutically removable nitrogen protecting group is to be of formula II, then it is preferred that the compound of formula VI is a haloformate of the formula VIa:

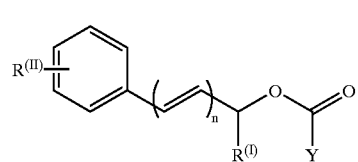

wherein the substituents are as defined for the group of formula II, and Y is a halogen atom.

If the therapeutically removable nitrogen group is to be of formula XI, then it is preferred that the compound of formula VI is a haloformate of the formula VIb:

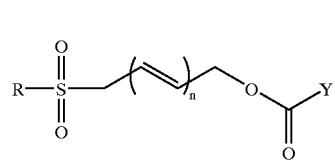

where Y is a halogen atom, and R and n are as defined for formula XI.

pA fifth aspect of the present invention provides an alternative synthesis of a compound of formula IVa as described in the third aspect of the invention, by reacting a compound of formula VII:

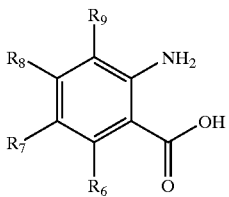

(VII)

with a compound of formula VI:

Y—R$_{10}$ (VI)

to form a compound of formula VIII:

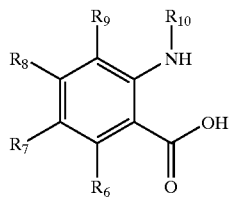

(VIII)

and then reacting the compound of formula VIII with a compound of formula IXa:

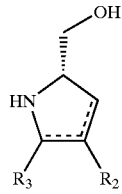

(IXa)

(e.g. by means of (COCl)$_2$), wherein the substituents for compounds of formulae VI, VII, VIII and IXa are the same as for the compound of formula IVa to be prepared, where Y is a halogen atom.

A sixth aspect of the present invention provides a method of preparing a compound of formula Ia as described in the second aspect of the invention, by the unmasking of a compound of formula IVb:

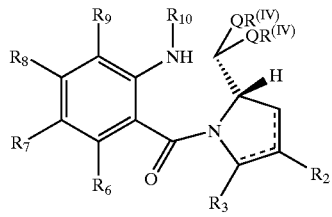

(IVb)

wherein the substituents of the compound of formula IVb are the same as for the compound of formula Ia to be prepared, and Q is either S or O and R$^{(IV)}$ are independently selected from Me or Et or may together form —(CH$_2$)$_q$— where q is 2 or 3. (For preparation of dimeric compounds, the monomers linked through C8 by —T—R'—T— are both of formula IVb. Similar comments apply to other intermediates in dimer synthesis.) The preferred unmasking method when Q=S is mercury-mediated unmasking. Unmasking when Q=O is preferably carried out by the use of acid conditions, e.g. TFA, methanol and water or palladium catalysis.

A seventh aspect of the present invention provides a method of preparing a compound of formula IVb as described in the sixth aspect of the invention, by reacting a compound of formula Vb:

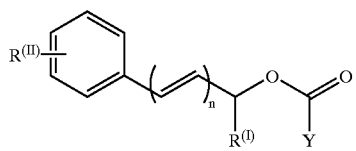

(Vb)

with a compound of formula VI:

Y—R$_{10}$ (VI)

wherein the substituents of the compounds of formulae Vb and VI are the same as for the compound of formula IVb to be prepared, and Y is a halogen atom.

If the therapeutically removable nitrogen protecting group is to be of formula II, then it is preferred that the compound of formula VI is a haloformate of the formula VIa:

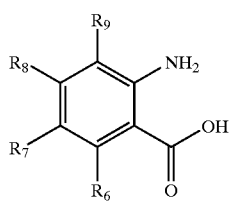

(VIa)

wherein the substituents are as defined for the group of formula II, and Y is a halogen atom.

An eighth aspect of the present invention provides an alternative synthesis of a compound of formula IVb as described in the second aspect of the invention, by reacting a compound of formula VII:

(VII)

with a compound of formula VI:

Y—R$_{10}$ (VI)

to form a compound of formula VIII:

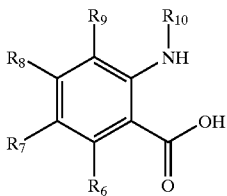
(VIII)

and then reacting the compound of formula VIII with a compound of formula IXb:

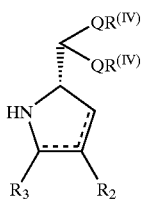
(IXb)

(e.g. by means of (COCl)$_2$), wherein the substituents for compounds of formulae VI, VII, VIII and IXb are the same as for the compound of formula IVb to be prepared, where Y is a halogen atom.

A ninth aspect of the present invention provides a method of making a compound of formula X:

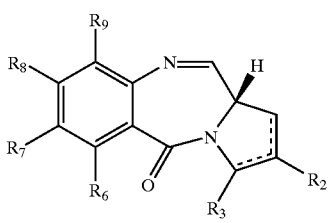
(X)

by cleavage of the therapeutically removable protecting group R$_{10}$ of a compound of formula I as described in the first aspect of the invention, wherein the substituent groups of the compound of formula X are the same as the substituent groups of the compound I used.

A tenth aspect of the present invention provides a use of a compound of formula I, wherein the therapeutically removable nitrogen protecting group (R$_{10}$) is enzyme labile, in conjunction with an appropriate enzyme in methods of ADEPT or GDEPT therapy. If the enzyme labile group is susceptible to nitroreductase, then compounds of formula I, may be used in conjunction with nitroreductase enzymes (for example, those isolated from *E. coli*) in methods of ADEPT and GDEPT therapy.

An eleventh aspect of the present invention provides a use of a compound of formula I, wherein the therapeutically removable nitrogen protecting group (R$_{10}$) is photolabile, in conjunction with light of wavelengths between 250 and 400 or 550 nm in methods of PDT.

A twelfth aspect of the invention provides a use for a compound of formula I, where the therapeutically removable nitrogen protecting group (R$_{10}$) is labile by conditions occurring naturally at specific localised sites in the patient in therapy. Suitable compounds of formula I may be those susceptible to a nitroreductase enzyme when used to treat hypoxic tumour cells, or those susceptible to enzymes which are naturally occurring at specific localised sites, such as glutathione transferase.

The drug produced by the cleavage of the therapeutically removable nitrogen protecting group, in either the tenth or eleventh or twelfth aspect of the invention, may be used for treating cancers or other site-specific diseases where a local increase of toxicity is beneficial to the patient. Cancers that may be treated are solid cancers including ovarian, colonic cancer, renal, breast and bowel CNS, melanoma, as well as leukemias. Such drugs may also be suitable for treating bacterial, viral or parasitic infections by exploiting a unique enzyme produced at the site of the infection which is not natural to the host, or by exploiting an elevation in the amount of an enzyme which does naturally occur in the host.

A thirteenth aspect of the present invention is a pharmaceutical composition comprising a compound of formula I as described in the first aspect of the invention. Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Capsules may comprise a solid carrier such as gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Solution, or Lactated Ringer's Injection. Preservatives, stabilisers, buffers, antioxidants and/or other additives may be included, as required.

A fourteenth aspect of the present invention provides the use of a compound of formula I as described in the first aspect of the invention, to prepare a medicament for the treatment of neoplastic disease or other site-specific diseases where a local increase of toxicity is beneficial to the patient. The compound of formula I may be provided together with a pharmaceutically acceptable carrier or diluent. The preparation of a medicament is described in relation to the thirteenth aspect of the invention.

BRIEF DESCRIPTION OF THE DRAWINGS

Aspects of the invention will now be further described with reference to the accompanying drawings in which.

DETAILED DESCRIPTION OF THE INVENTION

Preferred Synthetic Strategies

A key step in a preferred route to compounds of formula I is a cyclisation to produce the B-ring, involving generation of an aldehyde (or functional equivalent thereof) at what will be the 11-position, and attack thereon by the 10-nitrogen:

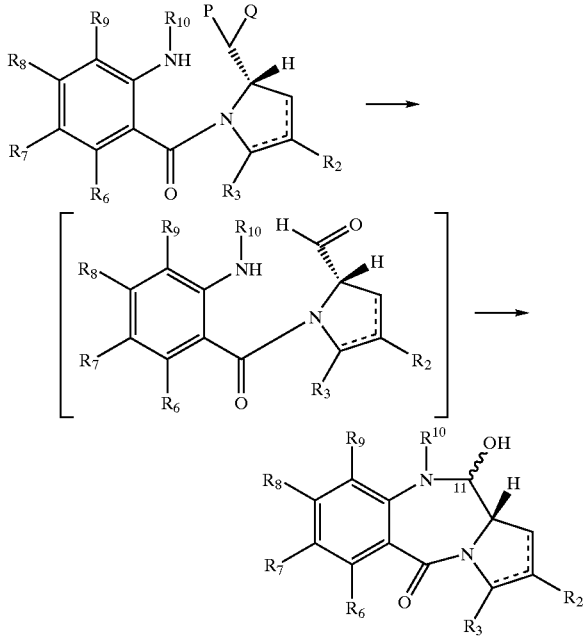

The "masked aldehyde", —CPQ, may be an acetal or thioacetal (e.g. P=Q=SEt or OMe), which may be cyclic, in which case the cyclisation involves unmasking. Alternatively, the masked aldehyde may be an aldehyde precursor, such as an alcohol, —CHOH, in which case the reaction involves oxidation, e.g. by means of TPAP or DMSO (Swern oxidation).

The masked aldehyde compound can be produced by condensing a corresponding 2-substituted pyrrolidine with a 2-nitrobenzoic acid:

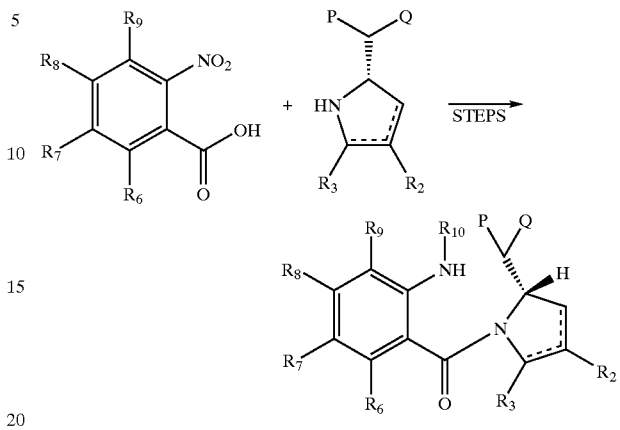

The nitro group can then be reduced to —$NH_2$ and protected by reaction with a suitable agent, e.g. a chloroformate, which provides the therapeutically removable nitrogen protecting group $R_{10}$ in the compound of formula I.

Figure 1:
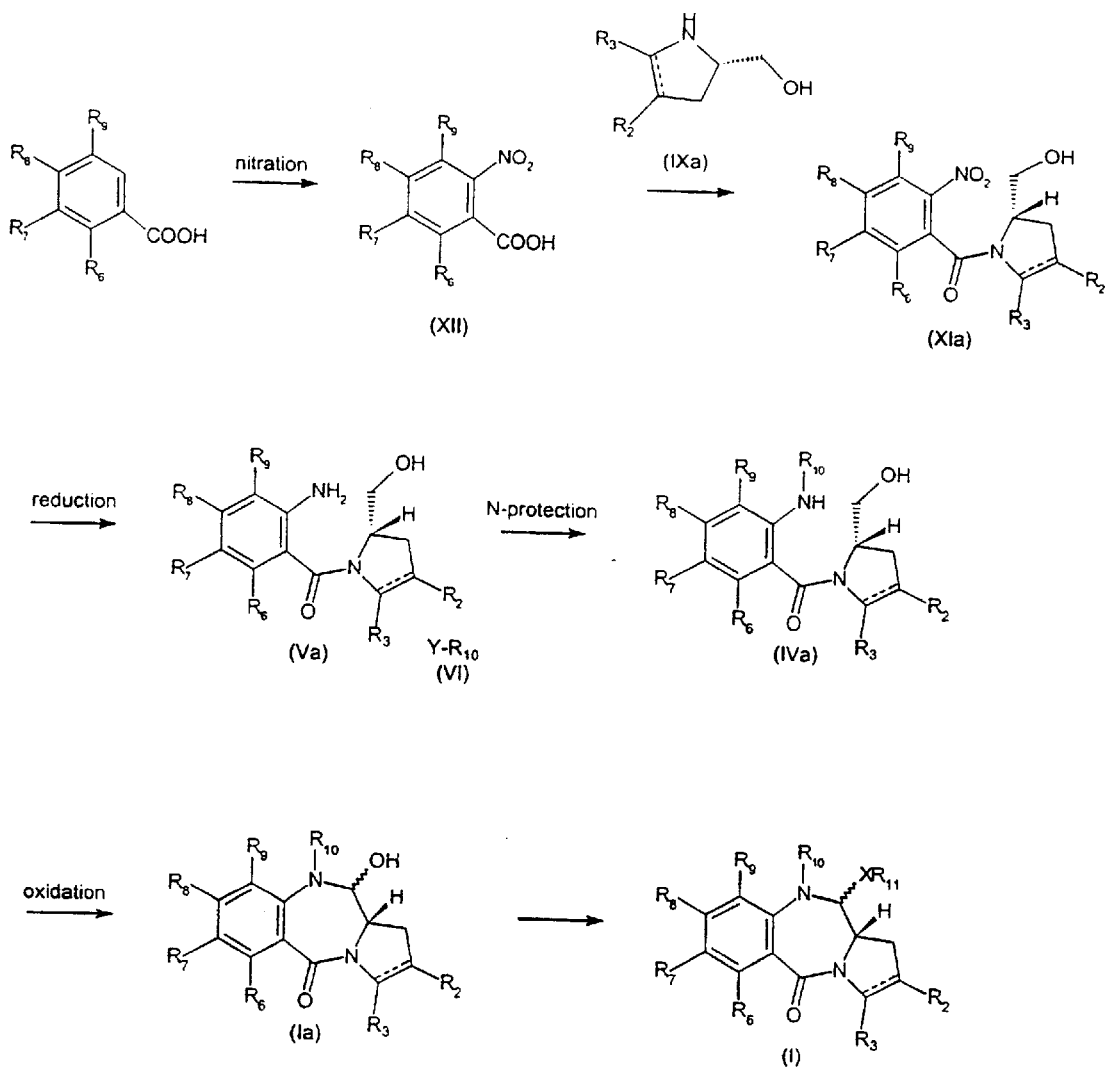
FIG. 1 is a synthesis scheme according to the present invention.

A process involving the oxidation-cyclization procedure is illustrated in FIG. 1 (an alternative type of cyclisation will be described later with reference to FIG. 3). If $R_{11}$ is other than hydrogen, the compound of formula I, may be prepared by direct etherification of the alcohol Ia. If X=S, and not O, the alcohol Ia, or the OR derivative, can be treated with $H_2S$, and a catalyst such as $Al_2O_3$, or by the addition of a thiol, e.g. EtSH. If X is NH then treatment of the alcohol Ia with the appropriate amine yields the desired compound of formula I.

Exposure of the alcohol (IVa) (in which the pro-10-nitrogen is generally protected as an amide carbamate) to tetrapropylammonium perruthenate (TPAP)/N-methylmorpholine N-oxide (NMO) over A4 sieves results in oxidation accompanied by spontaneous B-ring closure to afford the desired product. The TPAP/NMO oxidation procedure is found to be particularly convenient for small scale reactions while the use of DMSO-based oxidation methods, particularly Swern oxidation, proves superior for larger scale work (e.g. >1 g).

The uncyclized alcohol (IVa) may be prepared by the addition of a nitrogen protection reagent of formula VI, which is preferably a chloroformate or acid chloride, to the amino alcohol (Va), generally in solution, generally in the presence of a base such as pyridine (preferably 2 equivalents) at a moderate temperature (e.g. at 0° C.). Under these conditions little or no O-acylation is usually observed.

The key amino alcohol (Va) may be prepared by reduction of the [co]rresponding nitro compound (XIa), by choosing a method which will leave the rest of the molecule intact. Treatment of XIa with tin (II) chloride in a suitable solvent, e.g. refluxing methanol, generally affords, after the removal of the tin salts, the desired product in high yield.

Exposure of XIa to hydrazine/Raney nickel (or hydrogenation with a catalyst) avoids the production of tin salts and may result in a higher yield of Va, although this method is less compatible with the range of possible C and A-ring substituents. For instance, if there is C-ring unsaturation (either in the ring itself, or at $R_2$ or $R_3$), this technique may be unsuitable.

The nitro compound of formula XIa may be prepared by coupling the appropriate o-nitrobenzoyl chloride to a compound of formula IXa, e.g. in the presence of $K_2CO_3$ at −25°

C. under a $N_2$ atmosphere. The o-nitrobenzoyl chloride is synthesised from the o-nitro benzoic acid of formula XII—many of these are commercially available, and the synthesis of some examples has been reported by Althuis (Althuis, T. H. and Hess, H-J, 1977, Synthesis and Identification of the Major Metabolites of Prazosin Formed in Dog and Rat, *Journal of Medicinal Chemistry* 20, 1: 146–266). Compounds of formula IXa can be readily prepared, for example by olefination of the ketone derived from L-trans-hydroxy proline. The ketone intermediate can also be exploited by conversion to the enol triflate for use in palladium mediated coupling reactions such as the Heck, Stille and Suzuki reactions.

Dimer Synthesis (FIG. 2)

Figure 2A:
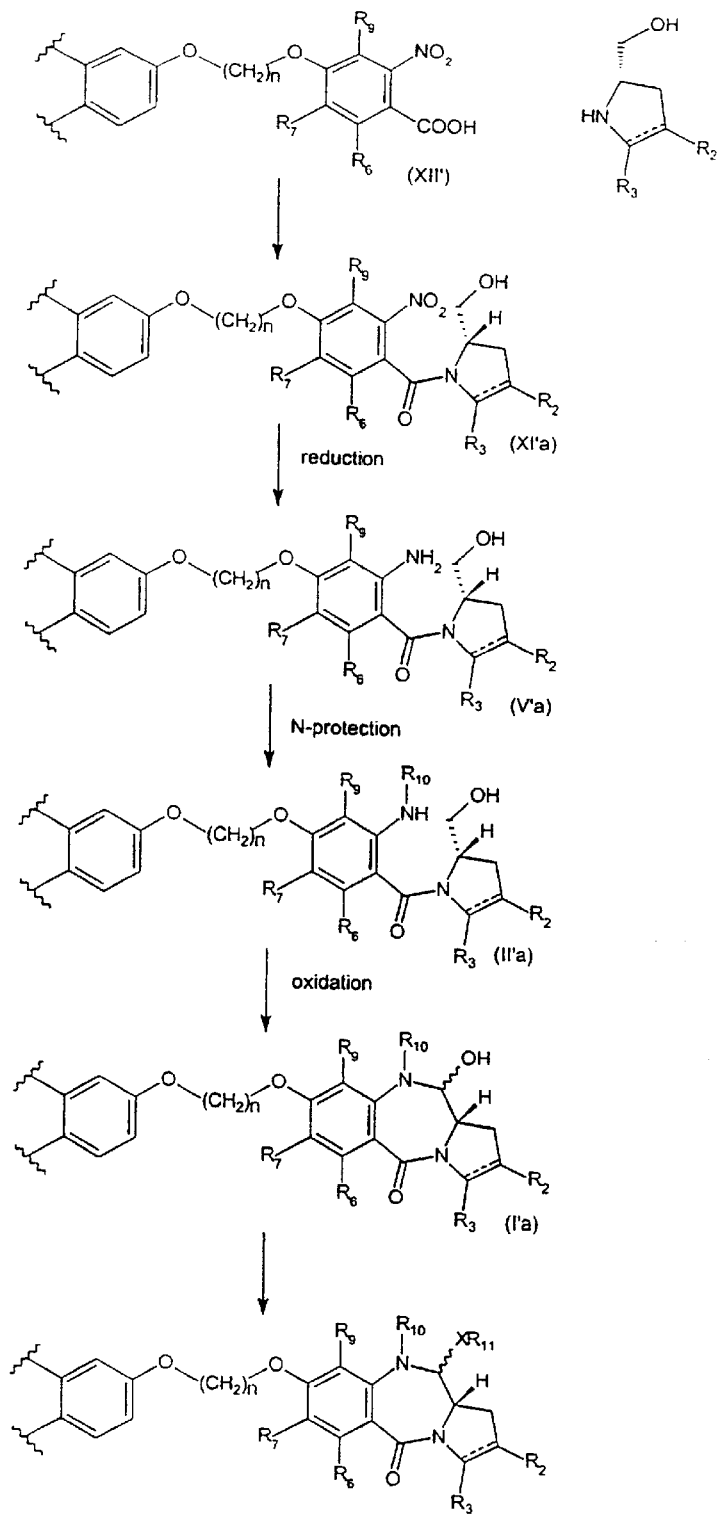
FIGS. 2a & 2b are a synthesis scheme for dimers according to the present invention.
Figure 2B:
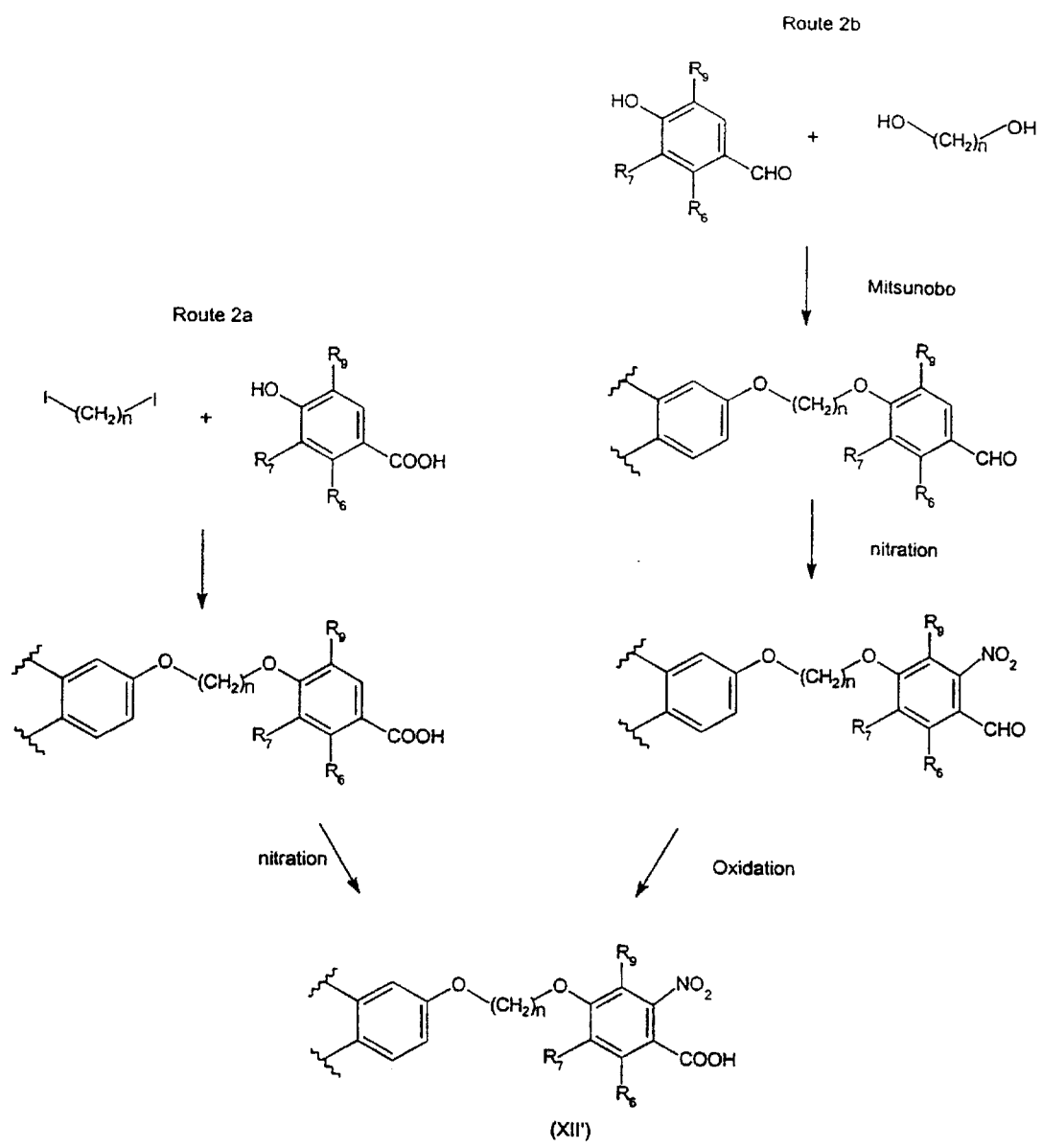

PBD dimers may be synthesized using the strategy developed for the synthesis of the protected PBD monomers (FIG. 2a). FIG. 2 also shows a synthesis route where the dimer linkage is of the formula —O—$(CH_2)_n$—O—. The step of dimer formation is normally carried out to form a bis(nitro acid) XII' (FIG. 2b).

The bis(nitro acid) XII' may be obtained by nitrating (e.g. using 70% nitric acid) the bis(carboxylic acid). This can be synthesised by alkylation of two equivalents of the relevant benzoic acid with the appropriate diiodoalkane under basic conditions (Route 2a). Many benzoic acids are commercially available and others can be synthesised by conventional methods.

An alternative synthesis of the bis(nitro acid) involves oxidation of the bis(nitro aldehyde), e.g. with potassium permanganate. This can be obtained in turn by direct nitration of the bis(aldehyde), e.g. with 70% $HNO_3$. Finally, the bis(aldehyde) can be obtained via Mitsunobu etherification of two equivalents of the benzoic aldehyde with the appropriate alkanediol (Route 2b).

Figure 3:
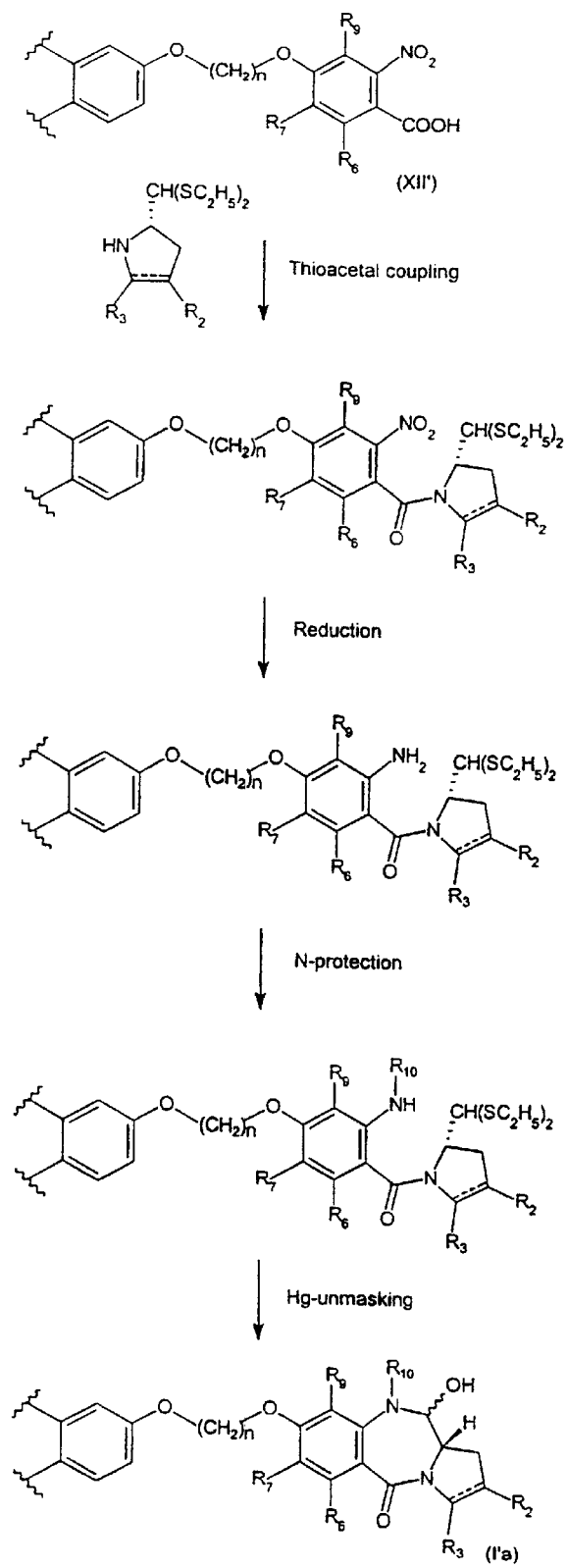
FIG. 3 is a synthesis scheme showing an alternative cyclisation, for use in the present invention.

Alternative Cyclisation (FIG. 3)

In FIGS. 1 and 2, the final or penultimate step is an oxidative cyclisation. An alternative, using thioacetal coupling unmasking, is shown in FIG. 3 (which shows it applied to a dimer, with a dimer linkage of formula —O—$(CH_2)_n$—O—). Mercury-mediated unmasking causes cyclisation to the desired compound (Ia').

The thioacetal compound may be prepared as shown in FIG. 3: the thioacetal protected C-ring [prepared via a literature method: Langley, D. R. & Thurston, D. E., *J. Organic Chemistry*, 52, 91–97 (1987)] is coupled to the bis(nitro carboxylic acid) core using a literature procedure. The resulting nitro compound cannot be reduced by hydrogenation, because of the presence of the thioacetal group, so the tin(II) chloride method is used to afford the bis(amine). This is then N-protected, e.g., by reaction with a chloroformate or acid chloride, such as p-nitrobenzylchloroformate.

An alternative to thioacetal coupling is the use of acetal coupling. The method is the same as that illustrated in FIG. 3, but with the thioacetal group replaced by an acetal group (e.g. —$CH(OMe)_2$). Acid or palladium-mediated unmasking is the preferred method of unmasking to cause cyclisation to the desired compound of formula Ia or I'a.

GDEPT

Vector Systems

In general, the vector for use in GDEPT therapies may be any suitable DNA or RNA vectors.

Suitable non-viral vectors include cationic liposomes and polymers. Suitable viral vectors include those which are based upon a retrovirus. Such vectors are widely available in the art. Huber et al. (ibid) report the use of amphotropic retroviruses for the transformation of hepatoma, breast, colon or skin cells. Culver et al. (Science (1992) 256; 1550–1552) also describe the use of retroviral vectors in GDEPT. Such vectors or vectors derived from them may also be used. Other retroviruses may also be used to make vectors suitable for use in the present invention. Such retroviruses include Rous sarcoma virus (RSV).

Englehardt et al. (Nature Genetics (1993) 4; 27–34) describe the use of adenovirus-based vectors in the delivery of the cystic fibrosis transmembrane conductance product (CFTR) into cells, and such adenovirus-based vectors may also be used. Vectors utilising adenovirus promoter and other control sequences may be of use in delivering a system according to the invention to cells in the lung, and hence useful in treating lung tumours.

Other vector systems including vectors based on the Molony murine leukaemia virus are known (Ram, Z et al., Cancer Research (1993) 53; 83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation codon ATG is supplied to direct efficient translation of the enzyme.

Suitable promoters which may be used in vectors described above, include MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

Other suitable promoters include tissue specific promoters, and promoters activated by small molecules, hypoxia or X-rays.

If nitroreductase is the enzyme of choice for the activation of compounds of formula I, then preferably the enzyme is a non-mammalian nitroreductase such as a bacterial nitroreductase. An *E. coli* nitroreductase as disclosed in WO93/08288 is particularly preferred. The enzyme may be modified by standard recombinant DNA techniques, e.g. by cloning the enzyme, determining its gene sequence and altering the gene sequence by methods such as truncation, substitution, deletion or insertion of sequences for example by site-directed mutagenesis. Reference may be made to "Molecular Cloning" by Sambrook et al. (1989, Cold Spring Harbor) for discussion of standard recombinant DNA techniques. The modification made may be any which still leaves the enzyme with the ability to reduce the nitro group in suitable compounds of formula I, but alters other properties of the enzyme, for example its rate of reaction or selectivity.

In addition, small truncations in the N- and/or C-terminal sequence may occur as a result of the manipulations required to produce a vector in which a nucleic acid sequence encoding the enzyme is linked to the various other vector sequences.

For information on the use of penicillin V/G amidase, and β-lactamase in GDEPT, see Jungheim, L. N. and Shepherd, T. A., Design of Antitumour Prodrugs: Substrates for Antibody Targeted Enzymes, Am. Chem. Soc. Chem. Rev., 1994, Vol 94, No. 6, 1553–1566.

ADEPT

For applications in ADEPT systems, an antibody directed against a tumour specific marker is linked to the relevant enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, e.g. as described in EP-A-239400.

The antibodies may be produced by conventional hybridoma techniques or, in the case of modified antibodies or fragments, by recombinant DNA technology, e.g. by the expression in a suitable host vector of a DNA construct encoding the modified antibody or fragment operably linked to a promoter. Suitable host cells include bacterial (eg. *E. coli*), yeast, insect and mammalian cells. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

DT

The activation process in PDT can be highly site specific. The direction of a laser beam can be controlled with great precision, and the beam diameter can be reduced to a width far below that of a single cell. Therefore, it can act upon a very limited area, minimising damage to neighbouring tissue.

Ultra-violet light is sufficient to break a range of chemical bonds since the energy spectrum for bond breakage for the majority of organic molecules lies between 250 and 420 kJ/mol, and, for example, 350 nm is equivalent to 340 kJ/mol. For example, a broad range of light-mediated deprotection reactions have been demonstrated including the photochemical deprotection of amino acids, peptides and polysaccharides from their CBZ and o-nitrobenzyl and 4,5-dimethoxy-2-nitrobenzyl carbamate forms at wavelengths longer than 350 nm, (Pillai, R. V. N., Photoremovable protecting groups in organic chemistry, *Synthesis* (1980), 1–26), (Bayley, H., Gasparro, F. and Edelson, R., Photoactivatible drugs, *TIPS* (1987) 8, 138–143, (Star, W. M., Light delivery and light dosimetry for photodynamic therapy, Laser in Medical *Science* (1990) 5, 107–113. On the other hand, highly reactive and thus cytotoxic species can also result from relatively low energy activations. For example, a reactive excited state of molecular oxygen, the singlet state, differs in only 90 kJ/mol from its ground triplet state. However, this enables sufficient concentrations of the toxic species to be formed by those sensitisers which absorb at wavelengths longer than 600 nm, (Carruth, J. A. S., Clinical applications for photodynamic therapy, *J Photochem Photobiol* (1991) 9, 396–397).

The main limitation of this approach arises from the physics of light itself and its interaction with human tissue. The ability of light to penetrate tissue has been found to be wavelength-dependent. Penetrating ability increases with increasing wavelength but limitations arise due to light scattering and reflection. In biological tissues the scattering coefficient, for example of red light, is much greater than the absorption coefficient, (Carruth, J. A. S., Clinical applications for photodynamic therapy, *J Photochem Photobiol* (1991) 9, 396–397), (Kennedy, J. C. And Pottier, R. H, Endogenous protoporphyrin IX, a clinical useful photosensitiser for photodynamic therapy, *J Photochem Photobiol* (1992) 14, 275–292). As a result, photons entering the tissue are scattered several times before they are either absorbed or diffused. Although this might be expected to increase the energy delivered to certain areas, internal reflection results in an exponential decrease of energy flux with increasing distance from the tissue-air interface. These limitations have been partially overcome in the treatment of relatively bulky tumours or when deeper penetration is necessary by the use of multiple interstitial optical fibres.

Several tumour types have been identified as potential targets for PDT. They include head and neck tumours, carcinomas of the bronchus, malignant brain tumours, superficial tumours of the bladder and vascular disease, which have all shown promising responses in the clinic, (Regula, J., Mac Roberts, A. J., Gorchein, A., Buonaccorsi, Thorpe, S. M., Spencer, G. M., Hartfield, A. R. W. and Bown, S. G., Photosensitisation and photodynamic therapy of oesophageal, duodenal and colorectal tumours using 5-aminoleavulic acid induced protoporphyrin IX-a pilot study, *Gut* (1995) 36, 67–75).

The technique of PDT as discussed above can be used in combination with appropriate compounds of formula I when the therapeutically removable nitrogen protecting group is photolabile. The preferred wavelength of UV light used is 250 to 400 or 550 nm.

Applications of the Invention

Compounds of the invention can be used in vitro or in vivo for a range of applications. For example, a number of vector systems for the expression of nitroreductase in a cell have been developed. The further development of such systems (e.g. the development of promoters suitable for specific cell types) requires suitable candidate prodrugs capable of killing cells when activated by nitroreductase. Prodrug compounds of formula I susceptible to nitroreductase may be used in such model systems.

The model systems may be in vitro model systems or in vivo xenograft model systems comprising for example human tumour cells implanted in nude mice. Compounds of formula I susceptible to different enzymes may be used in similar systems which have been appropriately modified.

Compounds of formula I which are not activatable by an enzyme may be tested in vitro with other suitable forms of activation against panels of different tumour cell types to determine efficacy against such tumour cells. The efficacy of compounds of the invention against a range of tumour cell types may be used as points of reference for the development of further antitumour compounds. Compounds of formula I may also be tested in combination with additional anti-cancer compounds to determine potential combination drug systems, for example combinations which are synergistic.

Compounds of formula I may also be used in a method of treatment of the human or animal body. Such treatment includes a method of treating the growth of neoplastic cells in a patient with neoplastic disease which comprises administering to a patient in need of treatment compounds of formula I as part of an ADEPT, GDEPT or PDT system or treatment with compounds of formula I alone, where neoplastic diseases include leukaemia and solid tumours such as ovarian, colonic, lung, renal, breast, bowel, CNS and melanomas. The treatment can also be the treatment of other site-specific diseases where local increase in toxicity is beneficial to the patient.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including its metastases. Such measures can be effective in prolonging and/or enhancing the quality of life and relieving the symptoms of the disease.

Therapies

Methods of ADEPT and GDEPT will now be described with reference to nitroreductase, although other enzymes as previously described could be substituted with appropriate modifications to the methods described.

The basis of PDT has been described above, but the information on the administration of products below also applies to this type of therapy. This information is also relevant to therapies where the prodrug is activated by conditions naturally occurring within the body (e.g. hypoxia, elevated level of GST see discussion of NPEPT above).

ADEPT Therapy

The antibody/enzyme conjugate for ADEPT can be administered simultaneously but it is often found preferable, in clinical practice, to administer the enzyme/antibody conjugate before the prodrug, e.g. up to 72 hours or even 1 week before, in order to give the enzyme/antibody conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour. In this way, the premature release of the compound produced by the action of the nitroreductase on the prodrugs of the present invention is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to part of the conjugate so as to inactivate the enzyme in the blood and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition, or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be designed for use and administered such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably from about 10 to about 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable co-factor for the enzyme. Suitable co-factors may include a riboside or ribotide of nicotinic acid or nicotinamide.

The antibody/enzyme conjugate may be administered by any suitable route usually used in ADEPT therapy. This includes parenteral administration of the antibody in a manner and in formulations similar to that described below.

GDEPT Therapy

For use of the vectors in therapy, the vectors will usually be packaged into viral particles and the particles delivered to the site of the tumour, as described in for example Ram et al. (supra). The viral particles may be modified to include an antibody, fragment thereof (including a single chain) or tumour-directed ligand to enhance targeting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. Viruses, for example isolated from packaging cell lines, may also be administered by regional perfusion or direct intratumoral injection, or direct injection into a body cavity (intracaviterial administration), for example by intra-peritoneal injection.

The exact dosage regime for GDEPT will, of course, need to be determined by individual clinicians for individual patients and this, in turn, will be controlled by the exact nature of the prodrug and the cytotoxic agent to be released from the prodrug. However, some general guidance can be given. Chemotherapy of this type will normally involve parenteral administration of modified virus, and administration by the intravenous route is frequently found to be the most practical.

In GDEPT systems the amount of virus or other vector delivered will be such as to provide a similar cellular concentration of enzyme as in the ADEPT system mentioned above. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably from about 10 to about 100 mg/Kg per patient per day.

Administration of Prodrugs

While it is possible for the compounds of formula I to be administered alone, it is preferable to present them as pharmaceutical formulations, for use with any of the above methods. The formulations comprise the compounds, together with one or more acceptable carriers thereof and optionally other therapeutic ingredients, or diluents. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy) propyl]-N,N,N-triethylammonium (DOTMA), those comprising dioleoylphosphatidylethanolamine (DOPE), and those comprising 33[N-(n'N'-dimethylaminoethane)-carbamoyl]cholesterol (DC-Chol).

Formulations suitable for parenteral or intramuscular administration include aqueous and non-aqueous sterile injection solutions which may contain anti-oxidants, buffers, bacteriostats, bacteriocidal Antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of a sterile liquid carrier, for example Water for Injection, immediately prior to use. Injection solutions and suspensions may be prepared extemporaneously from sterile powders, granules and tablets of the kind previously described.

It should be understood that in addition to the ingredients particularly mentioned above, the formulations may include other agents conventional in the art having regard to the type of formulation in question. Of the possible formulations, sterile pyrogen-free aqueous and non-aqueous solutions are preferred.

The doses may be administered sequentially, eg. at hourly, daily, weekly or monthly intervals, or in response to a specific need of a patient. Preferred routes of administration are oral delivery and injection, typically parenteral or intramuscular injection or intratumoural injection. For methods of PDT dermal or topical administration may be preferred, e.g. subcutaneous injection or creams and ointments, and such methods of administration are well known.

The exact dosage regime will, of course, need to be determined by individual clinicians for individual patients and this, in turn, will be controlled by the exact nature of the compound of formula I, but some general guidance can be given. Typical dosage ranges generally will be those described above which may be administered in single or multiple doses. Other doses may be used according to the condition of the patient and other factors at the discretion of the physician.

EXAMPLES

Embodiments of the present invention will now be described in detail by way of example.
General Experimental Methods Melting points (mp) were determined on a Gallenkamp P1384 digital melting point apparatus and are uncorrected. Infrared (IR) spectra were recorded using a Perkin-Elmer 297 spectrophotometer. $^1$H- and $^1$C-NMR spectra were recorded on a Jeol GSX 270 MHZ FT-NMR spectrometer operating at 20° C.+/−1° C. Chemical shifts are reported in parts per million (δ) downfield from tetramethylsilane (TMS). Spin multiplicities are described as: s (singlet), bs (broad singlet), d (doublet), dd (doublet of doublets), t (triplet), q (quartet), p (pentuplet) or m (multiplet). Mass spectra (MS) were recorded using a Jeol JMS-DX 303 GC Mass Spectrometer (EI mode: 70 eV, source 117–147° C.). Accurate molecular masses (HRMS) were determined by peak matching using perfluorokerosene (PFK) as an internal mass marker, and FAB mass spectra were obtained from a glycerol/thioglycerol/trifluoroacetic acid (1:1:0.1) matrix with a source temperature of 180° C. Optical rotations at the Na-D line were obtained at ambient temperature using a Perkin-Elmer 141 Polarimeter. Flash chromatography was performed using Aldrich flash chromatography "Silica Gel-60" (E. Merck, 230–400 mesh). Thin-layer chromatography (TLC) was performed using $GF_{254}$ silica gel (with fluorescent indicator) on glass plates. All solvents and reagents, unless otherwise stated, were supplied by the Aldrich Chemical Company Ltd. and were used as supplied without further purification. Anhydrous solvents were prepared by distillation under a dry nitrogen atmosphere in the presence of an appropriate drying agent, and were stored over 4A molecular sieves or sodium wire. Petroleum ether refers to the fraction boiling at 60–80° C.

Example 1

Synthesis of a nitroreductase-activated benzyl DC-81 prodrug for ADEPT (7)

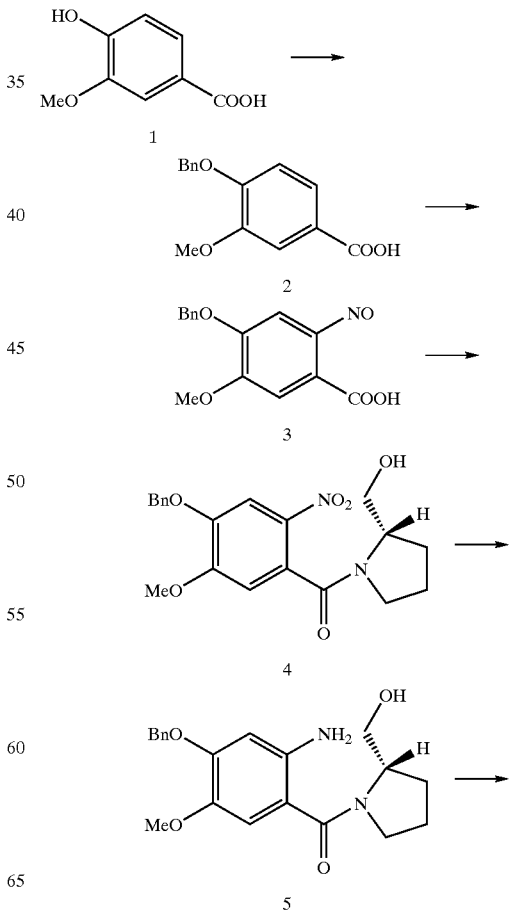

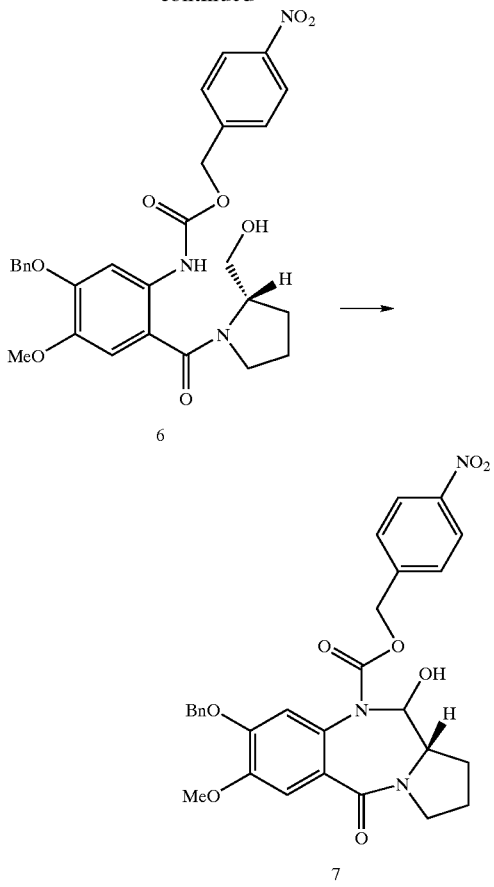

Synthesis of 4-Benzyloxy-3-methoxybenzoic acid (2)

A solution of benzyl chloride (24.6 ml, 209 mmol, 1.1 eq.) in THF (100 ml) was added dropwise at 0° C. over 15 min, to a mechanically stirred solution of 4-hydroxy-3-methoxybenzoic acid (vanillic acid, 1) (30 g, 179 mmol) in THF (90 ml) and 2.0 M aq. NaOH (225 ml). The mixture was allowed to warm to room temperature and then heated under reflux for 48 hours. After cooling, the mixture was washed with hexane (2×100 ml) and the THF was removed in vacuo. The remaining aqueous phase was acidified to pH 1 with conc. HCl. The resulting precipitate was collected by filtration, washed with water and dried to afford 4-benzyloxy-3-methoxybenzoic acid (2) as a pale amorphous solid.

Yield (after recrystallisation from EtOAc) 31 g (67%); mp 171–172° C; IR (cm$^{-1}$) 3700–3200, 2820–3000, 2210, 2140, 1670, 1600, 1580, 1510, 1450, 1430, 1410, 1380, 1340, 1300, 1265, 1220, 1180, 1130–1110, 1030, 1010; $^1$H NMR (CDCl$_3$+DMSO-d$_6$) δ 7.60 (d, J=2 Hz, 1H), 7.55 (d, J=2 Hz 1H), 7.30–7.44 (m, 5H), 6.90 (d, J=8.4 Hz, 1H), 5.19 (s, 2H), 3.91 (s, 3H); $^{13}$C NMR (CDCl$_3$+DMSO-d$_6$) δ 168.3, 151.7, 148.8, 136.3, 128.5, 128.0, 127.2, 123.7, 123.5, 112.5, 112.2, 70.6, 55.9; MS (EI) (m/z, relative intensity) 258 (M$^+$, 20), 91 (100), 79 (3), 65 (10), 51 (3); EI-HRMS m/z 258.0949 (calc'd for C$_{15}$H$_{14}$O$_4$ m/z 258.0892).

Synthesis of 4-Benzyloxy-5-methoxy-2-nitrobenzoic acid (3)

Method A: A freshly prepared mixture of SnCl$_4$ (5 g, 19.5 mmol) and fuming nitric acid (1.67 g, 26.5 mmol) was added dropwise over 5 minutes to a mechanically stirred solution of 2 (4.35 g, 17 rmmol) in DCM at −25° C. (dry ice/carbon tetrachloride). The mixture was maintained at the same temperature for a further 15 min, quenched with water (150 ml), and allowed to warm to room temperature After the organic layer was separated, the aqueous layer was extracted with EtOAc (2×75 ml). The combined organic phase was dried (MgSO$_4$) and evaporated in vacuo to afford a light brown gum which was recrystallised to form 3 as pale yellow needles. Yield=4.16 g (82%)

Method B: 4-benzyloxy-3-methoxybenzoic acid (8.5 g, 32.9 mmol) was added in small portions over 30 minutes to stirred solution of 70% nitric acid (100 ml). When addition was complete the reaction mixture was allowed to warm to 15° C. and maintained at that temperature for a further 30 min. The reaction mixture was then poured onto ice and the resultant precipitate was collected by filtration, washed with ice-cold water and dried to afford the nitrated product 3 as a yellow powder.

Yield (after recrystallisation from EtOAc/hexane) 7.8 g (78%); mp 182≧185° C.; IR (cm$^{-1}$) 3400–3200, 2820–2930, 1670, 1600, 1580, 1550, 1510, 1450, 1410, 1400, 1370, 1350, 1330, 1265, 1210, 1160, 1160, 1055, 1005; $^1$H-NMR (CDCl$_3$+DMSO-d$_6$) δ 7.36–7.45 (m, 6H), 7.16 (s, 1H), 5.19 (s, 2H), 3.95 (s, 3H); $^{13}$C-NMR (CDCl$_3$+DMSO-d$_6$) δ 167.3, 152.7, 149.0, 140.9, 135.2, 128.4, 127.6, 127.3, 111.1, 71.2, 56.5; MS (EI) (m/z, relative intensity) 303 (M$^+$, 64), 286 (36), 273 (5), 259 (5), 181 (7), 123 (8), 105 (13), 91 (100), 77 (8), 65 (63), 51 (23); EI-HRMS m/z 303.0824 (calc'd for C$_{15}$H$_{13}$NO$_6$ m/z 303.0743).

Synthesis of (2S)-N-(4-benzyloxy-5-methoxy-2-nitrobenzoyl)pyrrolidine-methanol (4)

A catalytic amount of DMF (3 drops) was added to a solution of 4-benzyloxy-5-methoxy-2-nitrobenzoic acid (3) (3.5 g, 11.55 mmol) and oxalyl chloride (1.75 g, 13.56 mmol, 1.2 eq) in dry acetonitrile (30 ml). The solution was allowed to stir under nitrogen overnight. The resulting acid chloride solution was then added dropwise over 30 minutes to a stirred suspension of pyrrolidinemethanol (1.168 g, 11.56 mmol, 1 eq) and K$_2$CO$_3$ (3.675 g, 26.63 mmol, 2.3 eq) in acetonitrile (80 ml) at −25° C. under a nitrogen atmosphere. The reaction mixture was stirred at the same temperature for a further 1 hour and then allowed to return to room temperature and quenched with water (200 ml). The solution was then extracted with chloroform (4×100 ml) and the combined organic phase was washed with 1M HCl (2×50 ml), water (2×75 ml), brine (2×50 ml) and water (100 ml), dried (MgSO$_4$) and the solvent was evaporated in vacuo to afford a light yellow oil. The product was further purified by means of flash chromatography (5% MeOH/CHCl$_3$) to afford (4) as a pale yellow oil which slowly crystallised on standing.

Yield 3.92 g (88%); [α]$^{20}_D$: −62.3° (c 0.45, CHCl$_3$); IR (cm$^{-1}$) 3500–3250, 2860, 2910, 1600, 1580, 1520, 1455, 1430, 1370, 1330, 1275, 1220, 1210, 1185, 1150, 1110, 1060, 1025, 1000; $^1$H-NMR (CDCl$_3$) δ 7.76 (s, 1H), 7.34–7.47 (m, 5H), 6.83 (s, 1H), 5.21 (s, 2H), 4.38–4.40 (bs, 1H), 3.98 (s, 3H), 3.80–3.95 (m, 2H), 3.15–3.20 (m, 2H), 2.17–2.21 (m, 2H), 1.69–1.89 (m, 2H); $^{13}$C-NMR (CDCl$_3$) δ 155.0, 148.1, 136.9, 135.2, 128.8, 128.5, 127.9, 127.6, 109.2, 109.1, 71.3, 66.1, 61.5, 56.8, 49.5, 28.4, 24.4; MS (EI) (m/z, relative intensity) 386 (M$^+$, 4), 368 (6), 355 (39), 286 (90), 121 (4), 91 (100), 65 (4); EI-HRMS m/z 386.1531 (calc'd for C$_{20}$H$_{22}$N$_2$O$_6$ m/z 386.1478).

Synthesis of (2S)-N-(2-amino-4-benzyloxy-5-methoxybenzoyl)pyrrolidine-methanol (5)

Method A: A solution of the nitro compound (4) (1.4 g, 3.62 mmol) and $SnCl_2.2H_2O$ (4.58 g, 20.08 g, 5.5 eq) in methanol (70 ml) was heated at reflux for 45 min. The solvent was removed by evaporation in vacuo and the resulting brown oil was diluted with EtOAc (150 ml), treated with sat. aq. $NaHCO_3$ (150 ml) and allowed to stir under $N_2$ overnight. The resulting suspension was filtered through Celite, the organic phase was then separated and washed with brine (2×100 ml), dried ($MgSO_4$) and the excess solvent was finally evaporated in vacuo. The residual light brown oil was further purified by column chromatography (5% $MeOH/CHCl_3$) to afford the amine (5) as a bright yellow oil. Yield=0.82 g (62%).

Method B: Hydrazine hydrate (4.53 g, 90.67 ml, 5 eq) was added dropwise to a solution of the nitro compound 4 (7.0 g, 18.13 mmol) in dry methanol (20 ml) and a catalytic amount of Raney Ni (0.544 g) over antibumping granules whilst a gently reflux was maintained The mixture was heated at reflux for a further 15 minutes when TLC (5% $MeOH/CHCl_3$) indicated that the reaction had gone to completion. The Ni catalyst was then removed by filtration through Celite and the solvent removed by evaporation in vacuo. The product was further purified by flash chromatography (5% $MeOH/CHCl_3$) to afford the amine 5 as a bright yellow unstable oil which required storage at low temperature.

Yield 5.2 g (81%); $[\alpha]^{20}_D$: −15.94 (c 0.13, $CHCl_3$); $^1$H-NMR ($CDCl_3$) δ 7.28–7.42 (m, 5H), 6.76 (s, 1H), 6.26 (s, 1H), 5.09 (s, 2H), 4.37–4.42 (bs, 1H), 3.78 (s, 3H), 3.58–3.77 (m, 4H), 2.04–2.10 (m, 2H), 1.69–1.92 (m, 2H); $^{13}$C-NMR ($CDCl_3$) δ 171.8, 151.0, 141.2, 136.5, 128.6, 127.6, 127.1, 112.9, 102.9, 70.6, 66.8, 60.9, 57.1, 51.0, 28.5, 24.9; IR (cm$^{-1}$) 3500–3100, 2950, 1680, 1620, 1590, 1510, 1450, 1425, 1400, 1330, 1260, 1230, 1170, 1165, 1130, 1100, 1080, 1055, 1030; MS (EI) (m/z, relative intensity) 356 (M$^+$, 100), 256 (68), 237 (14), 226 (4), 164 (6), 138 (15), 100 (8), 91 (96), 84 (22), 65 (8); EI-HRMS m/z 356.1785 (calc'd for $C_{20}H_{24}N_2O_4$ m/z 356.1736).

Synthesis of (2S)-N-[2-(p-nitrobenzyloxy)carboxamido-4-benzyloxy-5-methoxybenzoyl]pyrrolidinemethanol (6)

A solution of 4-nitrobenzyl chloroformate (0.6 g, 2.8 mmol, 1 eq) in dry DCM (15 ml) was added dropwise over 20 minutes to a solution of the amine (5) (1 g, 2.8 mmol) and pyridine (0.44 g, 5.6 mmol, 2 eq) in dry DCM (20 ml) at 0° C. under $N_2$. After the addition was complete the solution was allowed to stir under for a further 1.5 hours. The reaction mixture was then washed with sat. aq. $CuSO_4$ (2×100 ml), water (150 ml), brine (100 ml), dried ($MgSO_4$) and the excess solvent removed under vacuum. The resulting oil was subjected to flash chromatography (3% $MeOH/CHCl_3$) to afford the protected amine (6) as a pale yellow oil.

Yield 1.16 g (77%); IR (cm$^{-1}$) 3500–3100, 2950, 1680, 1620, 1590, 1510, 1450, 1425, 1400, 1330, 1260, 1230, 1170, 1165, 1130, 1100, 1080, 1055, 1030; $^1$H-NMR (CDCl, rotamers) δ 9.04 (s, 1H), 8.20 (d, J=2 Hz, 2H), 7.81 (s, 1H), 7.28–7.55 (m, 5H), 6.86 (s, 1H), 5.14–5.24 (bs, 4H), 4.39 (bs, 1H), 3.82 (s, 3H), 3.55–3.89 (m, 4H), 2.04–2.14 (m, 2H), 1.70–1.87 (m, 2H); $^{13}$C-NMR ($CDCl_3$) δ 170.7, 153.2, 150.3, 147.5, 143.6, 136.1, 128.7–127.7, 123.7, 111.5, 106.0, 70.6, 65.2, 60.9, 56.5, 51.7, 28.2, 25.1; MS (FAB) (m/z, relative intensity) 535 (MH$^+$, 4), 435 (2), 356 (3), 256 (9), 192 (2), 185 (4), 166 (3), 136 (13), 120 (5), 102 (26), 91 (100), 84 (5).

Synthesis of (11aS)-8-benzyloxy-7-methoxy-1,2,3,10,11,11a-hexahydro-11-hydroxy-10-(p-nitrobenzyloxy)carboxy-5H-pyrrolo[2,1-c][1,4]-benzodiazepine-5-one (7)

A solution of the carbamate 6 (0.4 g, 0.75 mmol), NMO (0.131 g, 1.12 mmol, 1.5 eq) over 4 Å molecular sieve (0.375 g) in a solvent mixture of dry DCM:$CH_3CN$ (9:3 ml) was allowed to stir at room temperature under nitrogen for 15 min. A portion of TPAP (13 mg) was then added and the solution was allowed to stir for a further 2 hours. TLC (2% $MeOH/CHCl_3$) indicated that reaction incomplete and a further amount of NMO (65 mg, 0.845 mmol, 0.75 eq) and TPAP (6.5 mg) was added. After 15 min, TLC indicated a complete loss of starting material. The molecular sieve was removed by filtration through Celite and the solvent was removed under reduced pressure. The black residue was purified by column chromatography (1% MeOH/$CHCl_3$ followed by EtOAc:Petroleum ether, 95:5) to afford the cyclised final product 7.

Yield 0.124 (31%); IR (cm$^{-1}$) 3600–3200, 2820–3000, 1710, 1600, 1510, 1450, 1430, 1400, 1370, 1350, 1305, 1270, 1220, 1120–1100, 1050, 1030, 1010; $^1$H-NMR ($CDCl_3$, rotamers) δ 8.10 (d, J=8.43 Hz, 2H), 7.27–7.53 (m, 6H), 7.20 (d, J=8.4 Hz, 2H), 6.70 (s, 1H), 5.62 (d, J=10.2 Hz, 1H), 5.07 (d, J=10.7 Hz, 4H), 3.94 (s, 3H), 3.52–3.72 (m, 3H), 2.04–2.10 (m, 4H); $^{13}$C-NMR ($CDCl_3$) δ 166.83, 149.26, 142.85, 136.03, 128.79–127.17, 126.38, 114.58, 112.53, 111.00, 105.92, 86.23, 71.12, 66.21, 59.90, 56.21, 47.32, 46.42, 28.68, 23.05; MS (FAB) (m/z, relative intensity) 535 (M$^+$+2, 2), 353 (6), 337 (10), 286 (5), 256 (3), 241 (2), 228 (2), 192 (3), 136 (7), 91 (100); EI-HRMS m/z 533.1813 (calc'd for $C_{28}H_{27}N_3O_8$ m/z 533.1798).

Example 2

Synthesis of a Benzyl Dc-81 prodrug for the PGA ADEPT (9)

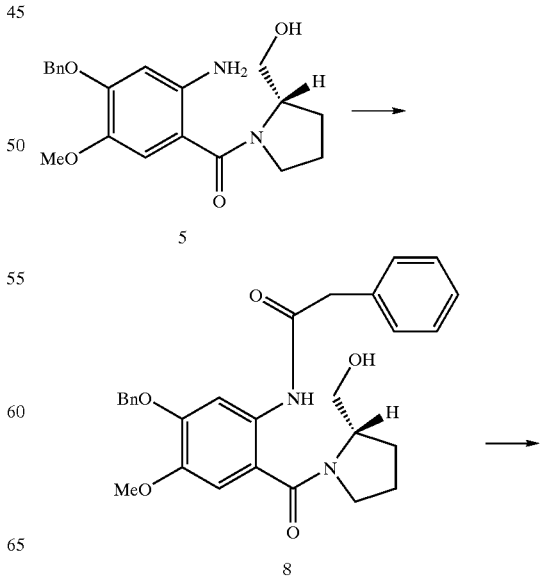

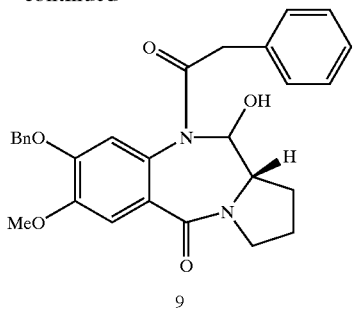

9

Synthesis of (2S)-N-[2-phenyl acetamido-4-benzyloxy-5-methoxybenzoyl]pyrrolidine methanol (8)

A catalytic amount DMF(4 drops) was added to a solution of phenyl acetic acid (0.42 g, 3.3 mmol, 1.2 eq) and oxalyl chloride (0.51 g, 3.96 mmol, 1.4 eq) in dry acetonitrile (10 ml) and the reaction mixture was allowed to stir overnight under nitrogen. The resulting acid chloride was added dropwise over 20 minutes to a mixture of the amine (5)(1 g, 2.8 mmol) and $K_2CO_3$ (0.97 g, 7.02 mmol, 2.5 eq) in dry acetonitrile (60 ml) at −25° C. under $N_2$. The reaction mixture was allowed to stir for a further 2 hours at −25° C. and then allowed to warm to room temperature. The reaction mixture was diluted with water (200 ml) and it was extracted with $CHCl_3$ (4×100 ml). The combined organic phase was washed with 1M HCl (2×50 ml), water (2×75 ml) and brine (100 ml) and dried over $MgSO_4$. The solvent was removed under vacuum and the residual oil was further purified by flash chromatography (5% $MeOH/CHCl_3$) to afford the phenylacetamide (8) as a pale oil.

Yield 0.91 g (68%); IR ($cm^{-1}$) 3400, 2093, 1660, 1613, 1519, 1495, 1454, 1435, 1401, 1345, 1262, 1218, 1175, 1101, 1028, 1003, 969; $^1$H-NMR ($CDCl_3$, rotamers) δ 9.27 (s, 1H), 7.90 (s, 1H), 7.26–7.48 (m, 10H), 6.77 (s, 1H), 5.11 (s, 2H), 4.19–4.29 (bs, 1H), 3.78 (s, 3H), 3.65 (s, 2H), 3.35–3.60 (m, 4H), 1.81–2.08 (m, 2H), 1.62–1.81 (m, 2H); $^{13}$C-NMR ($CDCl_3$) δ 169.8, 149.9, 145.0, 136.2, 134.5, 129.3–127.3, 110.9, 107.8, 70.6, 66.2, 61.2, 56.5, 51.2, 44.8, 28.3, 24.9; MS (EI) (m/z, relative intensity) 474 ($M^+$, 7), 374 (44), 284 (7), 256 (9), 228 (3), 166 (9), 105 (14), 102 (25), 91 (100), 84 (5); EI-HRMS m/z 474.2142 (calc'd for $C_{28}H_{30}N_2O_5$ m/z 474.2155).

Synthesis of (11aS)-8-benzyloxy-7-methoxy-1,2,3,11,11a-pentahydro-11-hydroxy-10-phenylacetyl-5H-pyrrolo[2,1-c][1,4]-benzodiazepine-5-one (9)

A solution of the phenylacetamide (8) (0.5 g, 1.05 mmol) and NMO (0.184 g, 1.57 mmol, 1.5 eq) over molecular sieve (0.525 g) in a solvent system consisting of dry DCM and $CH_3CN$ (9:3 ml) was allowed to stir for 15 minutes at room temperature under nitrogen. TPAP (19 mg, 5% molar) was then added and the mixture was stirred for 1 hour when TLC (5% $MeOH/CHCl_3$) indicated complete consumption of starting material. The reaction mixture was filtered and evaporated in vacuo. The product was further purified by flash chromatography (2% $MeOH/CHCl_3$) to afford the protected PBD 9 as an opaque oil.

Yield 0.15 g (30%); $[\alpha]^{20}_D$: +13250 (c 0.04, $CHCl_3$); IR ($cm^{-1}$) 3400, 2956, 2927, 2094, 1631, 1553, 1514, 1454, 1433, 1407, 1379, 1352, 1278, 1219, 1202, 1181, 1136, 1067, 1009, 752; $^1$H-NMR ($CDCl_3$, rotamers) δ 7.19–7.38 (m, 11H), 6.47 (s, 1H), 5.76 (d, J=10.1 Hz, 1H), 4.87 (d, J=12.1 Hz, 2H), 3.95 (s, 3H), 3.42–3.67 (m, 3H), 2.62 (s, 2H), 1.98–2.11 (m, 4H); $^{13}$C-NMR ($CDCl_3$) δ 173.56, 166.54, 149.74, 135.81, 134.84, 130.94–126.56, 114.77, 111.45, 84.38, 70.60, 59.87, 56.28, 46.41, 28.54, 22.67; MS (EI) (m/z, relative intensity) 472 ($M^+$, 40), 374 (25), 352 (15), 326 (6), 284 (7), 136 (5), 91 (100), 70 (17); EI-HRMS m/z 472.1944 (calc'd for $C_{28}H_{28}N_2O_5$ m/z 472.1998).

Example 3

Synthesis of a photolabile Benzyl DC-81 prodruq (11)

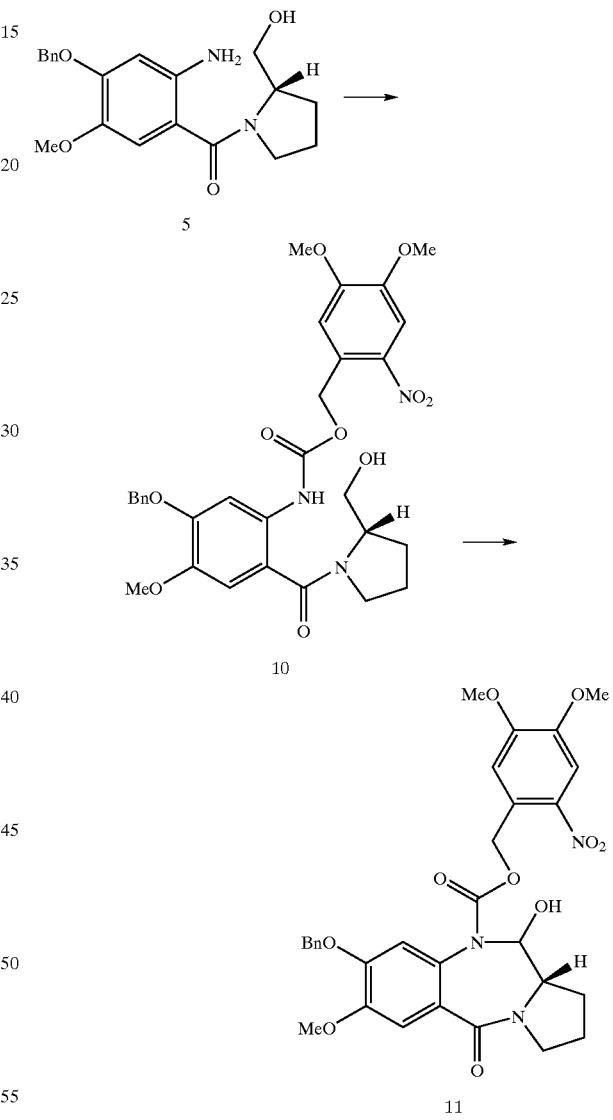

Synthesis of (2S)-N-[2-(21-nitro-4',5'-dimethoxybenzyloxy)carboxamido-4-benzyloxy-5-methoxybenzoyl]pyrrolidinemethanol (10)

A solution of 4,5-dimethoxy-2-nitrobenzyl chloroformate (NVOC-Cl) (0.77 g, 2.8 mmol, 1 eq) in dry DCM (10 ml) was added dropwise over 15 minutes to a solution of the amine (5) (1 g, 2.8 mmol) and pyridine (0.44 g, 5.6 mmol, 2 eq) in dry DCM at 0° C. under $N_2$. The reaction mixture was then stirred at 0° C. for a further 2.5 hours when TLC (3% MeOH/CHCl₃) indicated completion of the reaction. The solution was then washed with aq. sat. CuSO₄ (2×75 ml), water (2×100 ml), brine (150 ml) and dried over MgSO₄. The excess solvent was removed under reduced pressure to give the crude product. Further purification by column chromatography (5% MeOH/CHCl₃) afforded 10 as a yellow oil.

Yield 1.45 g (87%); $[\alpha]^{20}{}_D$: −175.5° (c 0.225, CHCl₃); IR (cm⁻¹) 4330, 4253, 3428, 2924, 2854, 1711, 1626, 1513, 1463, 1377, 1266, 1216, 1173, 761, 722; ¹H-NMR (CDCl₃, rotamers) δ 8.90 (s, 1H), 7.82 (s, 1H), 7.73 (s, 1H), 7.26–7.47 (m, 6H), 6.85 (s, 1H), 5.58 (d, J=15 Hz, 2H), 5.16 (s, 2H), 4.29–4.39 (bs, 1H), 3.95–3.99 (s, 6H), 3.84 (s, 3H), 3.49–3.72 (m, 4H), 1.86–2.17 (m, 2H), 1.72–1.86 (m, 2H); ¹³C-NMR (CDCl₃) δ 153.7, 153.2, 150.4, 148.1, 144.5, 139.6, 136.1, 128.5, 128.1, 127.8, 127.6, 111.5, 110.8, 109.9, 108.1, 70.7, 66.4, 63.7, 62.7, 61.0, 56.7–56.4, 51.6, 28.3; MS (FAB) (m/z, relative intensity) 596 (M⁺1, 16), 356 (6), 256 (19), 196 (95), 181 (21), 166 (20), 149 (14), 102 (32), 91 (100), 87 (10), 73 (44), 61 (22), 57 (31).

Synthesis of (11aS)-8-benzyloxy-7-methoxy-1,2,3,10,11,11a-hexahydro-11-hydroxy-10-(21-nitro-4',5'-dimethoxybenzyloxy)carboxy-5H-pyrrolo[2,1-c][1,4]-benzodiazepine-5-one (11)

A solution of the NVOC protected amine, 10 (0.4 g, 0.67 mmol) and NMO (0.236 g, 20.17 mmol, 3 eq) over molecular sieve (0.335 g) in a mixture of dry DCM:CH₃CN (9:3 ml) was allowed stir for 15 minutes at room temperature under N₂. TPAP (23 mg, 10% molar) was then added to the reaction mixture and it was allowed to stir for a further 2 hours when the reaction was found to be complete by TLC (2% MeOH/CHCl₃). The molecular sieve was removed by filtration through Celite and the resulting solution was evaporated in vacuo. The resulting dark oil was subjected to flash chromatography (1% MeOH/CHCl₃) to give the photolabile protected PBD (11).

Yield 0.21 g (49%); $[\alpha]^{20}{}_D$: 212.5° (c 0.08, CHCl₃); IR (cm⁻¹) 4329, 4258, 3405, 2925, 2361, 1713, 1620, 1602, 1579, 1514, 1463, 1377, 1342, 1277, 1219, 1103, 1065, 1012, 968, 870, 791, 722; ¹H-NMR (CDCl₃, rotamers) δ 7.66–7.71 (s, 1H), 7.11–7.39 (m, 6H), 6.80–6.92 (s, 1H), 6.32 (s, 1H), 5.14–5.67 (m, 5H), 3.85–4.15 (m, 9H), 3.49–3.67 (m, 3H), 2.01–2.15 (m, 4H); ¹³C-NMR (CDCl₃) δ 170.41, 166.73, 194.97, 149.03, 135.92, 128.67–126.30, 124.52, 114.64, 112.24, 110.87, 109.82, 108.92, 107.97, 86.02, 71.51, 66.38, 65.03, 60.40, 56.48–56.19, 46.67, 28.70, 26.41, 23.65, 21.05; IR (cm⁻¹) 3600–3100, 3020, 2400, 2105, 1765, 1640, 1525, 1430, 1385, 1350, 1310, 1280, 1215, 1170, 1110, 1045; MS (FAB) (m/z, relative intensity) 594 (MH⁺, 9), 353 (5), 337 (4), 282 (6), 256 (4), 241 (8), 196 (100), 180 (15), 166 (16), 151 (13), 136 (6), 123 (5), 105 (17), 91 (98); EI-HRMS m/z 593.2010 (calc'd for C₃₀H₃₁N₃O₁₀ m/z 593.2042).

Example 4

Synthesis of a Benzyl tomaymycin prodrug for nitroreductase ADEPT (147)

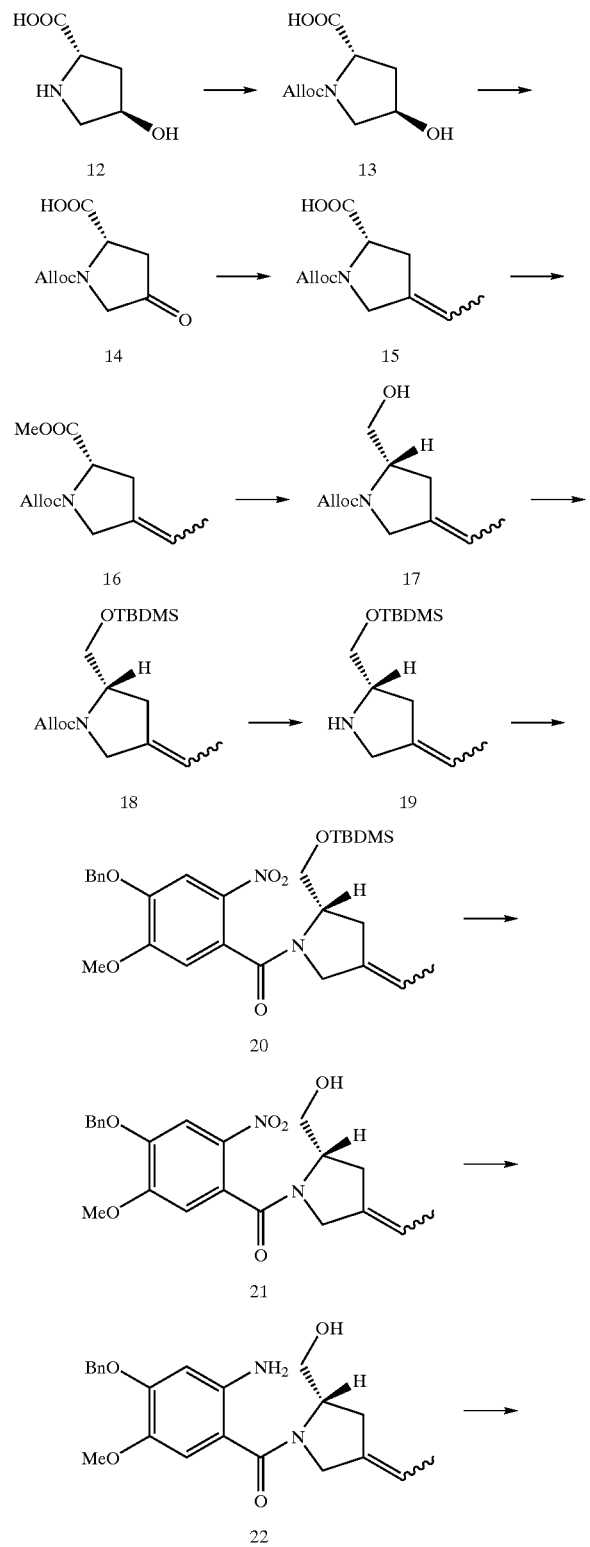

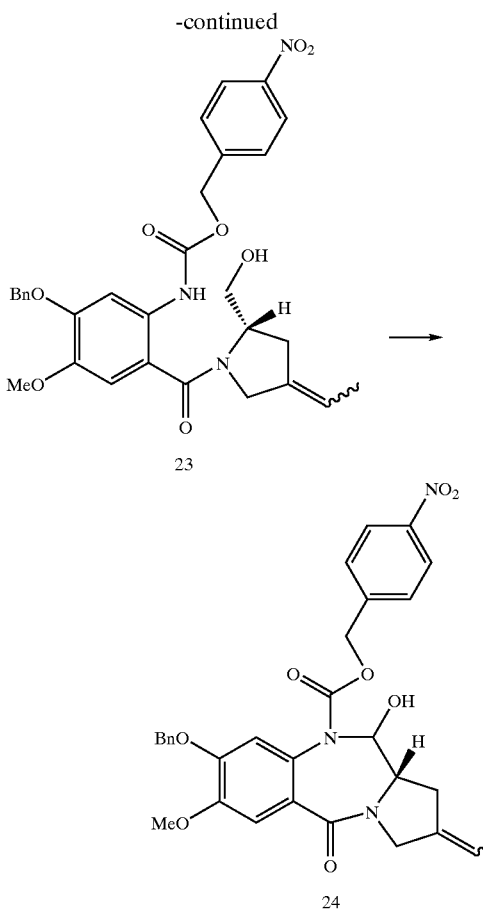

23

24

Synthesis of (2S,4S)-N-(Allyloxycarbonyl)-4-hydroxypyrrolidine-2-carboxylic acid (13)

A solution of allyl chloroformate (33.17 g, 275 mmol, 1.2 eq) in THF (30 ml) was added dropwise over 30 minutes to a suspension of trans-4-hydroxy proline (30 g, 229 mmol) in THF (150 ml) and water (150 ml) at pH 9 (adjusted with 4M NaOH) and at 0° C. The reaction mixture was allowed to stir at 0° C. and pH 9 for a further 1 hour. The aqueous layer was separated and saturated with NaCl, washed with EtOAc (4×100 ml) and the pH of the aqueous phase was adjusted to 2 with conc. HCl. The resulting oil was extracted with EtOAc(3×100 ml). The combined organic phase was dried (MgSO$_4$) and evaporated in vacuo to afford the Alloc protected hydroxy proline (13), as a thick transparent oil which was used for the next stage without further purification.

Yield 41 g (84%); [α]$^{20}_D$: −236° (c 0.25, CHCl$_3$); IR (cm$^{-1}$) 3429, 2522, 2340, 2258, 2130, 1688, 1437, 1415, 1345, 1277, 1222, 1177, 1133, 1085, 1047, 1025, 994, 827, 768; $^1$H-NMR (CDCl$_3$, rotamers) δ 5.80–5.99 (m, 1H), 5.13–5.34 (m, 2H), 4.52–4.63 (m, 2H), 4.37–4.44 (m, 2H), 3.53–3.60 (m, 2H), 2.00–2.36 (m, 2H); $^{13}$C-NMR (CDCl) δ 174.7, 174.5, 154.8, 154.5, 132.8, 132.7, 117.1, 116.7, 69.2, 68.5, 65.7, 65.6, 57.9, 57.6, 54.9, 54.4, 38.9, 38.2; MS (EI) (m/z, relative intensity) 215 (M$^+$, 14), 170 (100), 130 (95), 126 (34), 108 (35), 68 (51), 56 (21); EI-HRMS m/z 215.0759 (calc'd for C$_9$H$_{13}$NO$_5$ m/z 215.0743).

Synthesis of (2S)-N-(Allyloxycarbonyl)-4-oxopyrrolidine-2-carboxylic acid (14)

The alloc protected hydroxy proline (13) (18 g, 83.72 mmol) was dissolved in acetone (1260 ml). The Jone's reagent [Cro$_3$:26.6 g/H$_2$SO$_4$:21.3 ml and the solution was made up to 100 ml with water] (87 ml) was added over 10 min. The resulting mixture was stirred for a further 45 minutes when the excess oxidant was quenched with methanol (15 ml). The green chromium salts were removed by filtration through Celite and the filtrate was diluted in CHCl$_3$(1000 ml). The combined organic phase was washed with brine several times (5×500 ml) and the solvent was evaporated under reduced pressure, to yield the ketone 14 which was used without any purification.

Yield 14.68 (82%); IR (cm$^{-1}$) 3471, 3020, 2932, 2610, 2041, 1761, 1691, 1649, 1547, 1411, 1343, 1266, 1195, 1164, 1128, 972, 939, 877, 759; $^1$H-NMR (CDCl$_3$, rotamers) δ 9.20 (bs, 1H), 5.86–6.00 (m, 1H), 5.21–5.35 (m, 2H), 4.87–4.91 (m, 2H), 4.87–4.91 (m, 1H), 3.87–3.99 (s, 2H), 2.68–2.95 (m, 2H); $^{13}$C-NMR (CDCl$_3$) δ 207.6, 207.1, 175.8, 175.3, 155.3, 154.2, 131.9, 118.4, 118.2, 67.0, 66.8, 55.8, 52.5, 52.3, 41.0, 40.3; MS (EI) (m/z, relative intensity)=213 (M$^+$, 19), 168 (81), 152 (8), 128 (100), 112 (15), 100 (37), 96 (36), 68 (14), 58 (13), 56 (37); EI-HRMS m/z 213. 0641 (calc'd for C$_9$H$_{11}$NO$_5$ m/z 213.0637).

Synthesis of (2S)-(E,Z)-N-(Allyloxycarbonyl)-4-ethylidenepyrrolidine-2-carboxylic acid (15)

A mixture of NaH (60% suspension) (4 g, 100 mmol, 4 eq) and ethyl triphenylphosphonium bromide (37 g, 100 mmol, 4 eq) in freshly distilled THF (250 ml) was refluxed for 4 hours under nitrogen. A solution of the ketone 14 (5.325 g, 25 mmol) in freshly distilled THF (50 ml) was added dropwise over 40 minutes and the reaction mixture was refluxed overnight under nitrogen. It was then cooled and poured into a 5 % w/v aq. solution of NaHCO$_3$ (500 ml) and stirred for 10 min. The mixture was then washed with EtOAc (2×250 ml). The aqueous layer was acidified to pH 3 with dil. HCl (vigorous effervescence was observed). The emulsion was extracted with EtOAc (4×200 ml) and the combined organic phase was washed with brine (250 ml) and dried (MgSO$_4$). The solvent was then evaporated in vacuo to give an orange oil which was used in the next stage without further purification. Crude yield 3.81 g (68%)

Synthesis of Methyl-(2S)-(E,Z)-N-(Allyloxycarbonyl)-4-ethylidenepyrrolidine-2-carboxylate (16)

Oxalyl chloride and DMF (4 drops) was added to a solution of the Wittig product 15 (3.5 g, 16 mmol) in dry toluene (15 ml) and it was stirred overnight at room temperature and under N$_2$. Freshly distilled methanol (20 ml) was then added and the mixture was stirred for a further 4 hours when TLC (EtOAc:Petroleum ether, 1:1) revealed complete loss of starting material. The solvent was then evaporated in vacuo. The resulting oil was dissolved in EtOAc (60 ml) and the solution was washed with sat. aq. NaHCO, (4×25 ml), brine (50 ml), dried (MgSO$_4$) and the solvent was removed under reduced pressure to afford the esterified Wittig product (16).

Yield 3.48 g (94%); [α]$^{20}_D$: −377.7° (c 0.045, CHCl$_3$); IR (cm$^{-1}$) 4214, 3452, 3019, 2955, 2862, 2400, 1746, 1704, 1649, 1437, 1410, 1343, 1310, 1274, 1215, 1179, 1120, 1072, 1029, 991, 932, 755; $^1$H-NMR (CDCl$_3$, rotamers) δ 5.83–6.00 (m, 1H), 5.16–5.48 (m, 3H), 4.56–4.68 (m, 3H), 4.05–4.14 (s, 2H), 3.87–3.99 (m, 3H), 2.53–2.97 (m, 2H), 1.60–1.63 (m, 3H); $^1$C-NMR (CDCl$_3$) (E/Z isomers) δ 172.9, 154.8, 134.1, 134.0, 133.1, 133.0, 132.8, 132.7, 118.2, 118.1, 117.8, 117.7, 117.5, 117.4, 117.1, 66.1, 66.0, 65.9, 58.8, 58.6, 58.4, 52.3, 51.1, 50.6, 48.3, 47.7, 36.6, 35.7, 32.6, 31.7, 14.7, 14.6, 14.4; MS (EI) (m/z, relative intensity) 239 (M+, 4), 180 (70), 154 (100), 136 (55), 94 (33), 80 (10), 67 (19), 59 (8); EI-HRMS m/z 239.1030 (calc'd for $C_{12}H_{17}NO_4$ m/z 239.1158).

Synthesis of (2S)-(E,Z)-N-(Allyloxycarbonyl)-4-ethylidenepyrrolidinemethanol (17)

A solution of the Alloc protected C-Ring ester (16) (2.5 g, 10.46 mmol) was dissolved in freshly distilled THF (50 ml) and stirred under nitrogen at 0° C. Lithium borohydride (0.4 g, 17.95 mmol, 1.7 eq) was added slowly and in small portions to that solution (effervescence was observed). The mixture was allowed to warm to room temperature and stirred for a further 4 hours when the reaction was complete as it was indicated by TLC (EtOAc:Petroleum ether, 1:1). It was then cooled back down to 0° C. and the reaction was stopped by the addition of water (40 ml) dropwise over 15 min. The mixture was neutralised with 2M HCl (40 ml) which was added very slowly and vigorous effervescence occurred. It was then extracted with EtOAc (3×100 ml), the combined organic phase was washed with water (150 ml) and brine (100 ml), dried ($MgSO_4$) and the solvent was removed under reduced pressure to afford an oil which was further purified by flash chromatography (EtOAc:Petroleum ether, 60:40) to give the pure product 17.

Yield 1.57 g (71%); IR (cm$^{-1}$) 3425, 2947, 2864, 2085, 1678, 1547, 1536, 1411, 1349, 1308, 1236, 1203, 1114, 1047, 975, 931, 883, 851, 769; $^1$H-NMR ($CDCl_3$, rotamers) δ 5.87–6.01 (m, 1H), 5.19–5.40 (m, 3H), 4.59–4.61 (s, 2H), 3.64–4.15 (m, 5H), 2.37–2.80 (m, 2H), 1.62–1.64 (m, 3H); $^{13}$C-NMR ($CDCl_3$) (E/Z isomers) δ 156.3, 154.5, 133.1, 132.8, 131.8, 131.7, 130.9, 130.7, 128.7, 128.6, 125.5, 117.5–115.9, 66.1, 65.9, 65.7, 64.6, 60.4, 59.9, 57.9, 57.3, 51.6, 51.3, 48.3, 48.1, 34.7, 34.4, 34.2, 34.1, 30.6, 30.3, 29.9, 29.5, 25.6, 14.5, 14.4, 14.2.

Synthesis of (2S)-(E,Z)-N-(Allyloxycarbonyl)-4-ethylidene-o-(tert-butyldimethylsilyl)-pyrrolidinemethanol (18)

Tert-butyldimethylsilyl chloride (1.11 g, 7.37 mmol, 1.2 eq) was added to a solution of the hydroxy compound 17 (1.3 g, 6.36 mmol) and imidazole (1.05 g, 15.41 mmol, 2.5 eq) in dry DMF (3 ml) and the reaction mixture was allowed to stir overnight under $N_2$. The reaction mixture was then saturated with water (200 ml) and extracted with EtOAc (3×100 ml). The organic layer was washed with water (100 ml), brine (150 ml), dried ($MgSO_4$) and excess solvent was evaporated in vacuo to give a light brown oil which was subjected to flash chromatography (EtOAc:Petroleum ether, 50:50) to afford the pure silyl ether (18).

Yield 1.54 g (75%); IR (cm$^{-1}$) 3416, 2093, 1642, 1406, 1253, 1189, 1104, 775; $^1$H-NMR ($CDCl_3$, rotamers) δ 5.89–5.95 (m, 1H), 5.18–5.34 (m, 3H), 4.62 (s, 2H), 3.53–4.08 (m, 5H), 2.49–2.70 (m, 2H), 1.43–1.59 (m, 3H), 0.91 (bs, 9H), 0.02–0.003 (bs, 6H); $^{13}$C-NMR ($CDCl_3$) (E/Z isomers) δ 162.5, 154.4, 136.2, 135.1, 133.1, 130.9, 128.8, 117.4, 117.1, 116.7, 116.1, 65.9, 65.7, 65.5, 63.9, 63.6, 63.1, 58.6, 58.2, 58.1, 51.2, 48.3, 48.1, 36.5, 34.6, 33.9, 31.8, 31.4, 30.4, 30.3, 29.7, 29. 2, 29.1, 22.7, 18.1, 18.0, 14.5, 14.4, 14.1, −3.6, −5.4; MS (EI) (m/z, relative intensity) 325 (M+, 6), 310 (3), 268 (100), 256 (6), 240 (18), 224 (7), 182 (22), 180 (38), 168 (10 ), 154 (5), 136 (24), 115 (8), 94 (6), 75 (13), 73 (21), 57 (17); EI-HRMS m/z 325.2003 [(M-isobutyl) m/z 268.1233] (calc'd for $C_{17}H_{31}NO_3$ m/z 325.2073 [(M-isobutyl) m/z 268.1369).

Synthesis of (2S)-(E,Z)-4-ethylidene-O-(tert-butyldimethylsilyl)-pyrrolidinemethanol (19)

Tributyltinhydride (1.49 g, 5.1 mmol, 1.1 eq) was added to a solution of 18 (1.5 g, 4.62 mmol) in DCM (30 ml) in the presence of water (0.48 g, 27.11 mmol, 6 eq) and a catalytic amount of $Pd(PPh_3)_2Cl_2$ (0.132 g, 0.189 mmol, 4% molar) and the reaction mixture was allowed to stir for 5 minutes at room temperature. The reaction mixture was diluted with DCM (40 ml), dried ($MgSO_4$) and excess solvent removed under vacuum. The pure amine 19 was isolated by flash chromatography (EtOAc:Petroleum ether, 50:50) to afford a light brown oil.

Yield 0.67 g (60%); IR (cm$^{-1}$) 4329, 4257, 3426, 2923, 2728, 2672, 2360, 2341, 2035, 1777, 1713, 1641, 1512, 1463, 1377, 1302, 1242, 1169, 1019, 890, 760, 721; $^1$H-NMR ($CDCl_3$) δ 5.33–5.37 (m, 1H), 4.06 (s, 1H), 3.28–3.75 (m, 4H), 2.17–2.47 (m, 2H), 1.54–1.63 (m, 3H), 0.89 (bs, 9H), 0.06–0.007 (bs, 6H).

Synthesis of (2S)-(E,Z)-N-(4-benzyloxy-5-methoxy-2-nitrobenzoyl)-2-ethylidene-O-(tert-butyldimethylsilyl)-pyrrolidinemethanol (20)

A catalytic amount of DMF (4 drops) was added to a solution of 4-benzyloxy-5-methoxy-2-nitrobenzoic acid (3) (2.5 g, 8.25 mmol) and oxalyl chloride (1.25 g, 9.84 mmol, 1.2 eq) in dry THF (10 ml) was allowed to stir overnight at room temperature. The resulting chloride was added dropwise over 20 minutes to a solution of the deprotected C-ring 19 (1.98 g, 8.25 mmol, 1 eq), TEA (1.75 g, 17.35 mmol, 2.1 eq) and water (0.6 ml) at 0° C., under nitrogen. The reaction mixture was allowed to stir for a further 2.5 hours, at which point TLC (EtOAc:Petroleum ether, 40:60) indicated that the reaction was complete. The organic solvent was then removed under reduced pressure and the residue was partitioned between EtOAc (150 ml) and water (150 ml) and the layer separated. The aqueous layer was washed with EtOAc (100 ml) and the combined organic phase was washed with sat. $NH_4Cl$ (100 ml), brine (150 ml), dried ($MgSO_4$) and evaporated in vacuo to afford, after flash chromatography (EtOAc:Petroleum ether, 70:30), the coupled product 20.

Yield 2.85 g (66%); $[α]^{20}_D$: −11.7° (c 0.305, $CHCl_3$); IR (cm$^{-1}$) 4328, 3424, 2960, 2855, 2359, 2332, 2084, 1709, 1641, 1548, 1526, 1462, 1377, 1278, 1215, 1107, 1058, 836, 761, 722; $^1$H-NMR ($CDCl_3$) δ 7.37–7.47 (m, 6H), 6.77 (s, 1H), 5.33–5.37 (m, 1H), 5.22 (s, 2H), 4.43–4.59 (bs, 1H), 3.95 (s, 3H), 3.59–3.86 (m, 4H), 2.47–2.75 (m, 2H), 1.60–1.67 (m, 3H), 0.89 (bs, 9H), 0.087–0.09 (bs, 6H); $^{13}$C-NMR ($CDCl_3$) (E/Z isomers) δ 154.8, 135.3, 128.9, 127.6, 109.2, 71.3, 58.0, 57.6, 56.6, 30.3, 29.7, 25.7, 14.6, 14.4, −5.4, −5.6; MS (CI) (m/z, relative intensity) 527 (MH+, 25), 418 (82), 388 (6), 359 (9), 328 (7), 304 (25), 279 (45), 258 (13), 240 (35), 219 (11), 184 (10), 161 (51), 147 (21), 133 (41), 113 (21), 107 (100), 91 (25), 81 (8), 73 (40); EI-HRMS m/z 526.2642 (calc'd for $C_{28}H_{38}N_2O_6Si$ m/z 526.2499).

Synthesis of (2S)-(E,Z)-N-(4-benzyloxy-5-methoxy-2-nitrobenzoyl)-2-ethylidene pyrro-lidine methanol (21)

A solution of TBAF (1M solution in THF, 1.75 ml, 1.75 mmol, 1.2 eq) was added dropwise over 15 minutes at 0° C. under $N_2$ to a solution of the TBDMS protected intermediate 20 (0.75 g, 1.42 mmol) in dry THF (30 ml). The reaction mixture was allowed to warm to room temperature and to stir for a further 30 minutes when TLC (EtOAc) indicated complete consumption of the starting material. The reaction mixture was diluted with sat. aq. $NH_4Cl$ (150 ml) and extracted with EtOAc (3×100 ml). The organic phase was washed with brine (150 ml), dried ($MgSO_4$) and evaporated under reduced pressure to afford the deprotected product 21 which was used for the next step without further purification.

Yield 0.64 g (109%, some TBDMSF associated with the product; Yield$_{max}$ 0.57 g); IR (cm$^{-1}$) 4214, 3406, 3020, 2958, 2925, 2854, 2400, 2085, 1631, 1581, 1523, 1463, 1453, 1433, 1378, 1335, 1278, 1215, 1053, 870, 754; $^1$H-NMR (CDCl$_3$) δ 7.37–7.47 (m, 6H), 6.77 (s, 1H), 5.33–5.37 (m, 1H), 5.22 (s, 2H), 4.43–4.59 (bs, 1H), 3.95 (s, 3H), 3.59–3.86 (m, 4H), 2.47–2.75 (m, 2H), 1.60–1.67 (m, 3H), 0.89 (bs, 9H), 0.087–0.009 (bs, 6H).

(2s)-(E,Z)-N-(2-amino-4-benzyloxy-5-methoxybenzoyl)-2-ethylidenepyrrolidine methanol (22)

A solution of the nitro compound 21 (0.64 g, 1.38 mmol, assumes quantitative yield in previous step) in MeOH (30 ml) and SnCl$_2$.2H$_2$O (1.58 g, 7 mmol, 5 eq) was heated to reflux for 40 minutes when TLC (5% MeOH/CHCl$_3$) indicated the reaction was complete. The excess solvent was evaporated in vacuo and the residual oil was partitioned between EtOAc (100 ml) and sat. aq. NaHCO, (100 ml) and allowed to stir overnight under N$_2$. The organic layer was then separated and washed with brine (150 ml), dried (MgSO$_4$) and evaporated in vacuo. The residue was purified by flash chromatography (5% MeOH/CHCl$_3$) to give the pure amine intermediate 22 as a bright yellow oil.

Yield 0.32 g (61%); IR (cm$^{-1}$) 4329, 4257, 3427, 2923, 2727, 2360, 2341, 2036, 1712, 1624, 1513, 1463, 1377, 1264, 1215, 1172, 1120, 1002, 872, 761, 722; $^1$H-NMR (CDCl$_3$) δ 7.35–7.51 (m, 5H), 6.87 (s, 1H), 6.27 (s, 1H), 5.28–5.42 (m, 1H), 5.17 (s, 2H), 4.43–4.59 (bs, 1H), 3.84 (s, 3H), 3.59–3.78 (m, 4H), 2.25–2.75 (m, 2H), 1.60 (d, J=6.8 Hz, 3H); $^{13}$C-NMR (CDCl$_3$) (E/Z isomers) δ 150.9, 141.5, 136.6, 134.5, 128.8, 127.9, 127.1, 117.7, 117.3, 112.6, 103.0, 70.6, 66.1, 60.4, 59.8, 57.2, 34.3, 30.0, 29.4, 21.0, 14.6, 14.3, 13.6.

Synthesis of (2S)-(E,Z)-N-[2-(p-nitrobenzyloxy)carboxamido-4-benzyloxy-5-methoxy benzoyl]-2-ethylidenepyrrolidine methanol (23)

The freshly made amine 22 (0.5 g, 1.31 mmol) and dry pyridine (0.207 g, 2.62 mmol, 2 eq) was dissolved in dry DCM (30 ml) at 0° C. under N$_2$. A solution of 4-nitrobenzyl chloroformate (0.282 g, 1.31 mmol, 1 eq) was added to the amine solution dropwise over 20 min. The reaction mixture was allowed to stir under the same conditions for 2 hours at which time TLC (5% MeOH/CHCl$_3$) revealed complete consumption of the starting material. The mixture was then dissolved in DCM (100 ml) and washed with sat. aq. CuSO$_4$ (2×75 ml), water (2×100 ml), brine (150 ml) and dried (MgSO$_4$). The organic solvent was evaporated in vacuo and after purification by flash chromatography (3% MeOH/CHCl$_3$) the p-nitrobenzyl carbamate was isolated.

Yield 0.56 g (76.3%); [α]$^{20}$$_D$: +204.6° (c 0.22, CHCl$_3$); IR (cm$^{-1}$) 4329, 4257, 3426, 2924, 2853, 2093, 1710, 1628, 1524, 1462, 1406, 1377, 13460, 1269, 1219, 1175, 1118, 722; $^1$H-NMR (CDCl$_3$, rotamers) δ 8.81 (bs, 1H), 8.19 (d, J=8.6 Hz, 2H), 7.80 (s, 1H), 7.31–7.61 (m, 7H), 6.85 (s, 1H), 5.29–5.35 (m, 1H), 5.24 (s, 2H), 5.15 (s, 2H), 4.08–4.13 (bs, 1H), 3.83 (s, 3H), 3.66–3.86 (m, 4H), 2.39–2.75 (m, 2H), 1.51 (d, J=6.6 Hz, 3H); $^{13}$C-NMR (CDCl$_3$) (E/Z isomers) δ 153.2, 150.3, 147.6, 143.6, 136.1, 134.1, 128.7, 128.4, 128.1, 127.7, 126.9, 123.7, 117.8, 111.2, 70.7, 65.2, 63.8, 56.6, 29.7, 14.6, 14.4; MS (FAB) (m/z, relative intensity) 562 (MH$^+$, 15), 279 (77), 256 (15), 240 (35), 231 (37), 136 (13), 128 (25), 106 (14), 91 (100), 73 (11), 57 (11); EI-HRMS m/z 561.2150 (calc'd for C$_{30}$H$_{31}$N$_3$O$_8$ m/z 561.2111).

Synthesis of (11aS)-8-benzyloxy-7-methoxy-1,3,10,11,11a-tetrahydro-2-ethylidene-11-hydroxy-10-(p-nitrobenzyloxy)carboxy-5H-pyrrolo[2,1-c][1,4]-benzodiazepine-5-one (24)

A solution of the uncyclised carbamate 23 (0.3 g, 0.535 mmol), NMO (94 mg, 0.803 mmol, 1.5 eq) and mol. sieve (0.267 g) in a mixture of dry (DCM:CH$_3$CN, 9:3 ml) was allowed to stir at room temperature under N$_2$ for 15 min. TPAP (9.4 mg, 0.026 mmol, 5% molar) was then added and the mixture was allowed to stir under the same conditions for a further 2.5 hours. The reaction mixture was filtered through Celite and the filtrate evaporated in vacua. The residue was subjected to flash chromatography (1% MeOH/CHCl$_3$) to obtain the target compound (24).

Example 5

Synthesis of PBD Dimer Prodrugs

Example 5(a)

Synthesis of 1,1'-[[(Propane-1,3-diyl)dioxy]bis[[2-(4-nitrobenzyloxycarboxamido)]bis[(11aS)-7-methoxy-1,2,3,11a-tetrahydro-11-hydroxy-5H-pyrrolo[1,2-c][1,4]benzodiazepine-5-one (30)

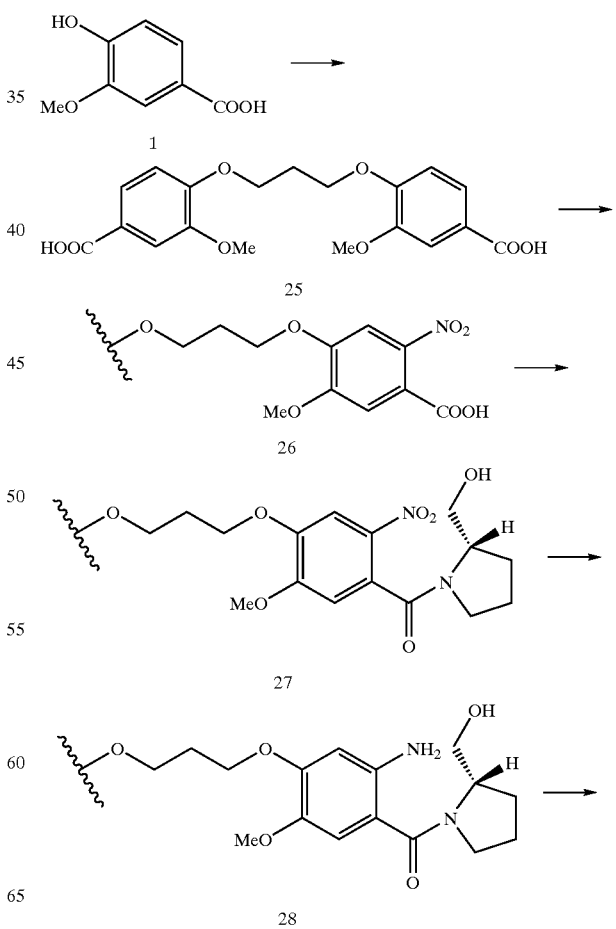

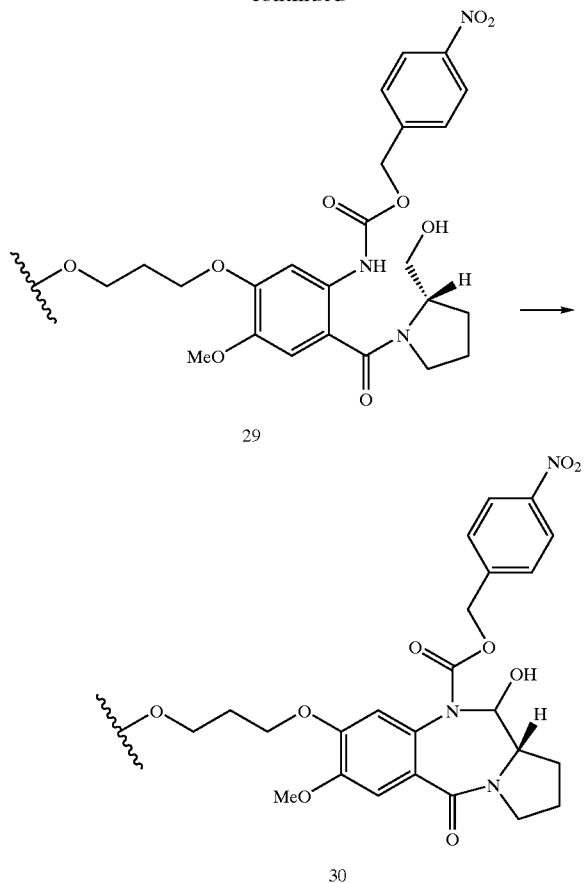

Synthesis of 1',3'-Bis(4-carboxy-2-methoxyphenoxy)propane (25)

A solution of diiodopropane (4.2 g, 14.2 mmol) was dissolved in THF (30 ml) was added dropwise to a vigorously stirred solution of vanillic acid (1) (4-hydroxy-3-methoxybenzoic acid) (5 g, 29.8 mmol, 2.1 eq) and aq. 0.5 M NaOH (70 ml) in THF (50 ml). The reaction mixture was allowed to reflux for 48 hours and the organic solvent was removed under reduced pressure. The remaining aqueous phase was washed with Petroleum ether 40–60 (3×100 ml) and it was then acidified with conc. HCl to pH 2 until no further precipitation was observed. The precipitate was collected filtration, washed with water, dried to afford the dimer acid (25) as white crystals.

Yield 7.63 g (68%); $^1$H-NMR (CDCl$_3$+DMSO-d$_6$) δ 7.64 (dd, J$_1$=8.3 Hz, J$_2$=8.3 Hz, 2H), 7.54 (s, 2H), 6.96 (d, J=8.4 Hz, 2H), 4.29 (t, J=6.1 Hz, 4H) 3.88 (s, 6H), 2.38 (t, J=6.2 Hz, 2H); $^{13}$C-NMR (CDCl$_3$+DMSO-d$_6$) δ 173.1, 168.1, 151.9, 148.6, 123.5, 112.4, 111.45, 65.21, 55.8, 28.8; IR (cm$^{-1}$)=3600–3100, 2925, 2855, 1713, 1680, 1597, 1516, 1459, 1377, 1344, 1309, 1275, 1223, 1178, 1133, 1045, 1021; MS (EI) (m/z, relative intensity) 376 (M$^+$, 34), 208 (31), 168 (43), 152 (15), 101 (100), 69 (87); EI-HRMS m/z 376.1136 (calc'd for C$_{19}$H$_{20}$O$_8$ m/z 376.1158)

Synthesis of 1',3'-Bis(4-carboxy-2-methoxy-5-nitrophenoxy)propane (26)

The dimer acid 25 (5 g, 13.3 mmol) was added slowly in small portions over 30 minutes to a stirred solution of 70% HNO$_3$ (50 ml) at 0° C. After the addition was complete the reaction mixture was allowed to warm to 15° C. and stirring continued for a further 2 hours. The reaction mixture was poured onto ice causing precipitation of the product. The yellow precipitate was collected by filtration, washed with cold water and dried to afford the nitrated dimer acid core (26) as a pale yellow solid.

Yield 4.52 g (73%); mp 241–246° C.; IR (cm$^{-1}$) 3500–3200, 2924, 1713, 1604, 1582, 1523, 1459, 1377, 1282, 1218, 1189, 1053; $^1$H-NMR (CDCl$_3$+DMSO-d$_6$) δ 7.44 (s, 2H), 7.16 (s, 2H), 4.32 (t, J=6.5 Hz, 4H), 3.94 (s, 6H), 2.44 (t, J=6.4 Hz, 2H); $^{13}$C-NMR (CDCl$_3$+DMSO-d$_6$) δ 172.3, 167.11, 152.5, 149.2, 141.1, 132.1, 128.6, 122.7, 111.2, 108.3, 65.2, 56.4, 33.9; MS (EI) (m/z, relative intensity) 467 (MH$^+$, 1), 436 (5), 423 (10), 376 (2), 256 (6), 210 (4), 183 (10), 164 (10), 153 (3), 91 (9), 77 (4), 51 (13), 44 (100); EI-HRMS m/z 466.0876 (calc'd for C$_{19}$H$_{18}$N$_2$O$_{12}$ 466.0858).

Synthesis of 1,1'-[[(Propane-1,3-diyl)dioxy]bis[(2-nitro-5-methoxy-1,4-phenylene)carbonyl]bis[pyrrolidinemethanol] (27)

A solution of the nitrated dimer core 26 (1 g, 2.14 mmol) in a mixture of dry CH$_3$CN/THF (30:5 ml) was treated overnight with oxalyl chloride (0.64 g, 5.14 mmol, 2.4 eq) and DMF (5 drops). The resulting acid chloride was then added dropwise over 30 minutes to a suspension of pyrrolidinemethanol (0.432 g, 4.28 mmol, 2 eq) and K$_2$CO$_3$, (1.2 g, 8.56 mmol, 4 eq) in dry acetonitrile (80 ml) at −25° C., under nitrogen. The resulting mixture was allowed to stir at −25° C. for a further 1.5 hour when the reaction mixture was diluted with water (100 ml). The solution was then extracted with chloroform (4×100 ml). The combined organic phase was washed with aq. 1M HCl (2×75 ml), water (2×75 ml), brine (100 ml), dried (MgSO$_4$) and evaporated in vacuo. The resulting orange oil was purified by column chromatography (10% MeOH/CHCl$_3$) to afford the pure product 27 as a yellow viscous oil.

Yield 0.88 g (65%); [α]$^{20}$$_D$+246.1° (c 0.067, CHCl$_3$); IR (cm$^{-1}$) 4329, 4257, 3370, 2916, 2728, 1787, 1713, 1614, 1574, 1513, 1462, 1377, 1337, 1274, 1215, 1058, 868, 823, 749, 723; $^1$H-NMR (CDCl$_3$) δ 7.73 (s, 2H), 6.80 (s, 2H), 4.31–4.36 (m, 6H), 3.94 (s, 6H), 3.74–3.87 (m, 4H), 3.17 (t, J=6 Hz, 4H), 2.44 (t, J=5.9 Hz), 2.12–2.22 (m, 4H), 1.70–1.92 (m, 4H); $^{13}$C-NMR (CDCl$_3$) δ 154.8, 148.3, 137.0, 128.0, 109.1, 108.4, 66.0, 65.6, 61.4, 56.7, 49.5, 28.6, 24.4; MS (FAB) (m/z, relative intensity) 633 (M$^+$+1, 52), 449 (12), 236 (11), 219 (17), 206 (12), 196 (15), 191 (22), 178 (20), 166 (20), 151 (34), 135 (23), 128 (11), 122 (33), 115 (11), 102 (47), 91 (100), 84 (45).

Synthesis of 1,1'-[[(Propane-1,3-diyl)dioxy]bis[(2-amino-5-methoxy-1,4-phenylene)carbonyl]bis[pyrrolidinemethanol] (28)

Hydrazine hydrate (0.87 g, 1.74 mmol, 10 eq) was added dropwise to a solution of the nitro intermediate (27) (1 g, 1.58 mmol) over Raney Nickel (0.25 g) in gently refluxing methanol (20 ml). (Anti-bumping granules were used to ensure even boiling). The reaction mixture was heated at reflux for a further 15 minutes at which time TLC (10% MeOH/CHCl$_3$) indicated that the reaction had gone to completion. The catalyst was then removed by filtration (causation! pyrophoric Ni) and the filtrate was evaporated in vacuo to give a dark brown oil which was purified by flash chromatography (7.5% MeOH/CHCl$_3$) to afford the coupled dimer amine (28) as a bright yellow oil.

Yield=0.632 g (70 %); IR (cm$^{-1}$) 3100–3600, 2925, 1611, 1460, 1377, 1275, 1216, 1175; $^1$H-NMR (CDCl$_3$) δ 6.74 (s, 2H), 6.33 (s, 2H), 4.31–4.42 (m, 2H), 4.19–4.23 (m, 4H), 3.76 (s, 6H), 3.50–3.66 (m, 8H), 2.27–2.40 (m, 2H), 2.02–2.15 (m, 4H), 1.71–1.87 (m, 4H); $^{13}$C-NMR (CDCl$_3$) δ 151.1, 141.0, 112.8, 102.3, 65.1, 60.8, 57.1, 50.9, 28.7, 28.4; MS (FAB) (m/z, relative intensity) 574 (M$^+$+2, 44), 503 (3), 473 (30), 389 (11), 371 (31), 219 (14), 206 (50), 198 (13), 192 (27), 180 (30), 166 (18), 149 (28), 137 (23), 128 (17), 102 (43), 93 (68), 84 (57), 70 (33), 57 (35).

Synthesis of 1,1-[[(Propane-1,3-diyl)dioxy]bis[[2-(4-nitrobenzyloxycarboxamido)-5-methoxy-1,4-phenylene]carbonyl]bis-pyrrolidinemethanol (29)

A solution of 4-nitrobenzyl chloroformate (0.347 g, 1.61 mmol, 2.3 eq) in dry DCM (10 ml) was added dropwise over 20 min, under nitrogen to a freshly prepared solution of dimer amine 28(0.4 g, 0.7 mmol) in dry DCM (15 ml) and pyridine (0.193 g, 2.45 mmol, 3.5 eq) at 0° C. The resulting reaction mixture was allowed to stir for a further 1.5 hours at 0° C. at which time TLC (10% MeOH/CHCl$_3$) indicated complete consumption of starting material. The reaction mixture was diluted with chloroform (50 ml) and washed with a saturated aqueous solution of CuSO$_4$ (2×50 ml), water (2×50 ml), brine (100 ml) and dried (MgSO$_4$). The organic solvent was removed in vacuo and the pure dimer carbamate 29 was obtained after flash chromatography (7% MeOH/CHCl$_3$) as a bright yellow foam.

Yield 0.53 g (81%); IR (cm$^{-1}$) 3424, 2088, 1641, 1502, 1247; $^1$H-NMR CDCl$_3$) δ 9.02 (bs, 2H), 8.21 (d, J=8.8 Hz, 4H), 7.72 (s, 2H), 7.56 (d, J=8.8 Hz, 4H), 6.82 (s, 2H), 5.26 (s, 4H), 4.28–4.38 (m, 2H) , 4.26 (t, J=6 Hz, 4H), 3.79 (s, 6H) , 3.42–3.79 (m, 8H), 2.27–2.42 (m, 2H), 2.11–2.18 (m, 4H) , 1.71–1.88 (m, 4H); $^{13}$C-NMR (CDCl$_3$) δ 170.7, 153.2, 150.6, 147.6, 143.6, 128.5, 126.9, 123.9, 111.5, 105.9, 65.3, 63.8, 61.0, 56.6, 51.6, 30.3, 28.4; MS (FAB) (m/z, relative intensity) 932 (M$^+$+2, 3), 753 (5), 551 (5), 249 (7), 232 (13), 222 (8), 206 (23), 192 (32), 179 (27), 166 (46), 149 (28), 136 (66), 120 (22), 106 (45), 102 (100), 91 (80), 84 (48), 73 (71), 57 (47).

Synthesis of 1,1'-[[(Propane-1,3-diyl)dioxy]bis[[2-(4-nitrobenzyloxycarboxamido)]bis[(11aS)-7-methoxy-1,2,3,11a-tetrahydro-11-hydroxy-5H-pyrrolo[1,2-c][1,4]benzodiazepine-5-one (30)

TPAP (13.4 mg, 0.114 mmol, 0.3 eq) was added in one portion to a solution of the bis carbamate 29 (0.35 g, 0.37 mmol) and NMO (0.134 g, 1.14 mmol, 3.1 eq) in dry DCM/CH$_3$CN (9:3 ml) which has been allowed to stir over molecular sieve (0.350 g) for 15 minutes under N$_2$ and at room temperature. Progress of the reaction was followed by TLC (7% MeOH/CHCl$_3$). After 2 hours reaction was still incomplete requiring the addition of a further amount of NMO (67 mg, 0.55 mmol, 1.5 eq) and TPAP (6.7 mg, 0.05 mmol, 0.15 eq). After stirring for a further 30 minutes TLC revealed the complete consumption of starting material. The reaction mixture was filtered through Celite and the filtrate evaporated in vacuo. The resulting black residue was subjected to column chromatography (1.5% MeOH/CHCl$_3$) to afford the product as an opaque pale yellow oil.

Yield 0.143 (42%); IR (cm$^{-1}$) 3500–3000, 2933, 2253, 1728, 1599, 1523, 1465, 1431, 1409, 1348, 1270, 1206, 1174, 1111, 1060; $^1$H-NMR (CDCl$_3$, rotamers) δ 8.18 (d, J=8.8 Hz, 4H), 7.74 (s, 2H), 7.48 (d, J=8.8 Hz, 4H), 6.71 (s, 2H), 5.65 (d, J=10 Hz, 2H), 5.26 (s, 4H), 4.29 (t, J=6 Hz, 4H), 4.07–4.16 (m, 2H), 3.83 (s, 6H), 3.42–3.75 (m, 8H), 2.25–2.32 (m, 2H), 2.10–2.22 (m, 4H), 1.68–1.75 (m, 4H); $^{13}$C-NMR (CDCl$_3$) δ 166.9, 153.2, 147.6, 143.8, 142.8, 128.2, 123.9, 113.9, 110.9, 108.3, 86.2, 69.1, 66.3, 65.6, 60.0, 56.4, 46.4, 29.7, 28.7, 23.1, 14.8; MS (FAB) (m/z, relative intensity) 925 (M$^+$–1, 1), 889 (5), 711 (6), 501 (3), 286 (10), 252 (7), 213 (15), 192 (32), 197 (11), 185 (22), 181 (42), 165 (15), 149 (47), 131 (18), 119 (16), 105 (29), 91 (96), 73 (100), 57 (54).

Example 5(b)

Synthesis of 1,1'-[[(Propane-1,3-diyl)dioxy]bis[[2-(2,3-dimethoxy-5-nitrobenzyloxycarboxamido)]bis[(11aS)-7-methoxy-1,2,3,11a-tetrahydro-11-hydroxy-5,H-pyrrolo[1,2-c][1,4]benzodiazepine-5-one (32)

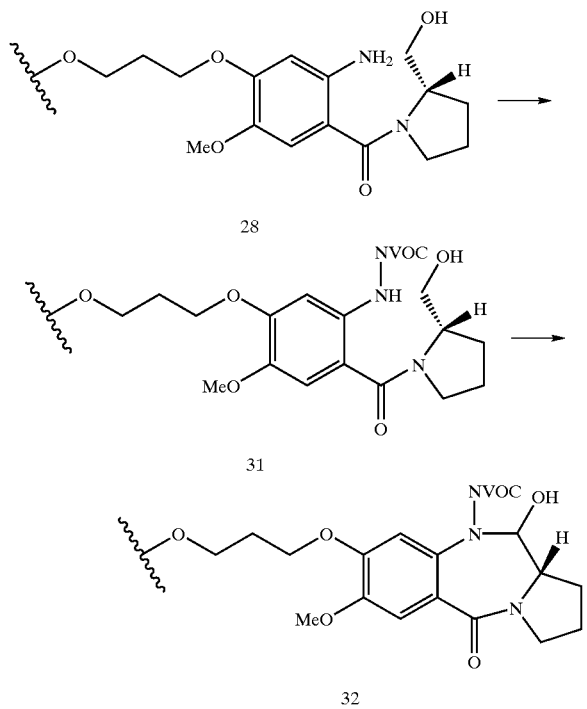

Synthesis of 1,1'-[[(Propane-1,3-diyl)dioxy]bis[[2-(2,3-dimethoxy-5-nitrobenzyloxycarboxamido)-5-methoxy-1,4-phenylene]carbonyl]bis-pyrrolidinemethanol (31)

A solution of 2-nitro-4,5-dimethoxybenzyl chloroformate (0.443 g, 1.61 mmol, 2.3 eq) in dry DCM (10 ml) was added dropwise over 20 minutes to a stirred solution of the amino alcohol 28 (0.4 g, 0.7 mmol) and pyridine (0.193 g, 2.54 mmol, 3.5 eq) in dry DCM (15 ml) at 0° C., under N$_2$. TLC (10% MeOH/CHCl$_3$) revealed the reaction had gone to completion after 2 hours. The reaction mixture was then diluted with chloroform (50 ml) and washed with saturated aqueous solution of CUSO$_4$ (2×50 ml), water (2×50 ml), brine (100 ml) and dried (MgSO$_4$). Removal of the solvent under reduced pressure gave a dark yellow oil which was further purified by flash chromatography (7% MeOH/CHCl$_3$) to afford the pure product as a yellow foam.

Yield 0.564 (77%); [α]$^{20}_D$–43.3° (c 0.485, CHCl$_3$); IR (cm$^{-1}$) 4214, 3416, 3020, 2973, 2940, 2613, 2400, 2254, 2075, 1727, 1618, 1585, 1522, 1465, 1438, 1408, 1331, 1278, 1216, 1174, 1118, 1071, 1030, 987, 909, 874, 850, 754; $^1$H-NMR (CDCl$_3$, rotamers) δ 8.93 (bs, 2H), 7.71 (s, 2H), 7.69 (s, 2H), 7.10 (s, 2H), 6.82 (s, 2H), 5.60 (m, 4H), 4.34 (m, 2H), 4.26 (t, J=6 Hz, 4H), 3.99 (s, 12H), 3.94 (s, 6H), 3.51–3.79 (m, 8H), 2.26–2.36 (m, 2H), 2.05–2.17 (m, 4H), 1.80–1.88 (m, 4H); $^{13}$C-NMR (CDCl$_3$) δ 170.6, 153.7, 150.45, 148.1, 139.5, 132.9, 127.8, 111.2, 110.4, 109.9, 108.1, 65.4, 63.8, 62.4, 60.8, 56.4, 53.5, 51.4, 50.6, 28.2, 25.0, 21.0, 14.2; MS (FAB) (m/z, relative intensity) 1053 (M$^+$+2, 7), 814 (6), 416 (3), 306 (13), 292 (5), 280 (27), 246 (46), 197 (81), 186 (38), 180 (25), 166 (37), 151 (19), 102 (23), 93 (100), 84 (10), 75 (37), 57 (42).

Synthesis of 1,1'-[[(Propane-1,3-diyl)dioxy]bis[[2-(2,3-dimethoxy-5-nitrobenzyloxycarboxamido)]bis[(11aS)-7-methoxy-1,2,3,11a-tetrahydro-11-hydroxy-5H-pyrrolo[1,2-c][1,4]benzodiazepine-5-one (32)

NMO (0.138 g, 1.16 mmol, 3.1 eq) and molecular sieve (350 mg) was added to a stirred solution of the NVOC dimer carbamate 31(0.4 g, 0.38 mmol) in dry DCM and acetonitrile (9:3 ml) under nitrogen. This mixture was allowed to stir for 15 minutes before the addition of TPAP (13.8 mg, 0.116 mmol, 0.3 eq). Further stirring of the reaction mixture for 2 hours at room temperature was followed by the addition of an additional amount of TPAP (6.9 mg, 0.058 mmol, 0.15 eq) and NMO (69 mg, 1.58 mmol, 1.5 eq) to drive the reaction to completion [TLC (5% MeOH/CHCl$_3$)] after a further 45 minute period of vigorous stirring. The organic solvent was evaporated in vacuo to afford a black residue which was further purified by column chromatography (1% MeOH/CHCl$_3$) to afford the pure final product as a dark yellow oil.

Yield 0.162 (39 %); [α]$^{20}$$_D$–121.5° (c 1.07, CHCl$_3$);IR (cm$^{-1}$) 4329, 4258, 3426, 2926, 2854, 2728, 2360, 2341, 2046, 1712, 1620, 1583, 1523, 1464, 1408, 1330, 1278, 1219, 1172, 1149, 1071, 1030, 987, 871, 796, 759; $^1$H-NMR (CDCl$_3$, rotamers) δ 7.71 (s, 2H), 7.62 (s, 2H), 7.10 (s, 2H), 6.43 (s, 2H), 5.48–5.59 (m, 6H), 4.29–4.36 (m, 2H), 4.24–4.28 (t, J=6 Hz, 4H), 3.95 (s, 12H), 3.88 (s, 6H), 3.47–3.53 (m, 8H), 2.32–2.43 (m, 2H), 2.07–2.17 (m, 4H), 1.67–1.92 (m, 4H); $^{13}$C-NMR (CDCl$_3$) δ 170.4, 153.8, 150.2, 148.9, 139.6, 130.9, 128.8, 127.6, 111.5, 110.6, 108.1, 86.0, 65.4, 65.0, 63.8, 60.9, 56.4, 46.4, 31.9, 28.2, 25.9, 22.7, 14.1.

Example 5(c)

Synthesis of 1,1'-[[(Propane-1,3-diyl)dioxy]bis[[2-(phenylacetamide)]bis[(11aS)-7-methoxy-1,2,3,11a-tetrahydro-11-hydroxy-5H-pyrrolo[1,2-c][1,4]benzodiazepine-5-one (34)

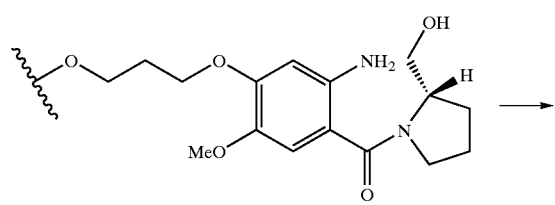

28

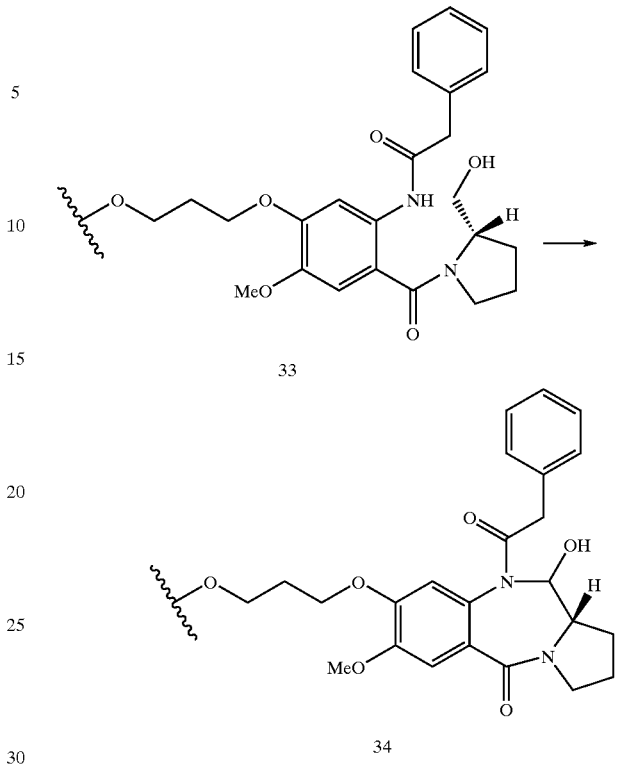

33

34

Synthesis of 1,1'-[[(Propane-1,3-diyl)dioxy]bis[[2-(phenylacetamnide)-5-methoxy-1,4-phenylene]carbonyl]bis-pyrrolidinemethanol [333]

A catalytic quantity of DMF (4 drops) was added to a stirred solution of phenyl acetic acid (0.2 g, 1.47 mmol, 2.1 eq) and oxalyl chloride (0.224 g, 1.76 g, 2.5 eq) in dry acetonitrile (10 ml) and the reaction mixture was allowed to stir overnight at room temperature under N$_2$. The solution of the resulting acid chloride was added dropwise over 30 minutes to a stirred solution of the amine 28 (0.4 g, 0.7 mmol) in dry acetonitrile (40 ml) over K$_2$CO$_3$ (0.406 g, 2.94 mmol, 4.2 eq) at –25° C., under N$_2$ and the reaction mixture was allowed to stir for a further 1.5 hours. The reaction mixture was diluted in chloroform (50 ml) and washed with 1M HCl (2×50 ml), water (2×75 ml), brine (100 ml), dried (MgSO$_4$) . Excess solvent was evaporated in vacuo to give a dark yellow oil which, after flash chromatography (10% MeOH/CHCl$_3$), afforded the pure phenylacetamide protected dimer amino alcohol as a pale yellow oil.

Yield 0.344 (64%); $^1$H-NMR (CDCl$_3$, rotamers) δ 9.31 (bs, 2H), 7.59 (s, 2H), 7.35 (s, 10H), 6.68 (s, 2H), 4.20–4.28 (m, 6H), 4.14–4.18 (m, 4H), 3.71 (s, 6H), 3.24–3.56 (m, 8H), 2.27–2.39 (m, 2H), 2.02–2.17 (m, 4H), 1.64–1.81 (m, 4H); $^1$C-NMR (CDCl$_3$) δ 169.7, 150.1, 134.7, 130.2, 129.4, 128.9, 127.3, 110.5, 108.2, 65.3, 61.1, 56.3, 50.8, 44.7, 29.7, 28.3, 24.7.

Synthesis of 1,1'-[[(Propane-1,3-diyl)dioxy]bis[[2-(phenylacetamide)]bis[(11aS)-7-methoxy-1,2,3,11a-tetrahydro-11-hydroxy-5H-pyrrolo[1,2-c][1,4]benzodiazepine-5-one (34)

NMO (0.141 g, 1.2 mmol, 3.1 eq) and mol. sieve (350 mg) was added to a stirred solution of the phenylacetamide protected dimer carbamate 33(0.3 g, 0.38 mmol) in dry DCM and acetonitrile (9:3 ml) under nitrogen. This mixture was allowed to stir for 20 minutes before the addition of TPAP (14.1 mg, 0.12 mmol, 0.31 eq). Further stirring of the reaction mixture for 1.5 hours at room temperature was followed by the addition of an additional amount of TPAP (7 mg, 0.06 mmol, 0.15 eq) and NMO (70 mg, 0.6 mmol, 1.5 eq) to drive the reaction to completion [TLC (5% MeOH/CHCl$_3$)] after a further 45 minute period of vigorous stirring. The organic solvent was evaporated in vacuo to afford a black residue which was further purified by column chromatography (1% MeOH/CHCl$_3$) to afford the pure final product as a dark yellow oil.

Yield 0.138 g (47.5%); [α]$^{20}_D$+132° (c 0.265, CHCl$_3$); IR (cm$^{-1}$) 3412, 2959, 2924, 2854, 2094, 1642, 1462, 1377; $^1$H-NMR (CDCl$_3$, rotamers) δ 7.28–7.39 (s, 10H), 7.15 (s, 2H), 6.46 (s, 2H), 5.75–5.78 (d, J=10 Hz, 2H), 4.10–4.35 (m, 10H), 3.89 (s, 6H), 3.35–3.73 (m, 8H), 2.27–2.32 (m, 2H), 1.68–2.05 (m, 8H); $^{13}$C-NMR (CDCl$_3$) δ 169.9, 153.2, 147.6, 143.8, 142.8, 128.2, 123.9, 113.9, 110.9, 108.3, 86.5, 69.1, 66.3, 65.6, 60.0, 56.4, 46.4, 29.7, 28.7, 23.1, 14.8.

Example 5(d)

Alternative Synthesis of 1,1'-[[(Propane-1,3-diyl)dioxy]bis[[2-(4-nitrobenzyloxycarboxamido)]bis[(11aS)-7-5 methoxy-1,2,3,11a-tetrahydro-11-hydroxy-5H-pyrrolo[2-c][1,4benzodiazepine-5-one (30)

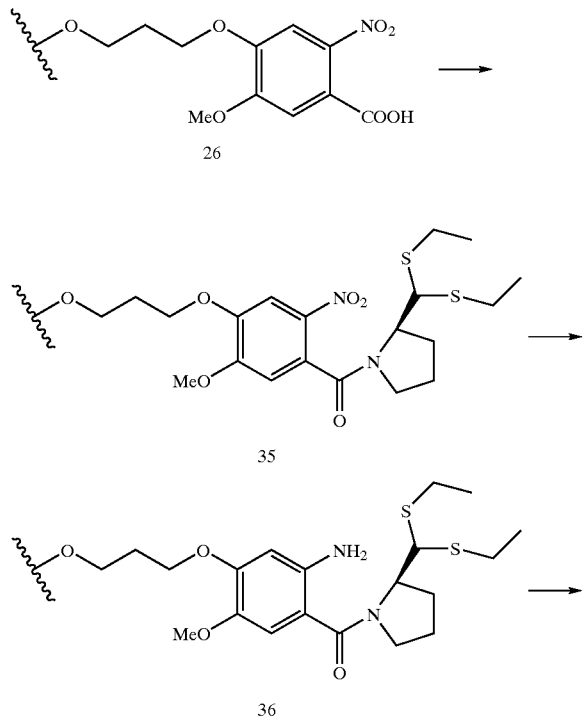

Synthesis of 1,1'-[[(propane-1,3-diyl)dioxy]bis[(2-nitro-5-methoxy1,4-phenylene)carbonyl]]bis[pyrrolidine-2-carboxaldehydediethyldithioacetal] (35)

3–4 drops of DMF was added to a stirred suspension of the dimer nitro acid 26 (0.25 g, 1.01 mmol) and oxalyl chloride (0.3 g, 2.33 mmol, 2.3 eq) in dry THF volume and the reaction mixture was allowed to stir overnight under nitrogen. The resulting acid chloride was added dropwise, over 20 min, to a stirred solution of (2S)-pyrrolidine-2-carbaldehyde diethyl thioacetal (0.416 g, 2.02 mmol, 2 eq) and triethylamine (0.41 g, 4.04 mmol, 4 eq) at 0° C., under N$_2$. The reaction mixture was allowed to warm to room temperature and stirring was continued for a further 1.5 hours. Excess THF was then removed and the residue was diluted with water (5 ml) and extracted with EtOAc (15 ml). The pH of the aqueous phase was adjusted to pH 3 with two drops of conc. HCl and subsequently extracted with EtOAc (3×10 ml). The combined organic phase was washed with water (2×10 ml), brine (15 ml), dried (MgSO$_4$) and the organic solvent was evaporated in vacuo to afford a dark red oil. Purification by flash chromatography (EtOAc:Petroleum ether 40–60, 1:1) afforded the pure product 35.

Yield 0.558 g (66%); $^1$H-NMR (CDCl$_3$) δ 7.72 (s, 2H), 6.83 (s, 2H), 4.89 (d, J=4.0 Hz, 2H), 4.64–4.70 (m, 2H), 4.30–4.40 (m, 4H), 3.91 (s, 6H), 3.15–3.30 (m, 4H), 2.59–2.76 (m, 8H), 1.70–2.38 (m, 8H), 1.30–1.38 (m, 12H).

Synthesis of 1,1'-[[(propane-1,3-diyl)dioxy]bis[(2-amino-5-methoxy1,4-phenylene)carbonyl]]bis[pyrrolidine-2-carboxaldehydediethyldithioacetal] (36)

A solution of the nitro thioacetal 35(0.4 g, 0.47 mmol) and SnCl$_2$.2H$_2$O (1.4 g, 6.22 mmol, 13.2 eq) in methanol (7 ml) was heated at reflux for 40 minutes at which time TLC (EtOAc:Petroleum ether 40–60, 1:1) indicated the reaction was complete. After the reaction mixture was allowed to return to room temperature the pH was adjusted to pH 8 by the addition of sat. aq. NaHCO$_3$. The resulting suspension was diluted with EtOAc (100 ml) and it was allowed to stir overnight under nitrogen. The organic phase was separated and washed with brine (50 ml), dried (MgSO$_4$) and the solvent was removed under reduced pressure to give a dark yellow gum which was further purified by flash chromatography (EtOAc:Petroleum ether 40–60, 3:7) to afford the pure dimer amino thioacetal as a bright yellow oil.

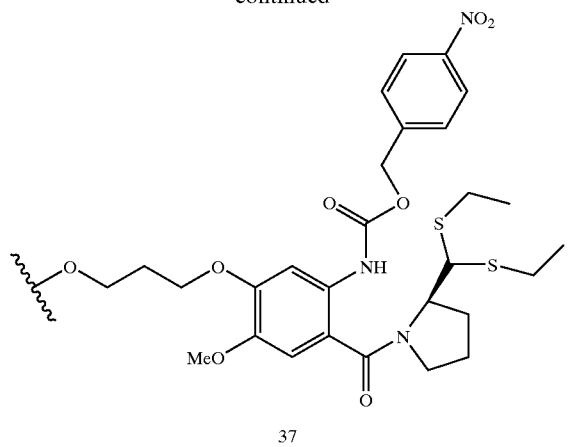

Yield 0.281 (56%); $^1$H-NMR (CDCl$_3$) δ 6.82 (s, 2H), 6.29 (s, 2H), 5.30 (d, J=4.0 Hz, 2H), 4.69–4.87 (m, 2H), 4.08–4.21 (m, 4H), 3.76 (s, 6H), 3.60–3.66 (m, 4H), 2.65–2.73 (m, 8H), 1.80–2.35 (m, 8H), 1.22–1.31 (m, 12H).

Synthesis of 1,1'-[[[(propane-1,3-diyl)dioxy]bis[(2-(4-nitrobenzyloxycarbonylamine-5-methoxy1,4-phenylene)carbonyl]]bis[pyrrolidine-2-carboxaldehydediethyldithioacetal] (37)

A solution of 4-nitrobenzyl chloroformate (0.100 g, 0.46 mmol, 2 eq) in dry DCM (10 ml) was added dropwise to a solution of the bis amine 36(0.18 g, 0.23 mmol) and pyridine (0.101 g, 1.28 mmol, 5.5 eq) in dry DCM (15 ml) over 20 minutes at 0° C., under nitrogen. The reaction solution was allowed to stir at 0° C. for a further 1.5 hours (TLC: 7% MeOH/CHCl$_3$), after which time it was allowed to warm to room temperature and diluted with chloroform (50 ml). The organic phase was washed with sat. aq. CuSO$_4$ (2×50 ml), water (75 ml), brine (75 ml), dried (MgSO$_4$) and the excess solvent evaporated in vacuo to give a dark yellow oil. After purification by flash chromatography (7% MeOH/CHCl$_3$) the pure product was obtained as a dark yellow oil.

Yield 0.179 (68%); $[\alpha]^{20}_D$+100° (c 0.232 CHCl$_3$); IR (cm$^{-1}$) 4214, 3426, 3020, 2400, 2085, 1658, 1609, 1525, 1466, 1452, 1408, 1348, 1268, 1216, 1174, 1112, 1052, 1015, 908, 753; $^1$H-NMR (CDCl$_3$, rotomers) δ 9.18 (bs, 2H), 8.19–8.24 (d, J=8.8 Hz, 4H), 6.82 (s, 2H), 6.29 (s, 2H), 5.30 (d, J=4.0 Hz, 2H,), 4.69–4.87 (m, 2H), 4.08–4.21 (m, 4H), 3.76 (s, 6H), 3.60–3.66 (m, 4H), 2.65–2.73 (m, 8H), 1.80–2.35 (m, 8H), 1.22–1.31 (m, 12H).

Synthesis of 1,1'-[[(Propane-1,3-diyl)dioxy]bis[[2-(4-nitrobenzyloxycarboxarmido)]bis[(11aS)-7-methoxy-1,2,3,11a-tetrahydro-11-hydroxy-5H-pyrrolo[1,2-c][1,4]benzodiazepine-5-one] (30)

Mercury chloride (1.6 g, 5.88 mmol, 4.5 eq) was added to a slowly stirred solution of the N-protected amino thioacetal 37(0.15 g, 0.13 mmol) and CaCO$_3$ (65 mg, 0.65 mmol, 5 eq) in acetonitrile/water (4:1, 5 ml) and stirring continued at room temperature for 24 hours. The reaction mixture was diluted with EtOAc (20 ml) and filtered through Celite. The filtrate was washed with sat. aq. NaHCO$_3$ (2×15 ml), brine (20 ml), dried (MgSO$_4$) and evaporated under reduced pressure to afford a yellow oil which was further purified by column chromatography (0 to 2% MeOH/CHCl$_3$) to afford the dimer prodrug compound 30 (Yield=67.3 mg (56%)).

Example 5(e)

Alternative synthesis of intermediate (26) in Examples 5(a) to 5(d)

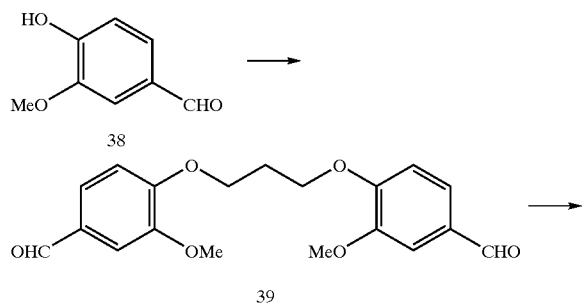

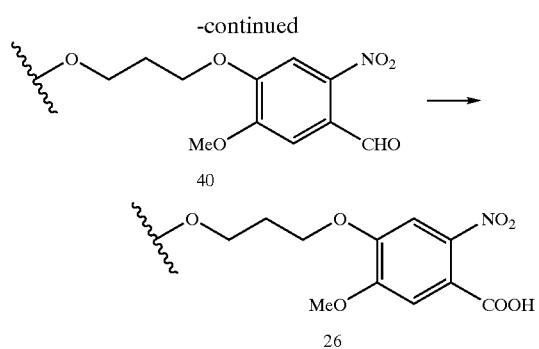

Synthesis of 1',3'-Bis(4-carbonyl-2-methoxyphenoxy) propane (39)

A solution of diethyl azodicarboxylate (4.57 g, 26 3 mmol, 1 eq) in dry THF (15 ml) was added dropwise over 15 minutes to a solution of vanillin (38) (10.4 g, 68.3 mmol, 2.6 eq), 1,3-propanediol (2 g, 26.3 mmol, 1 eq) and triphenyiphosphine (6.87 g, 26.3 mmol, 1 eq) in dry THF (50 ml) under nitrogen. The reaction mixture was allowed to stir overnight and diluted with chloroform (70 ml), washed with 1M NAOH (2×75 ml). The organic solvent was removed by rotary evaporation and the residue was triturated with toluene (150 ml) for 24 hours. Triphenylphosphine oxide was removed by filtration and the filtrate was washed with NAOH (100 ml), dried (MgSO$_4$), evaporated in vacuo and the remaining opaque oil was purified by flash chromatography (100% CHCl$_3$) to afford a white solid.

Yield=6.27 (70%); $^1$H-NMR (CDCl$_3$+DMSO-d$_6$) δ 9.84 (s, 2H), 7.62–7.66 (d, J=8.3 Hz, 2H), 7.38 (s, 2H), 7.02–7.05 (d, J=8.4 Hz, 2H), 4.24–4.28 (t, J=6.1 Hz, 4H), 3.91 (s, 6H), 2.05–2.12 (t, J=6.2 Hz, 2H); $^{13}$C-NMR (CDCl$_3$+DMSO-d$_6$) δ 190.8, 154.0, 149.6, 131.9, 129.7, 128.5, 126.7, 11.5, 109.1, 66.6, 61.4, 58.8, 55.9, 31.8, 14.5; MS (FAB) (m/z, relative intensity) 344 (M$^+$, 2), 210 (54), 152 (100), 123 (9), 109 (14), 81 (11), 65 (10), 51 (11).

Synthesis of 1',3'-Bis(4-carbonyl-2-methoxy-5-nitrophenoxy)propane (40)

The dimer aldehyde (39) (5 g, 14.5 mmol) was added in small portions over a period of 30 minutes to HNO$_3$ (100 ml, 70%) at 0° C. The resulting suspension was stirred for a further 30 minutes at 15° C. when it was poured onto ice-water and the bright yellow precipitate was collected by filtration, washed with cold water and dried to afford the nitrated intermediate.

Yield 4.63 g (74%); $^1$H-NMR (CDCl$_3$+DMSO-d$_6$) δ 10.41 (s, 2H), 7.67 (s, 2H), 7.37 (s, 2H), 4.41–4.45 (t, J=6.1 Hz, 4H), 3.99 (s, 6H), 2.87–2.92 (t, J=6.2 Hz, 2H); $^{13}$C-NMR (CDCl$_3$+DMSO-d$_6$) δ 187.7, 172.2, 153.4, 151.5, 143.6, 132.0, 128.6, 125.6, 110.3, 109.9, 108.4, 65.8, 56.6, 33.8; MS (EI) (m/z, relative intensity) 434 (M$^+$, 1), 277 (33), 269 (37), 214 (13), 197 (21), 167 (100), 152 (21), 122 (20), 111 (15), 96 (10), 79 (13), 72 (32).

Synthesis of 1',3'-Bis(4-carboxy-2-methoxy-5-nitrophenoxy)propane (26)

Hot aqueous KMnO$_4$ (10% w/v, 200 ml) was added dropwise to a solution of the aldehyde (40) (4 g, 9.21 mmol) in acetone (300 ml) over 15 min. The resulting mixture was stirred for 40 minutes and the insoluble material was removed by filtration through celite. The pad was washed with hot water and the combined filtrate concentrated in vacuo. The remaining aqueous phase was acidified with conc. HCl to afford a pale yellow precipitate which was collected by filtration, washed with water and dried to give the dimer acid (26) (Yield 3.08 g (71.8%)).
Example 6
Synthesis of a Psec-protected PBD (52) and related Ptec-protected PBD (55a/b) (for comparison)
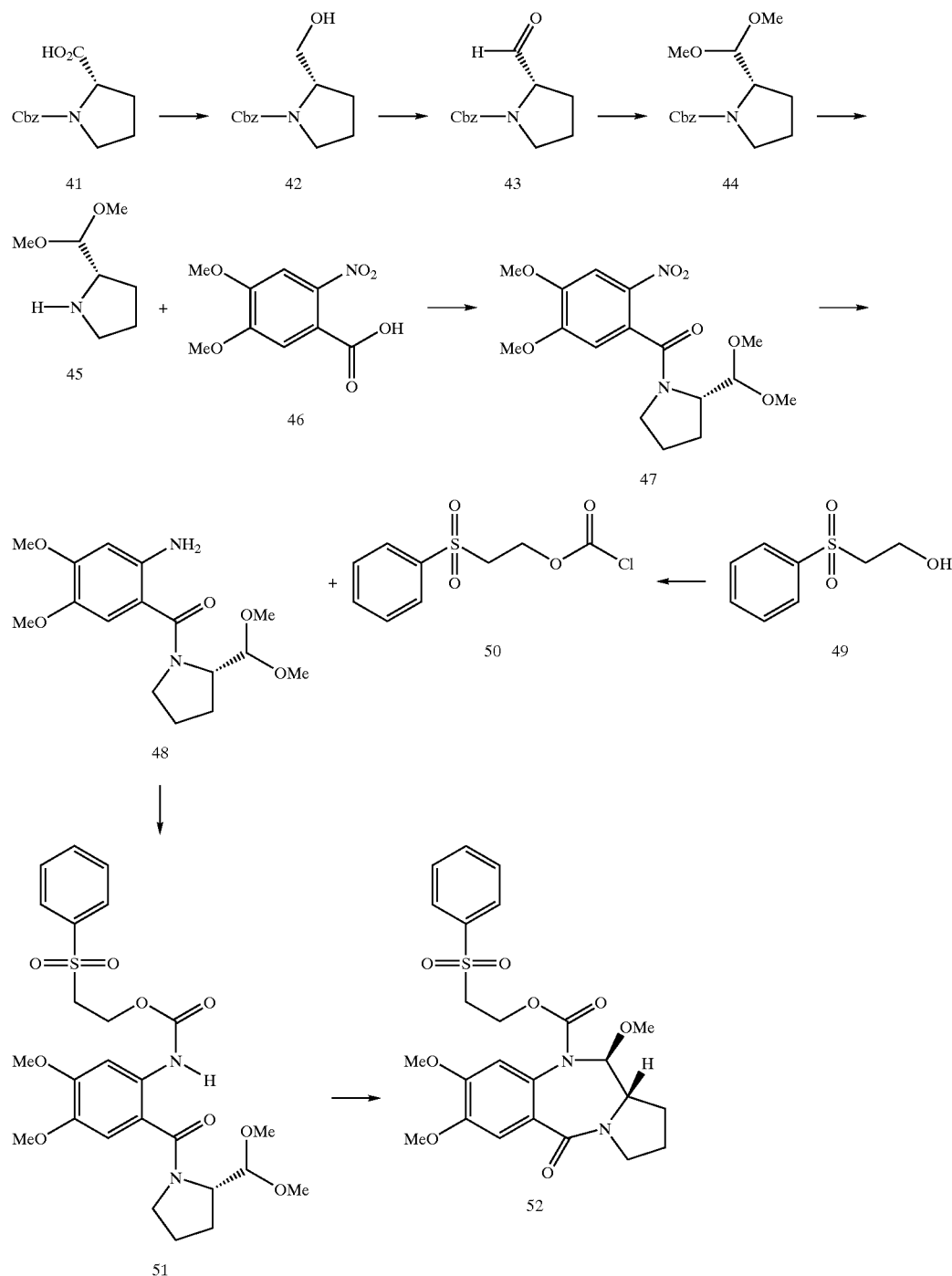

Synthesis of Secondary Amine 45

Lithium tetrahydroborate (2.6 g, 0.12 mol) was added portionwise 5 to a solution of N-carbobenzyloxy-L-proline methyl ester 41 (21 g, 0.08 mol) in THF (500 ml) at 0° C. The reaction mixture was allowed to stir at room temperature for 48 hours. The solution was then cooled to 0° C. and ice water (150 ml) was added to quench excess lithium tetrahydroborate. The resulting suspension was adjusted to pH 4.0 with aqueous HCl (1.0 N) and extracted with $Et_2O$ (250 ml). The organic phase was separated and washed with $H_2O$ (3×100 ml), brine (2×100 ml), dried ($MgSO_4$) and concentrated to give alcohol 42 as a pale yellow oil (18.6 g, 99%). $^1$HNMR (270 MHz, $CDCl_3$) d 2.1–1.77 (m, 4H); 3.76–3.35 (m, 4H); 4.1–3.77 (m, 1H); 5.14 (2×s, 2H); 7.38–7.28 (m, 5H). CIMS 236 ($M^+$)

A solution of triethylamine (32 ml, 0.23 mol) and $SO_3$.pyridine complex (37 g, 0.23 mol) in DMSO (210 ml) was added to a solution of alcohol 42 (18 g, 0.077 mol) in $CH_2Cl_2$ (250 ml) at −10° C., under a nitrogen atmosphere. The reaction mixture was allowed to warm to room temperature and stirred for 30 minutes and then poured into ice water (200 ml) and extracted with $Et_2O$. The organic phase was washed with aqueous HCl (1.0 N, 3×150 ml), $H_2O$ (3×150 ml), brine (2×150 ml), dried ($MgSO_4$) and concentrated to give a yellow oil. The crude material was purified by flash column chromatography (silica gel, EtOAc) to give aldehyde 43 as a colourless oil (12.6 g, 71%). $^1$H NMR (270 MHz, $CDCl_3$) δ 2.16–1.8 (m, 4H); 3.66–3.5 (m, 2H); 4.33–4.17 (m, 1H); 5.22–5.13 (m, 2H); 7.37–7.3 (m, 5H); 9.59 (2×s, 1H). CIMS 234 ($M^+$+1).

Thionyl chloride (5.5 ml) was added to a solution of aldehyde 43 (11 g, 0. 047 mol) and trimethyl orthoformate (36 ml, 0.33 mol) in MeOH (55 ml) at 0° C. The reaction mixture was heated at 60° C. for 2 hours. The solution was allowed to cool to room temperature, and treated with excess solid $Na_2CO_3$ and diluted with $Et_2O$ (60 ml). The suspension was filtered to remove insoluble inorganics and resultant filtrate was concentrated in vacuo and then redissolved in EtOAc. The organic solution was washed with saturated aqueous NaHCO, (3×50 ml), brine (2×50 ml), dried ($MgSO_4$) and concentrated to give acetal 44 as a yellow liquid (12.5 g, 95%). $^1$H NMR (270 MHz, $CDCl_3$) δ 2.16–1.7 (m, 4H); 3.64–3.33 (m, 8H); 4.02–3.91 (br. m, 1H); 4.4 and 4.6 (2×br. s, 1H); 5.17–5.1 (m, 2H); 7.47–7.28 (m, 5H).

A solution of acetal 44 (5.8 g, 0.02 mol) in EtOH (50 ml) was allowed to stir for 16 hours at room temperature over Raney nickel (0.2 g), in order to remove the trace amounts of sulphur impurities prior to hydrogenation. Nickel was removed by filtration through Celite.

10% Palladium on carbon (580 mg) was added to the alcoholic solution which was subjected to hydrogenation under pressure (c. 50 psi). After 16 h, the reaction mixture was filtered through Celite and the pad was washed with EtOAc, the combined organic solutions were concentrated to give secondary amine 45 as a pale green liquid (2.9 g, 100%). $^1$H NMR (270 MHz, $CDCl_3$) δ 1.93–1.59 (m, 4H); 3.1–2.92 (m, 2H); 3.4–3.3 (d, J=6.9 Hz, 1H); 3.41 (2×s, 6H); 3.53 (br.s, 1H); 4.2 (d, J=6.8 Hz, 1H)

Synthesis of Amine 48

A solution of acetal 45 (1 g, 6.9 mmol), 4,5-dimethoxy 2-nitrobenzoic acid 46 (1.6 g, 6.9 mmol), TBTU (2.2 g, 6.9 mmol) and DIPEA (1.2 ml, 6.9 mmol) in DMF (30 ml) were stirred at room temperature for 16 hours. The reaction mixture was concentrated in vacuo and the crude material was extracted with EtOAc and washed with saturated aqueous $NaHCO_3$ (3×30 ml), HCl (1.0 N, 3×30 ml), $H_2O$ (3×30 ml), brine (3×30 ml), dried ($MgSO_4$) and concentrated to give a yellow semi solid. The crude material was purified by flash column chromatography (silica gel, 2:1 EtOAc: petroleum ether 40–60) to give the nitro compound 47 as a pale cream solid (1.28 g, 51%). $^1$H NMR (270 MHz, $CDCl_3$) δ 2.26–1.67 (m, 4H); 3.19–3.06 (m, 2H); 3.59 and 3.57 (2×s, 6H); 3.98 (s, 6H); 4.45–4.4 (m, 1H); 4.95–4.94 (d, J=2.6 Hz, 1H); 6.76 (s, 1H); 7.71 (s, 1H); CIMS 355 ($M^+$+1).

10% Palladium on carbon (130 mg) was added to a solution of the nitro compound 47 (1.28 g, 3.6 mmol) in EtOH (50 ml), which was subjected to hydrogenation under pressure (c. 50 psi). After 20 hours, the reaction mixture was filtered through Celite and the, pad was washed with EtOAc, the combined organic solutions were concentrated to give secondary amine 48 as a pale oil (1.26 g, 98%). $^1$H NMR (270 MHz, $CDCl_3$) δ 2.18–1.65 (m, 4H); 3.57–3.47 (m, 8H); 3.85 and 3.8 (2×s, 6H); 4.42–4.38 (m, 1H); 4.74–4.7 (m, 1H); 6.3 (s, 1H); 6.77 (s, 1H); $^{13}$C NMR (68.7 MHz, $CDCl_3$) δ 24.03, 25.07, 50.56, 55.8, 56.24, 56.86, 57.65, 58.82, 101.07, 105.01, 111.75, 112.52, 141.07, 151.81, 169.76; EIMS 324 ($M^+$).

Synthesis of Psec-protected PBD 52

Pyridine (55 µl, 0.67 mmol) was added to a solution of 2-(phenylsulfonyl)ethanol 49 (375 mg, 2.01 mmol) and triphosgene (200 mg, 0.67 mmol) in $CH_2Cl_2$ (10 ml) at 0° C. The reaction mixture was stirred at room temperature for 16 hours. Pyridine (150 µl, 1.85 mmol) and crude chloroformate 50 were added to a solution of amine 48 (0.5 g, 1.5 mmol) in $CH_2Cl_2$ (20 ml) at 0° C. The reaction mixture was allowed to stir at room temperature for 3 hours. Then the solution was concentrated in vacuo and extracted with $CH_2Cl_2$. The organic phase was washed with 10% citric acid (2×20 ml), $H_2O$ (20 ml), brine (20 ml), dried ($MgSO_4$) and concentrated to give a yellow oil. The crude material was purified by flash column chromatography (silica gel, EtOAc) to give carbamate 51, as a colourless oil (770 mg, 93%).

$^1$H NMR (270 MHz, $CDCl_3$) δ 2.17–1.72 (m, 6H), 3.55–3.34 (m, 10H), 3.92 and 3.84 (2×s, 6H), 4.5–4.4 (m, 2H), 4.75 (br.s, 1H), 6.82 (s, 1H), 7.97–7.56 (m, 6H), 8.89 (br.s, 1H); $^{13}$C NMR (68.7 MHz, $CDCl_3$) δ 14.19, 21.04, 23.88, 55.31, 56.12, 56.31, 56.39, 57.52, 58.25, 58.94, 60.38, 103.91, 104.74, 111.15, 127.97, 128.09, 129.43, 133.98, 134.05, 139.29, 143.75, 151.09, 152.72, 168.83; FABMS 536 ($M^+$).

Trans-bis(acetonitrile)palladium (II) chloride (107 mg, 0.41 mmol) was added to a solution of carbamate 51 in anhydrous acetone (14 ml). The reaction mixture was stirred at room temperature for 16 hours. The solution was concentrated in vacuo to give a brown foam. The crude material was purified by flash column chromatography (silica gel, EtOAc) to give methyl ether 52, as an orange oil (690 mg, 85%).

$^1$H NMR (270 MHz, $CDCl_3$) δ 2.12–1.78 (m, 6H), 3.22–3.17 (m, 1H), 3.7–3.4 (m, 7H), 3.98 and 3.94 (2×s, 6H), 4.69–4.65 (m, 1H), 5.46–5.43 (d, J=9.3 Hz, 1H), 7.03 (s, 1H), 7.22 (s,1H), 7.87–7.53 (m, 5H); $^{13}$C NMR (68.7 MHz, $CDCl_3$) δ 14.19, 21.06, 23.21, 28.98, 46.33, 54.74, 56.15, 56.39, 56.45, 58.58, 60.09, 60.39, 93.33, 110.18, 113.32, 126.24, 128.07, 128.27, 129.49, 134.13, 138.59, 148.77, 151.15, 155.65, 167.36; EIMS 504 ($M^+$).

Synthesis of Ptec-PBD 55a/b

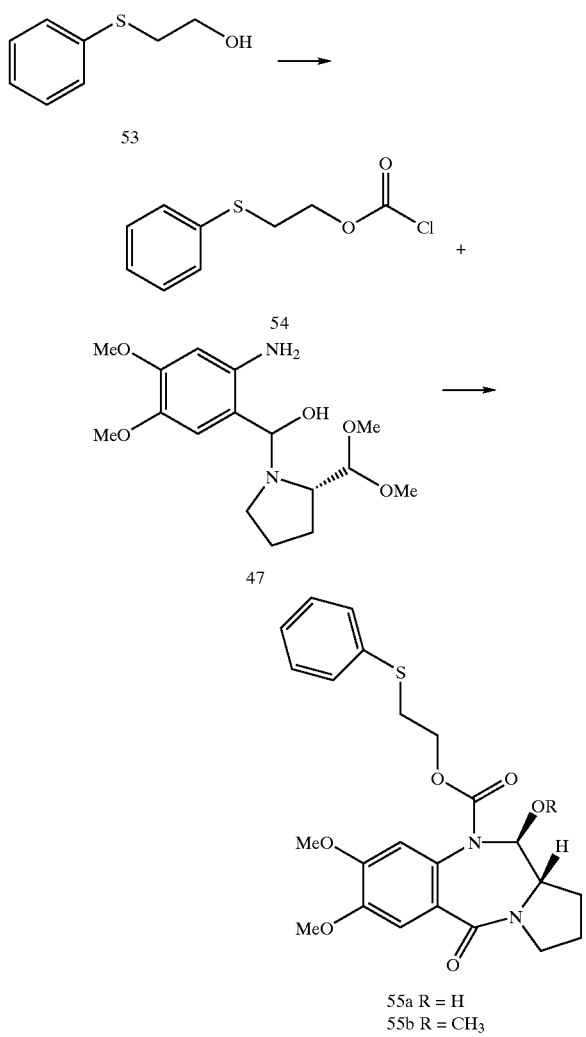

Pyridine (65 μl, 0.77 mmol) was added to a solution of 2-(phenylthio)ethanol 53 (355 mg, 2.3 mmol) and triphosgene (230 mg, 0.77 mmol) in CH$_2$Cl$_2$ (10 ml) at 0° C.. The reaction mixture was stirred at room temperature for 16 hours.

Pyridine (150 μl, 1.85 mmol) and crude chloroformate 54 were 10 added to a solution of amine 47 (0.5 g, 1.5 mmol) in CH$_2$Cl$_2$ (20 ml) at 0° C. The reaction mixture was allowed to stir at room temperature for 3 hours. Then the solution was concentrated in vacuo and extracted with CH$_2$Cl$_2$. The organic phase was washed with HCl (1.0 N, 2×20 ml), H$_2$O (20 ml), brine (20 ml), dried (MgSO$_4$) and concentrated to give a brown oil. The crude material was purified by flash column chromatography (silica gel, 2:1 EtOAc: petroleum ether 40–60) to give a mixture of carbinolamine 55a and methyl ether 55b, as a yellow gum (510 mg, 66%).

$^1$H NMR (270 MHz, CDCl$_3$) δ 2.1–1.99 (m, 4H); 3.15–2.98 (m, 2H), 3.71–3.44 (m, 4H), 3.93 and 3.89 (2×s, 6H), 4.38–4.07 (m, 1H), 5.45–5.41 (d, J=9.3 Hz,1H), 5.65–5.61 (d, J=9.5 Hz, 1H), 6.76 (s, 1H), 7.29–7.19 (m, 6H); $^{13}$C NMR (68.7 MHz, CDCl$_3$) δ 23.05, 23.21, 28.7, 28.98, 29.36, 29.68, 32.72, 32.99, 46.36, 56.13, 56.19, 56.59, 59.9, 60.13, 63.91, 64.19, 86.07, 93.37, 110.36, 112.55, 112.85, 125.67, 126.69, 128.3, 129.15, 129.72, 129.97, 134.85, 148.36, 150.83, 156.02, 167.05; EIMS 458 (M$^+$, 55a), 472 (M$^+$, 55b).

Example 7

Nitroreductase-activation of benzyl DC-81 prodrug (Compound 7)

Compound 7, synthesized according to example 1, was evaluated in two different cell lines, namely SW1116 and LS174T. Both SW1116 and LS174T are human adenocarcinoma colonic cell lines, which were grown at Charing Cross hospital. The cells, at a concentration of 2500 cells/ml, were plated in 96-well microtitre plates, and were incubated at 37° C. for 1 hour with different concentrations of the prodrug, in the presence or absence of *E. coli* nitroreductase-monoclonal antibody conjugate in phosphate buffer saline (available from Sigma), and NADH (the co-factor necessary for enzyme function) in DMSO. The cells were then washed and incubated for a further 3 days at 37° C. At the end of this period, the cells were fixed (TCA) and stained. The concentration of the remaining viable cells adhering to the plates was quantified by a sulforhodamine B (SRB) dye. The control sets of cells treated with the prodrug alone were used in order to evaluate the cytotoxicity of the compound prior to enzymatic activation.

Figure 4:
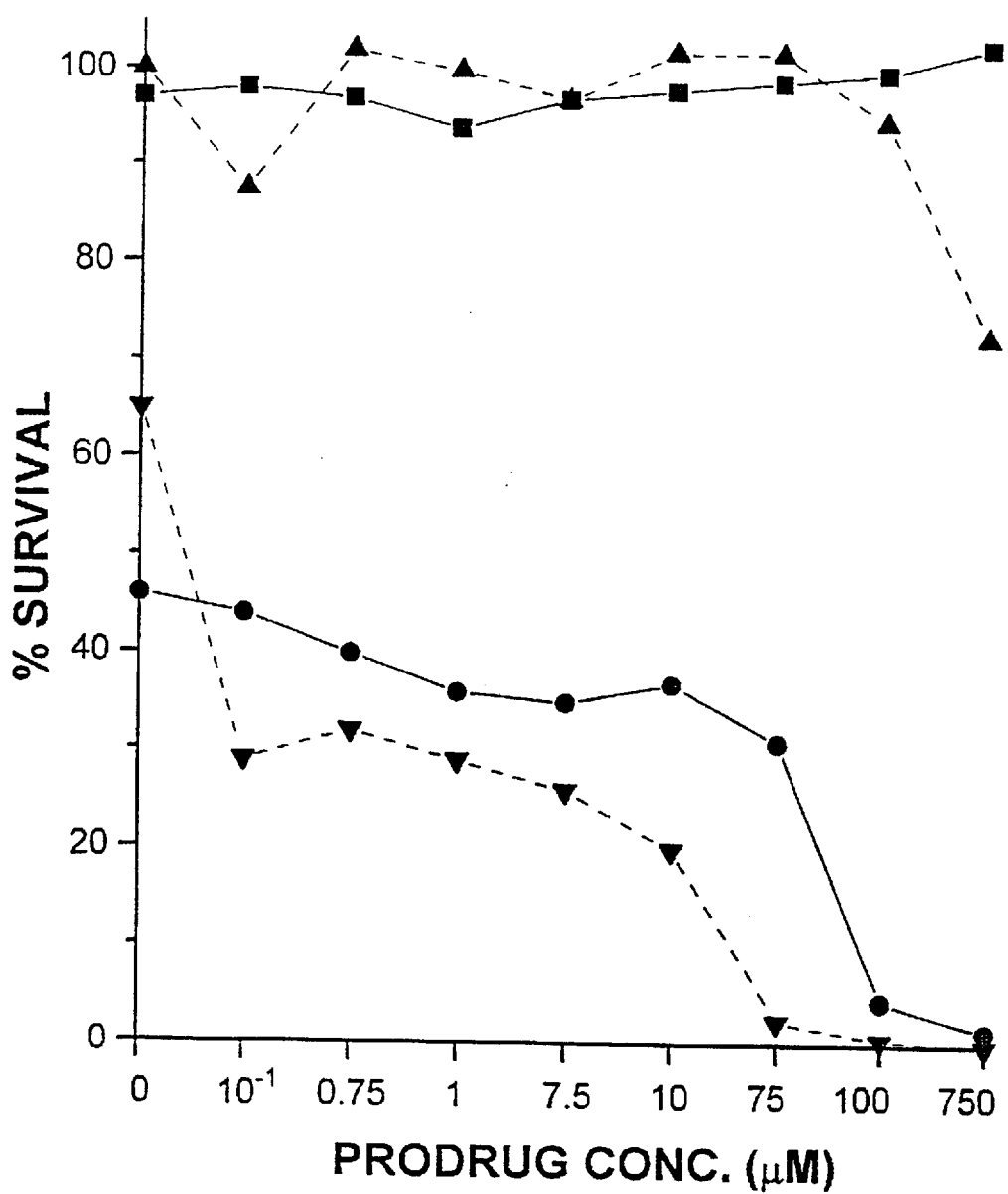
FIG. 4 is a graph illustrating the cytotoxicity results for prodrug compound 7 (see example 1), both before and after activation with nitroreductase/NADH in SW1116 cells and LS174T cells.

The results are illustrated in FIG. 4. The prodrug alone was found to be essentially non-toxic in SW1116 cells even at concentrations of up to 500 μM. A slight toxicity was observed in the LS174T cell line at concentrations higher than 100 μM. In the presence of the enzyme and co-factor, the IC5, of compound 7 was established as 1–5 μM in both cell lines.

The parent drug, benzyl DC-81 (Thurston et al, 1990, *Chem. Brit.*, 26, 767–772), was also evaluated in the same cell lines under the same conditions in order to establish the extent of activation achieved by the prodrug/enzyme system. A difference was observed between the IC$_{50}$ value of the parent drug (IC$_{50}$=0.008 μM) and the nitroreductase-activated prodrug (IC$_{50}$=1–5 μM) of 20–100 fold.

Example 8

Nitroreductase-activation of DSB-120 prodrug (Compound 30)

Compound 30, see examples 5(a) and 5(e), was evaluated in the LS174T cell line, under the same conditions as were used in example 6. The IC$_{50}$ value was found to be 215.3 μM (average of two measurements) which reduced to 13.7 μM after the addition of the enzyme and co-factor, representing a 15–16 fold activation factor. The cytotoxicity (IC$_{50}$) of the parent agent DSB-120 in this cell line was found to be 0.0005 μM, indicating less efficient activation of the dimer prodrug compared to compound 7.

Example 9

Nitroreductase-activation of benzyl tomaymycin prodrug (Compound 24)

Compound 24, see example 4, was examined in the same cell lines as example 6, and under the same conditions. It exhibited an IC$_{50}$ value of 86.2 μM (average of two experiments) which, after addition of the enzyme conjugate and NADH, dropped to 6.4 μM, indicating an activation factor of approximately 13.5. In this case, the parent benzyl tomaymycin was unavailable for evaluation as a control. However, assuming that the addition of a benzyl group to the C8-position of the A-ring of tomaymycin does not change the cytotoxicity of the compound significantly (as is the case for DC-81/C8-benzyl DC-81), the cytotoxicity of C8-benzyl tomaymycin should be in the order of 0.01–0.001 $\mu$M.

Example 10

Light-activation of the benzyl DC-81 prodrug (Compound 11)

Figure 5:
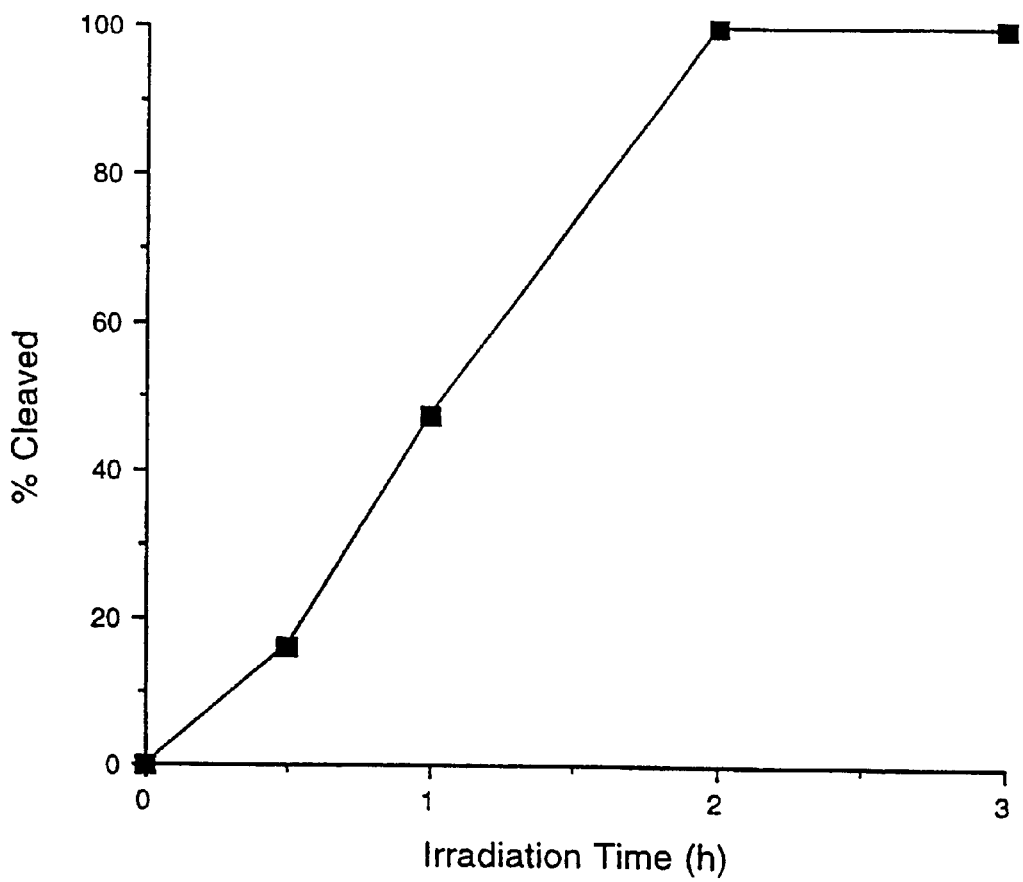
FIG. 5 is a graph illustrating the percentage of compound 11 (see example 3) cleaved by UVA (365 nm) exposure over a 3 hour time course.

This experiment involved the irradiation of compound 11, see example 3, in DMF at a concentration of 1 mM using a Stratagene UVA Crosslinker(365 nm). Small aliquots (100 $\mu$L) were removed at 30 minutes, 1 hour, 2 hours and 3 hours and the cleavageof the photolabile NVOC group was monitored by HPLC, using a Waters C4, 300 angstrom reversed phase column and a mobile phase of 50% methanol/50% water. Compound 11 has a retention time of 11.25 minutes and upon radiation produced a new peak with a retention time of 8.58 minutes. Authentic benzyl DC-81 has an identical retention time of 8.58 minutes. The time course of the deprotection process is shown in FIG. 5. Complete conversion is achieved by 2 hours of irradiation at 365 nm under the conditions employed.

An MTT assay was used to evaluate the ability of aliquots of the activated analogues, which were removed at time intervals, to inhibit the growth of chronic human histiocytic leukaemia K562 cells in culture. Following treatment of cells with a range of drug doses, cells were transferred to 96-well microtitre plates, $10^4$ cells per well, 8 wells per sample. Plates were incubated at 37° C. in a humidified atmosphere containing 5% $CO_2$. The assay is based on the ability of viable cells to reduce a yellow soluble tetrazolium salt 3-(4,5-dimethylthiazolyl)-2,5-diphenyltetrazolium bromide (MTT), to an insoluble purple formazan precipitate. Following incubation of the plates for 4 days (to allow control cells to increase 10-fold in number), 20 $\mu$L of a 5 mg/mL solution of MTT in phosphate-buffered saline was added to each well and the plates were incubated for a further 5 hours. The plates were then centrifuged for 5 minutes at 300 g and the bulk of the medium was removed from the cell pellet. DMSO (200 $\mu$L) was added to each well, and the samples agitated to ensure complete mixing. The optical density was then measured at a wavelength of 550 nm on a Titertek Multiscan ELISA plate reader and expressed as a percentage of the control optical density. For each curve, an $IC_{50}$ value was read as the dose required to reduce the final optical density to 50% of the control value.

Figure 6:
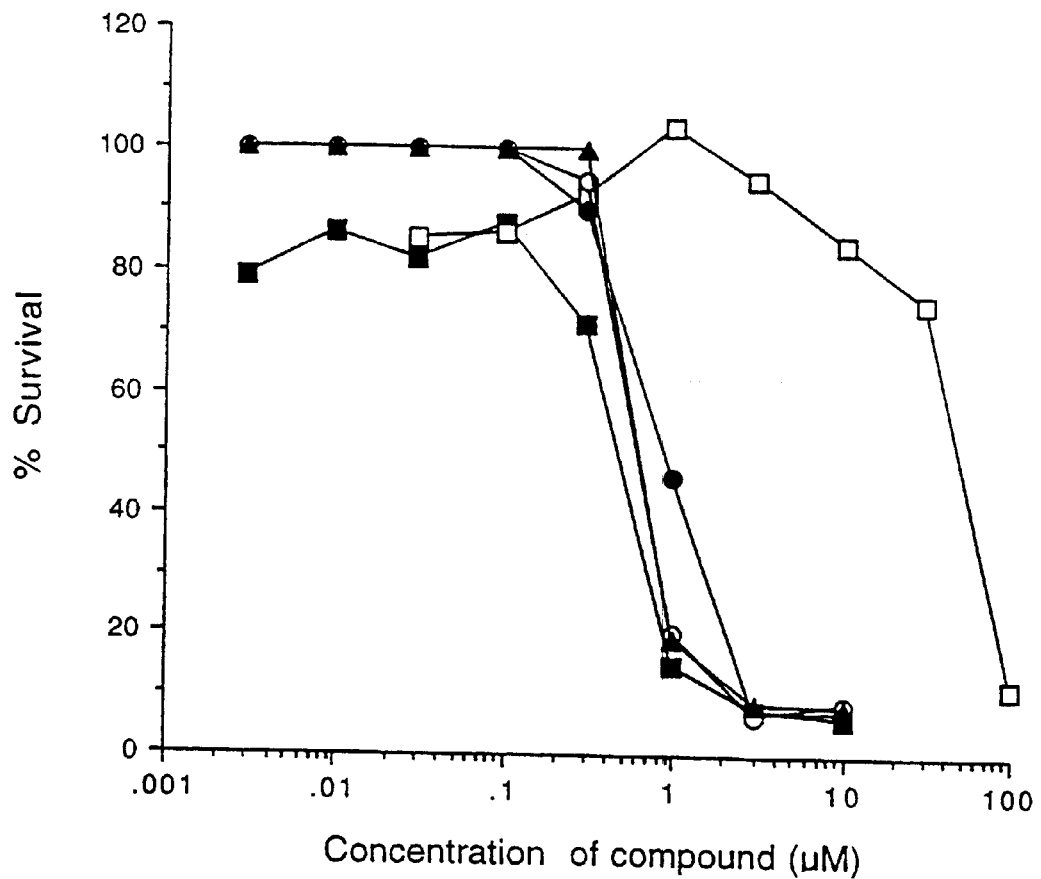
FIG. 6 is a graph illustrating the in vitro cytotoxicity ($IC_{50}$; $\mu M$) of benzyl DC-81 and compound 11, with varying irradiation times, against human chronic myeloid leukaemia K562 cells in DMF at 1 mM initial drug concentration.

The PBD prodrug compound 11 investigated was itself shown to have negligible cytotoxicity ($IC_{50}$=47.5 $\mu$M; FIG. 6). Following irradiation, significantly increased cytotoxicity was observed (FIG. 6) with an $IC_{50}$ value of 0.6 $\mu$M achieved after 1 hour of irradiation. The $IC_{50}$ value of authentic benzyl DC-81 under similar conditions was 0.5 $\mu$M.

| Compound | Irradiation Time (hours)+ | $IC_{50}$ ($\mu$M) |
|---|---|---|
| benzyl DC-81* | 0 | 0.5 |
| 11 | 0 | 47.5 |
|  | 0.5 | 0.98 |
|  | 1.0 | 0.60 |
|  | 2.0 | 0.60 |

*comparative example
+irradiation was in DMF at 1 mM initial drug concentration

Figure 7:
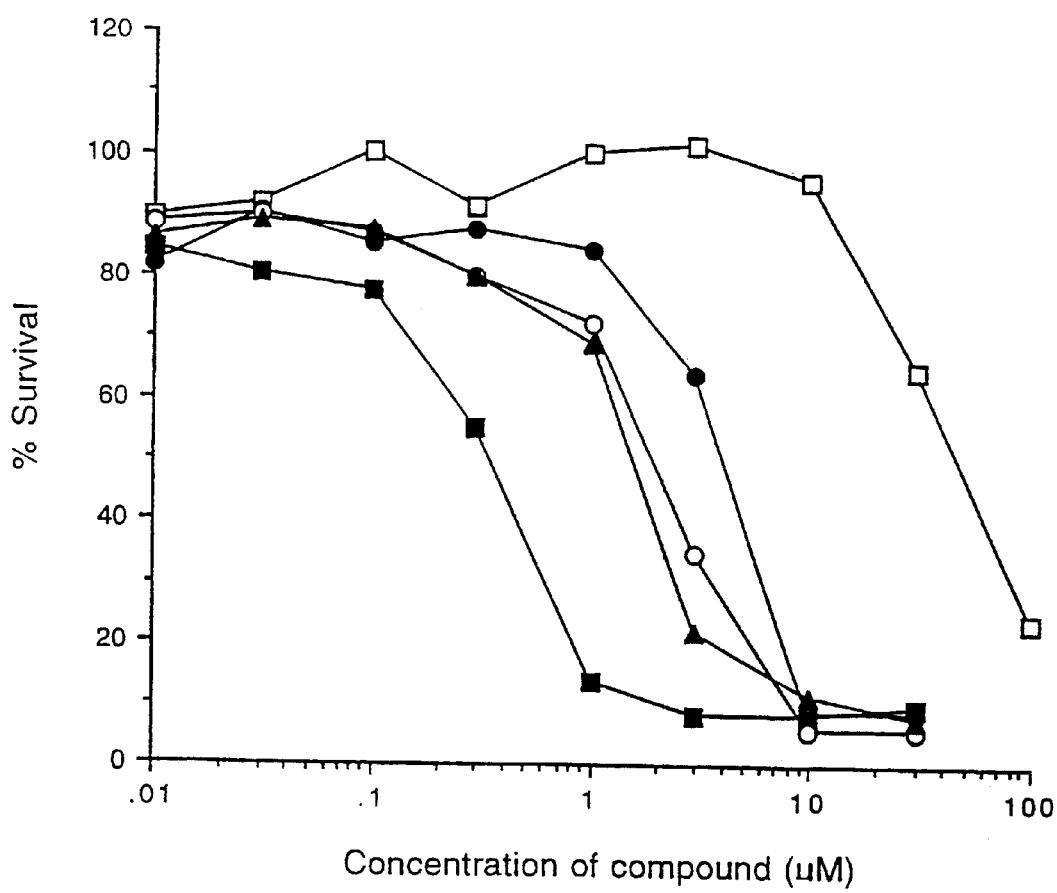
FIG. 7 is a graph illustrating the in vitro cytotoxicity ($IC_{50}$; $\mu M$) of benzyl DC-81 and compound 11, with varying irradiation times, against human chronic myeloid leukaemia K562 cells in DMF at 10 mM initial drug concentration.

The efficiency of photoinduced cleavage was reduced at the higher concentration of 10 mM of prodrug in DMF, when 2 hours irradiation gave an $IC_{50}$ value of 1.75 $\mu$M, see FIG. 7.

| Compound | Irradiation Time (hours)+ | $IC_{50}$ ($\mu$M) |
|---|---|---|
| benzyl DC-81* | 0 | 0.5 |
| 11 | 0 | 48.5 |
|  | 0.5 | 4.33 |
|  | 1.0 | 2.17 |
|  | 2.0 | 1.75 |

*comparative example
+irradiation was in DMF at 10 mM initial drug concentration It was thought that the high concentration of prodrug might be preventing efficient absorption of UV light. Furthermore, changing the solvent from DMF to methanol resulted in a less efficient conversion, see FIG. 8.

| Compound | Irradiation Time (hours)+ | $IC_{50}$ ($\mu$M) |
|---|---|---|
| benzyl DC-81* | 0 | 0.5 |
| 11 | 0 | 47.5 |
|  | 0.5 | 4.5 |
|  | 1.0 | 4.0 |
|  | 2.0 | 3.2 |

*comparative example
+irradiation was in DMF at 1 mM initial drug concentration

Example 11

Light-activation of the dimer DSB-120 prodrug (Compound 32)

Figure 9:
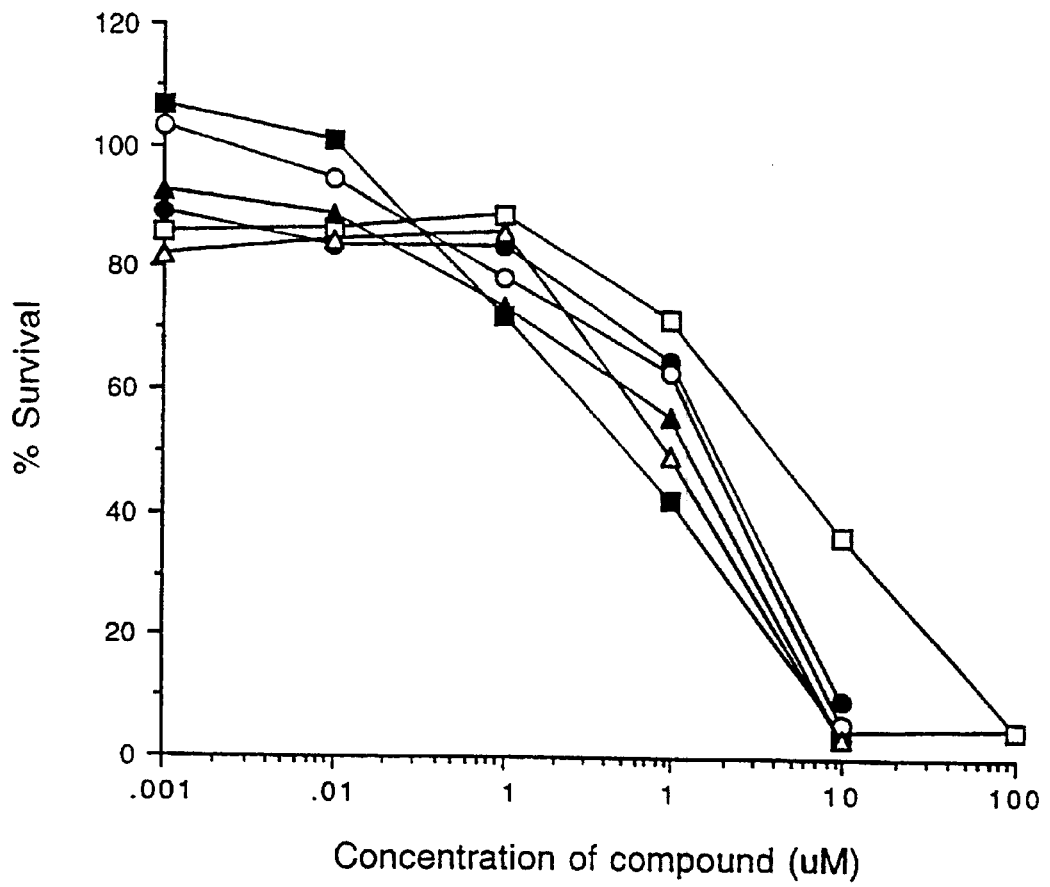
FIG. 9 is a graph illustrating the in vitro cytotoxicity ($IC_{50}$; $\mu M$) of DSB-120 and compound 32, with varying irradiation times, against human chronic myeloid leukaemia K562 cells in methanol at a 1 mM initial drug concentration.

The dimer derivative 32, see example 5(b), was found to be slightly cytotoxic before UV irradiation with an $IC_{50}$ of 4.5 $\mu$M. 5 Incubation of a solution of compound 32 with cells following 2 hours irradiation reduced the $IC_{50}$ to 1.25 $\mu$M (FIG. 9). This was further reduced to 0.85 $\mu$M following 5 hours irradiation. The parent PBD dimer DSB-120 gave an $IC_{50}$ of 0.55 $\mu$M in the same cell line, see FIG. 9.

| Compound | Irradiation Time (hours)+ | $IC_{50}$ ($\mu$M) |
|---|---|---|
| DSB-120* | 0 | 0.55 |
| 32 | 0 | 4.50 |
|  | 0.5 | 1.90 |
|  | 1.0 | 1.75 |
|  | 2.0 | 1.25 |
|  | 5.0 | 0.85 |

*Comparative example
+irradiation was in DMF at 1 mM initial drug concentration

For these experiments, the HPLC data (not shown) suggested that almost complete conversion of the prodrug 32

(retention time=5.18 minutes) to a product with retention time=3.64 minutes occurred by 2 hours irradiation, with complete conversion by 5 hours. Authentic DSB-120 eluted with a retention time of 3.64 minutes.

Example 12

Comparison of Biological Activity of Psec and Ptec protected PBDs (Compounds 52 and 55)

Compounds 52 (UP 2073) and the comparative compound 55b (UP2090) were evaluated for their cytotoxic activity in ovarian cell lines by Dr Lloyd R. Kelland's group at The Institute of Cancer Research, Sutton, UK. The five cell lines investigated were SKOV-3, A2780/A2780cisR and CH1/CH1cisR (cisR denotes that the cell line is resistant to cisplatin).

Single viable cells were seeded in growth medium (160 µL) in 96-well microtitre plates and allowed to attach overnight. The test compounds were then dissolved in DMSO (to give 20 mM drug concentrations) immediately prior to adding the cells in quadruplicate wells. The final drug concentrations in the wells ranged from 100 µM to 2.5 nM as follows:100, 25, 10, 2.5, 1 µM, 250, 100, 25, 10, 2.5 nM (drugs were diluted in growth medium and then 40 µL added to the existing well volume of 160 µL to give final concentrations as above). After 96 hours, the medium was removed and the remaining cells fixed by exposure to 10% trichloroacetic acid on ice for 30 minutes. The wells were then washed 3–4 times with tap water, air dried overnight and treated with 100 µL of sulphorhodamine B (0.4%) dissolved in 1% acetic acid. Staining was allowed to continue for 10–15 minutes, then the wells were washed 3–4 times with 1% acetic acid, air dried and then added to Tris base (100 µL of 10 mM). Plates were then shaken and absorbance readings at 540 nM were determined using a plate reader. The $IC_{50}$ values were calculated from plots of concentration versus percentage absorbance (compared with 8 untreated wells).

The assay was also carried out using compound 56 (UP2025):

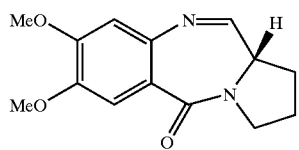

56 which is the unprotected version of compound 52.
The results are shown below:

| Cell Lines | UP2090 $IC_{50}$ (µM) | UP2073 $IC_{50}$ (µM) | UP2025 $IC_{50}$ (µM) |
|---|---|---|---|
| A2780 | >25 | 0.48 | 0.064 |
| A2780cisR | >25 | 0.49 | 0.155 |
| RF | N/A | 1 | 2.4 |
| CH1 | >25 | 0.4 | 0.082 |
| CH1cisR | >25 | 0.47 | 0.11 |
| RF | N/A | 1.2 | 1.3 |
| SKOV3 | >25 | 0.56 | 1.7 |

RF is the resistance factor, which is the cytotoxicity of the compound in the cisplatin resistant cell line divided by the cytotoxicity in the normal cell line.

The Ptec protected PBD (55b), UP2090, was essentially inactive in against the ovarian cell lines, as expected as the Ptec protecting group lacks the acidic protons thought to be required to trigger the fragmentation of the protecting group when exposed to GST. However, the Psec-protected prodrug (52) UP2073 was found to be at least 50 times more toxic than the Ptec control. The compound was particularly active against the SKOV3 cell line; this is noteworthy as this cell line is intrinsically resistant to electrophilic cytotoxic agents due to the presence of high levels of glutathione/glutathione transferase. Interestingly, the Psec prodrug UP2073 was actually more active in this cell line than the PBD it was based upon UP2025. Without wishing to be bound by theory, it is possible that the prodrug is protected from glutathione and other biological nucleophiles until it is deprotected close to the site of action.

UP2073 also underwent screening carried out by The National Cancer Institute (NCI), Bethesda, Md. USA. The NCI has available an in vitro cytotoxicity screen which consists of approximately 60 human tumour cell lines against which compounds are tested at a minimum of five concentrations each differing 10-fold. A 48 hour continuous exposure protocol is used, where cell viability or growth is estimated with an SRB protein assay.

Method

The test compound was evaluated against approximately 60 human tumour cell lines. The NCI screening procedures were described in detail by Monks and co-workers (Monks, A et al., Journal of the National Cancer Institute, 1991, 83, 757). Briefly, cell suspensions were diluted according to the particular cell type and the expected target cell density (5000–40,000 cells per well based on cell growth characteristics), and added by pipette (100 uL) into 96-well microtitre plates. The cells were allowed a preincubation period of 24 hours at 37° C. for stabilisation. Dilutions at twice the intended test concentration were added at time zero in 100 µL aliquots to the wells. The test compounds were evaluated at five 10-fold dilutions ($10^{-4}$, $10^{-5}$, $10^{-6}$, $10^{-7}$ and $10^{-8}$ µM). The test compounds were incubated for 48 hours in 5% $Co_2$ atmosphere and 100% humidity. The cells were then assayed using the sulphorhodamine B assay. A plate reader was used to read the optical densities and a microcomputer processed the readings into $LC_{50}$ values, which is the dosage required to kill half of the cells. $IC_{50}$ values, the dosage required to inhibit the growth of half the cells, was also measured.

UP2073 did well in the screening showing activity against cell lines in the lung, colon, CNS, melanoma, renal and breast tumour cell line panels. Interestingly, analysis of the $LC_{50}$ data across 53 cell lines suggested some correlation to glutathione transferase activity. Selected results are shown below:

| Cell Lines | $IC_{50}$ (µM) | $IC_{50}$ (µM) |
|---|---|---|
| Lung, NCI-H552 | 0.11 | 1.38 |
| Colon, Colo 205 | 0.19 | 0.71 |
| CNS, SNB-75 | 0.72 | 9.00 |
| Melanoma, SK-MEL-5 | 0.29 | 6.78 |
| Renal, RXF 393 | 0.24 | 2.97 |
| Breast, MDA-MB-231 | 0.45 | 4.33 |

Key to Figures

FIG. 4: SW1116–(■) Compound 7; (●) Compound 7+enzyme+NADH
Ls174T–(▲) Compound 7; (▼) Compound 7+enzyme+NADH
FIGS. 6 & 7: (■) Benzyl DC-81; (□) Compound 11; (●) Compound 11+UVA 30 mins; (○) Compound 11+UVA 1 h; (▲) Compound 11+UVA 2 h.

Figure 8:
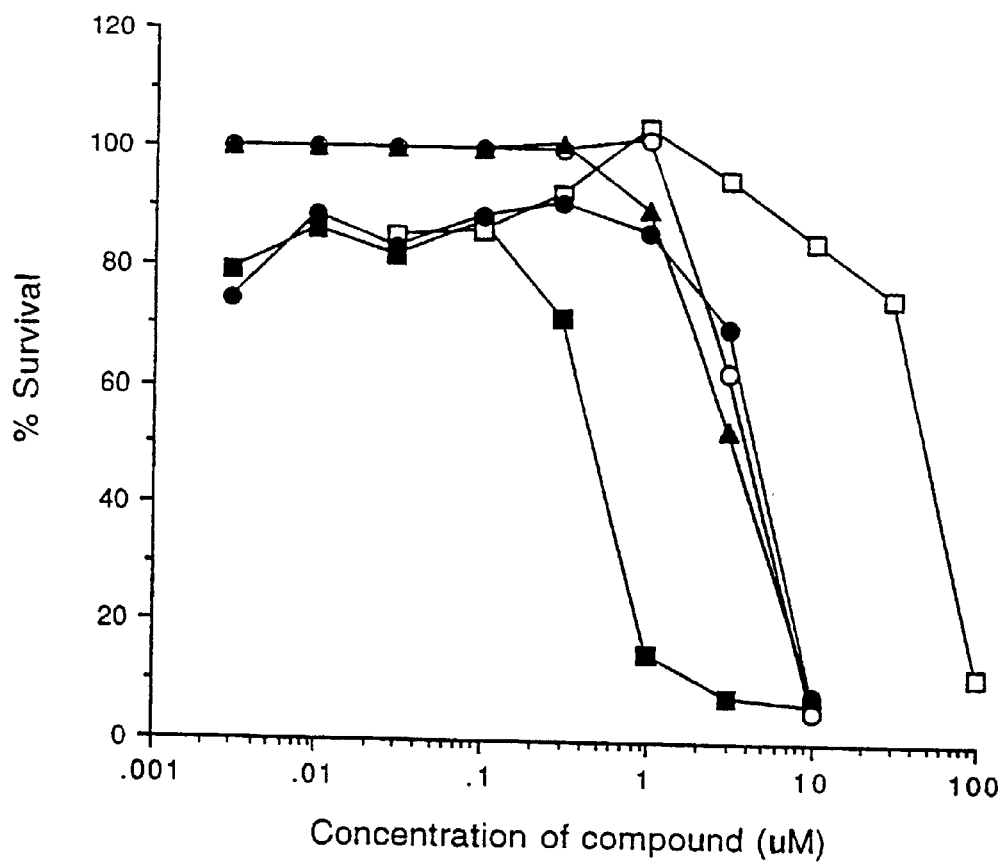
FIG. 8 is a graph illustrating the in vitro cytotoxicity ($IC_{50}$; $\mu M$) of benzyl DC-81 and compound 11, with varying irradiation times, against human chronic myeloid leukaemia K562 cells in methanol at a 1 mM initial drug concentration.

FIG. 8: (■) Benzyl DC-81; (□)) Compound 11; (●) Compound 11+UVA 30 mins; (○) Compound 11+UVA 1 h; (▲) Compound 11+UVA 2 h FIG. 9: (■) DSB-120; (□) Compound 32; (●) Compound 32+UVA 30 mins; (○) Compound 32+UVA 1 h; (●) Compound 32+UVA 2 h; (Δ) Compound 32+UVA 5 h

What is claimed is:

1. A compound with the formula I:

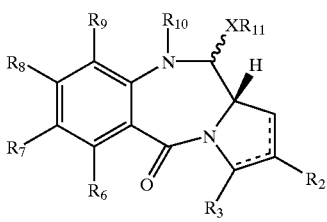

(I)

wherein:

$R_{10}$ is selected from the group consisting of:
(a)

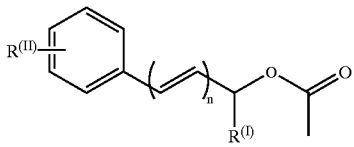

wherein n is 0 to 3 and $R^{(I)}$ is H or R and $R^{(II)}$ is one or more substituents selected from $NO_2$, OR and R, or a group of formula $-O-(CH_2)_m-O-$ attached to adjacent atoms, where m is 1 or 2, or

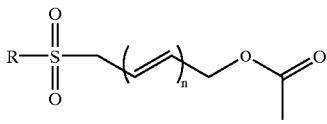

wherein n is 0 to 3;

$R_2$ and $R_3$ are independently selected from: H, R, OH, OR, =O, =CH—R, =CH$_2$, CH$_2$—CO$_2$R, CH$_2$—CO$_2$H, CH$_2$—SO$_2$R, O—SO$_2$—R, CO$_2$R, COR and CN;

$R_6$, $R_7$ and $R_9$ are independently selected from H, R, OH, OR, halo, amino, nitro, Me$_3$Sn; or $R_7$ and $R_8$ together form a group $-O-(CH_2)_p-O-$, where p is 1 or 2;

X is S, O or NH;

$R_{11}$ is either H or R;

wherein R is a lower alkyl group having 1 to 10 carbon atoms, or an aralkyl group, of up to 12 carbon atoms, whereof the alkyl group optionally contains a carbonyl group or one or more carbon-carbon double or triple bonds, which may form part of a conjugated system, or an aryl group of up to 12 carbon atoms; and wherein R is optionally substituted by one or more halo, hydroxy, amino or nitro groups;

and where there is optionally a double bond between C1 and C2 or C2 and C3; and $R_8$ is selected from H, R, OH, OR, halo, amino, nitro, Me$_3$Sn, where R is as defined above, or the compound is a dimer with each monomer being the same or different and being of formula I, where the $R_8$ groups of the monomers form together a bridge having the formula $-T-R'-T-$ linking the monomers, where R' is an alkylene chain containing from 3 to 12 carbon atoms, which chain may be interrupted by one or more hetero atoms and/or aromatic rings, and may contain one or more carbon-carbon double or triple bonds, and each T is independently selected from O, S or N.

2. A compound according to claim 1, wherein $R_{10}$ is of the formula II:

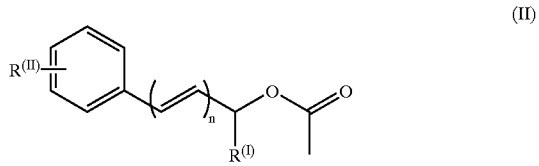

(II)

wherein n is 0 to 3, and $R^{(II)}$ is one or more substituents independently selected from $NO_2$, OR, or R, where R is as defined in claim 1, or a group of formula $-O-(CH_2)_m-O-$ attached to adjacent atoms, where m is 1 or 2.

3. A compound according to claim 1, wherein $R_{10}$ is of the formula III:

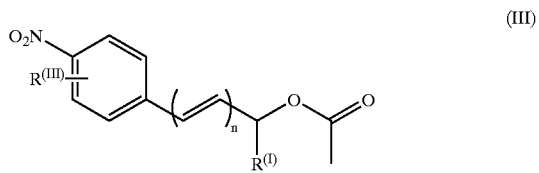

(III)

wherein n is 0 to 3, $R^{(I)}$ is H or R, and $R^{(III)}$ is one or more optional substituents independently selected from $NO_2$, OR, or R, where R is as defined in claim 1, or a group of formula $-O-(CH_2)_m-O-$ attached to adjacent atoms, where m is 1 or 2.

4. A compound according to claim 1, wherein $R_{10}$ is of the formula XI:

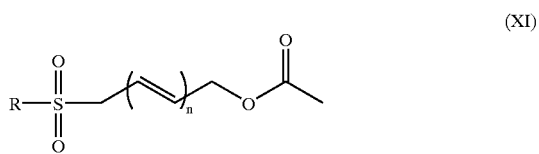

(XI)

wherein R is as defined in claim 1, and n is 0 to 3.

5. A compound according to claim 4, wherein R in the group formula XI is a substituted or unsubstituted phenyl group.

6. A compound according to claim 1 wherein X is O.

7. A compound according to claim 1 wherein $R_{11}$ is H.

8. A compound according to claim 1 wherein $R_6$ and $R_9$ are H.

9. A compound according to claim 8, wherein $R_7$ and $R_8$ are independently selected from H, OH and OR.

10. A compound according to claim 1 wherein the compound is a C8 dimer, wherein $R_6$ and $R_9$ are H, and $R_7$ is independently selected from H, OH, and OR, where R is as defined in claim 1.

11. A compound according to claim 10 wherein the compound is a C8 dimer, both Ts are O, and R' is $-(CH_2)_{p'}-$ where p' is from 3 to 12, so as to form a bridge of formula $-O-(CH_2)_{p'}-O-$ between the monomers.

12. A method of preparing a compound of formula I as defined in claim 1 wherein $XR_{11} \neq OH$ from a compound of formula Ia:

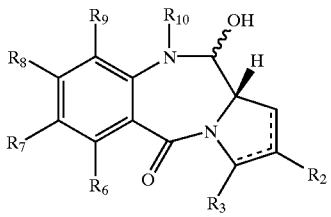

(Ia)

wherein the substituents of the compound of formula Ia are the same as for the compound of formula I to be prepared, by (a) direct esterification when $XR_{11}$ is $OR_{11}$; (b) treatment with $R_{11}SH$ and a catalyst when $XR_{11}$ is $SR_{11}$; (c) treatment with $R_{11}NH_2$ and a catalyst when $XR_{11}$ is $NHR_{11}$.

13. A method of preparing a compound of formula Ia as defined in claim 12 by the oxidation of a compound of formula IVa:

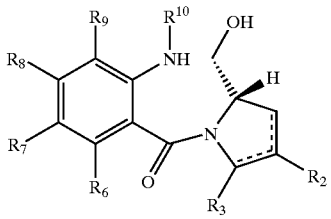

(IVa)

wherein the substituents of the compound of formula IVa are the same as for the compound of formula Ia to be prepared.

14. A method according to claim 13, wherein the oxidation is a Swern oxidation.

15. A method of preparing a compound of formula IVa as defined in claim 13, by reacting a compound of formula Va:

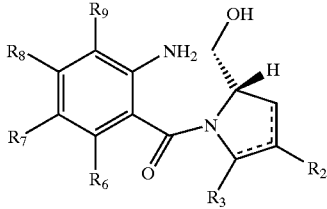

(Va)

with a compound of formula VI:

    (VI)

wherein the substituents of the compounds of formulae Va and VI are the same as for the compound of formula IVa to be prepared, and Y is a halogen atom.

16. A method according to claim 15, wherein $R_{10}$ is a group of formula

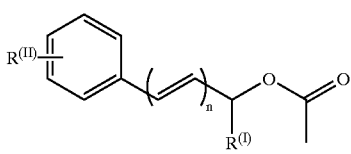

(II)

wherein n is 0 to 3, $R^{(I)}$ is H or R, and $R^{(II)}$ is one or more substituents independently selected from $NO_2$, OR, or R, or a group of formula —O—$(CH_2)_m$—O— attached to adjacent atoms, where m is 1 or 2.

17. A method of making a compound of formula IVa as defined in claim 13, by reacting a compound of formula VII:

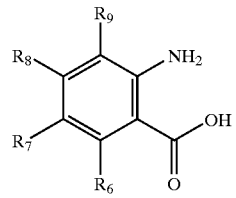

(VII)

with a compound of formula VI:

    (VI)

to form a compound of formula VIII:

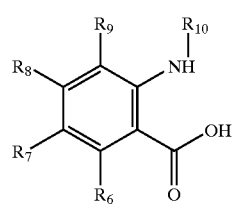

(VIII)

and then reacting the compound of formula VIII with a compound of formula IXa:

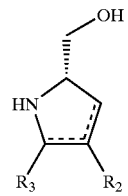

(IXa)

via the formation of an acid chloride, wherein the substituents for compounds of formulae VI, VII, VIII and IXa are the same as for the compound of formula IVa to be prepared, and where Y is a halogen atom.

18. A method of preparing a compound of formula Ia as defined in claim 12 by the unmasking of a compound of formula IVb:

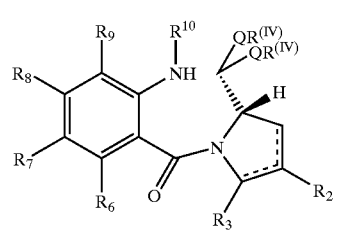

(IVb)

wherein the substituents of the compound of formula IVb are the same as for the compound of formula Ia to be prepared, Q is either O or S and $R^{(IV)}$ is Me or Et, or together form —$(CH_2)_q$— where q is 2 or 3.

19. A method according to claim 18, wherein Q is S, $R^{(IV)}$ is Et and the unmasking is mercury-mediated unmasking.

20. A method according to claim 18, wherein Q is O, $R^{(IV)}$ is Me and the unmasking is palladium-mediated unmasking.

21. A method of preparing a compound of formula IVb as defined in claim 18, by reacting a compound of formula Vb:

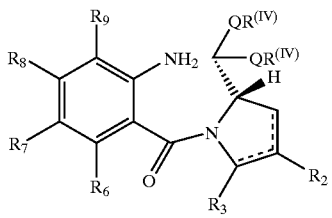

(Vb)

with a compound of formula VI:

Y—R$_{10}$ (VI)

wherein the substituents of the compounds of formulae Vb and VI are the same as for the compound of formula IVb to be prepared, and Y is a halogen atom.

22. A method according to claim 21, wherein R$_{10}$ is a group of formula II:

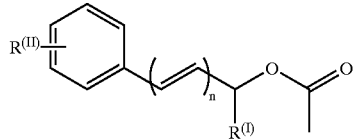

(II)

wherein n is 0 to 3; R$^{(I)}$ is H or R, and R$^{(II)}$ is one or more substituents independently selected from NO$_2$, OR, or R, or a group of formula —O—(CH$_2$)$_m$—O— attached to adjacent atoms, where m is 1 or 2.

23. A method of making a compound of formula IVb as defined in claim 18, by reacting a compound of formula VII:

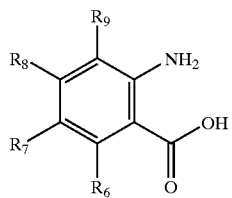

(VII)

with a compound of formula VI:

Y—R$_{10}$ (VI)

to form a compound of formula VIII:

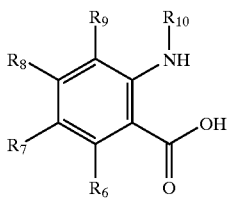

(VIII)

and then reacting the compound of formula VIII with a compound of formula IXb:

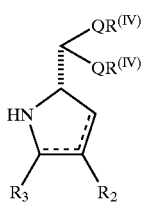

(IXb)

via the formation of an acid chloride, wherein the substituents for compounds of formulae VI, VII, VIII and IXb are the same as for the compound of formula IVb to be prepared, and where Y is a halogen atom.

24. A method of making a compound of formula X:

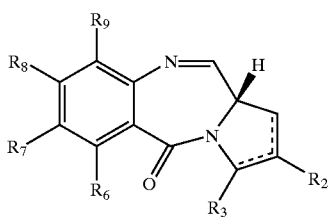

(X)

by the cleavage of the protecting group R$_{10}$ of a compound of formula I as defined in claim 1, wherein the substituent groups of the compound of formula X are the same as the substituent groups of the compound of formula I used.

25. A pharmaceutical composition comprising a compound of formula I as defined in claim 1 and a pharmaceutically acceptable carrier or diluent.

* * * * *